US007722869B2

(12) United States Patent
Burnie et al.

(10) Patent No.: US 7,722,869 B2
(45) Date of Patent: May 25, 2010

(54) ANTIBODY MOLECULES AND NUCLEIC ACIDS

(75) Inventors: James Burnie, Cheshire (GB); Philipp Wechner, Schwaz (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/150,076

(22) Filed: Apr. 24, 2008

(65) Prior Publication Data

US 2009/0136484 A1 May 28, 2009

(30) Foreign Application Priority Data

Apr. 27, 2007 (EP) .................. 07107140
Jul. 27, 2007 (EP) .................. 07113353

(51) Int. Cl.
A61K 39/395 (2006.01)
C12P 21/08 (2006.01)
C07H 21/04 (2006.01)

(52) U.S. Cl. .............. 424/135.1; 424/130.1; 424/133.1; 424/139.1; 424/141.1; 530/300; 530/350; 530/388.1; 530/388.5; 536/23.1; 536/23.5; 536/23.7; 435/69.1; 435/69.7

(58) Field of Classification Search ........................ None
See application file for complete search history.

(56) References Cited

U.S. PATENT DOCUMENTS

| 4,732,852 | A | 3/1988 | Cohen et al. | ................... 435/68 |
| 4,806,465 | A | 2/1989 | Buckley et al. | ................. 435/7 |
| 5,288,639 | A | 2/1994 | Burnie et al. | ............ 435/320.1 |
| 5,541,077 | A | 7/1996 | Burnie et al. | .............. 435/7.31 |
| 5,686,248 | A | 11/1997 | Burnie et al. | ................... 435/6 |
| 6,583,268 | B2 | 6/2003 | Lin | |
| 2003/0180285 | A1 | 9/2003 | Burnie | ..................... 424/130.1 |

FOREIGN PATENT DOCUMENTS

| EP | 0 145 333 | 6/1985 |
| EP | 0 406 029 | 3/1995 |
| EP | 0 861 892 | 9/1998 |
| EP | 0 861 893 | 9/1998 |
| EP | 1 267 925 | 6/2007 |
| GB | 2240979 | 8/1991 |
| WO | 86/05400 | 9/1986 |
| WO | 94/04676 | 3/1994 |
| WO | 00/61578 | 10/2000 |
| WO | 01/76627 | 10/2001 |
| WO | WO0176627 A1 * | 10/2001 |
| WO | WO02/06990 | 1/2002 |
| WO | 02/069900 A | 9/2002 |
| WO | 03/046007 | 6/2003 |
| WO | 2005/000300 A | 1/2005 |
| WO | WO 2005/000300 | 1/2005 |
| WO | 2005/102386 | 11/2005 |
| WO | 2005/102386 A | 11/2005 |
| WO | 2006/003384 | 1/2006 |
| WO | 2006/003384 A | 1/2006 |
| WO | 2008/132152 | 11/2008 |
| WO | 2008/132174 | 11/2008 |

OTHER PUBLICATIONS

Proba et al J.Mol. Biol 1997, 265, 161-172.*
Rudikoff et al PNAS, 1986, 83:7875-7878.*
Casset et al (Biochemical and Biophysical Research Communications, 307:198-205, 2003).*
MacCallum et al (J. Mol. Biol., 262,732-745, 1996).*
Bendig M. M. (Methods: A Companion to Methods in Enzymology, 1995; 8:83-93).*
Colman P. M. (Research in Immunology, 145:33-36, 1994.*
Rudikoff et al (Proc. Natl. Acad. Sci. USA, 79(6):1979-1983, Mar. 1982).*
Paul, Fundamental Immunology, 3rd Edition, 1993, pp. 292-295.*
Matthews R C et al., "Human Recombinant Antibody to HSP90: A Natural Partner in Combination Therapy", Current Molecular Medicine, vol. 5, No. 4, pp. 403-411, (2005).
Neckers L et al., "Heat-Shock Protein 90 Inhibitors as Novel Cancer Chemotherapeutics-An update", Expert Opinion on Emerging Drugs, vol. 10, No. 1, pp. 137-149, (2005).
Anonymous: "Mycograb", Internet Article, Jun. 16, 2006, XP002495190, Retrieved from the Internet: Sep. 9, 2008 URL:http//web.archive.org/web/20060616021547/http://neutecpharma.com/mycograb.html.
EMEA: "Refusal CHMP Assessment Report for Mycograb", European Medicines Agency, pp. 1-46, (2007).
Matthews Ruth C et al., "Preclinical Assessment of the Efficacy of Mycograb, a Human Recombinant Antibody Against Fungal HSP90", Antimicrobial Agents and Chemotherapy, vol. 47, No. 7, pp. 2208-2216, (2003).
Matthews R et al., "Antifungal Antibodies: A New Approach to the Treatment of Systemic Candidiasis", Current Opinion in Investigational Drugs, vol. 2, No. 4, pp. 472-476, (2001).
International Search Report PCT/EP2008/055006, mailed Sep. 25, 2008.
WHO Drug Information, vol. 21, No. 1, 2007, International Nonproprietary Names for Pharmaceutical Substances (INN) List 57.
WHO Drug Information, vol. 20, No. 2, 2006, International Nonproprietary Names for Pharmaceutical Substances (INN) List 95, published Aug. 21, 2006.
U.S. Appl. No. 10/240,819, filed Oct. 7, 2002, Burnie James.
U.S. Appl. No. 11/984,177, filed Nov. 14, 2007, Burnie James.
U.S. Appl. No. 12/076,643, filed Mar. 20, 2008, Burnie James.
U.S. Appl. No. 12/076,705, filed Mar. 21, 2008, Burnie James.

(Continued)

*Primary Examiner*—Robert B Mondesi
*Assistant Examiner*—Padma V Baskar
(74) *Attorney, Agent, or Firm*—Leslie Fischer

(57) ABSTRACT

An scFv peptide comprising a $V_H$ domain and a $V_L$ domain linked by an amino acid spacer is disclosed. The $V_H$ domain comprises a sequence with at least 80% sequence identity to the sequence of SEQ ID NO. 64. The $V_L$ domain comprises a sequence with at least 80% sequence identity to the sequence of SEQ ID NO. 66. The scFv peptide also comprises the substitution or deletion of an amino acid in the $V_H$ domain at the position corresponding to $C_{28}$.

18 Claims, 21 Drawing Sheets

OTHER PUBLICATIONS

Matthews R et al., "The role of hsp90 in fungai infection", Immunology Today, vol. 13, No. 9, pp. 345-348, (1992).

Matthews R C et al., "Autoantibody to heat-shock protein 90 can mediate protection against systemic candidosis", Immunology, vol. 74, No. 1, pp. 20-24, (1991).

Burnie, J.P., "Antibiotic Treatment of Systemic Fungal Infections", Current Anaesthesia and Critical Care, vol. 8, pp. 180-183, (1997).

Vrany, J., "The effect of foliar application of urea on the root fungi of wheat growing in soil artificially contaminated with *Fusarium* spp", Folia Microbiologica, vol. 17, No. 6, pp. 500-504, (1972).

Granger, D.L., et al., "Macrophage oxidation of L-arginine is linked to fungistatic capability, in Microbial Determinants of virulence and host response", pp. 147-162, E. Ayoub, Ed., American Society of Microbiology, Washington, DC, (1990).

Matthews et al., "Cloning of a DNA sequence encoding a major fragment of the 47 KD stress protein homologue of *Candida albicans*", FEMS Microbiology Letters, 60:25-30, (1989).

Matthews et al., "Immunoblot analysis of the serological response in systemic candiosis", Lancet, pp. 1415-1418, (1984).

Burnie et al., Lancet, "47 KD antigen of *Candida albicans*", pp. 1155, (1985).

Farrelly et al., "Complete sequence of the heat shock-inducible *HSP90* gene of *Saccharomyces cerivisiae*", The Journal of Biological Chemistry, 259(9):5745-5751, (1984).

Matthews et al., "Isolation of immunodominant antigens from sera of patients with systemic candidiasis and characterisation of serological response to *Candida albicans*", Journal of Clinical Microbiol., 25(2):230-237, (1987).

Matthews et al., "Characterisation and cellular localisation of immunodominant 47 KDa antigen of *Candida albicans*", Journal of Medical microbiology, 27:227-232, (1988).

Neale et al., "The immunochemical characterisation of circulating immune complex constituents in *Candida albicans* osteomyelitis by isoelectric focusing, immunoblot and immunoprint", Aust. NZ, J. Med., 17:2011-208, (1987).

Matthews et al., "Diagnosis of Systemic Candidiasis by an Enzyme-Linked Dot Immunobinding Assay for a Circulating Immunodominant 47-kilodalton Antigen", J. Clin. Microbial, 26(3):459-463, (1988).

Dragon et al., "The Genome of *Trypanosoma cruzi* Contains a Constitutively Expressed, Randomly Arranged Multicopy Gene Homologous to a Major Heat Shock Protein", Mol. Cell. Biol. 7(3):1271-1275, (1987).

Young, R. A. et al., Proc. Nat. Acad. Sci., 80:1194-1198, (1983).

Lewcock, Anna, Quality, safety issues block Novartis' antifungal approval, http://www.in-pharmatechnologist.com/news/printNewsBis.asp?id=72292, p. 1-2, (2006).

Corrected version of European Search Report for Application No. EP 07075188 dated Sep. 17, 2007.

Strockbine et al., "Identification and molecular weight characterization of antigens from *Candida albicans* that are recognized by human sera", Infections and Immunity, vol. 43, pp. 715-721, (1984).

Franklyn et al., "An immunodominant antigen of *Candida albicans* shows homology to the enzyme enolase", Immunol. Cell Biol., 68, pp. 173-178, (1990).

European Extended Search Report dated Dec. 10, 2008 for EP 07075857.8.

Burton, D.R. Proceedings of National Acad. Sciences USA, 1991, pp. 11120-11123.

Orlandi et al., Proceedings of National Acad. Sciences USA, 1991, pp. 11120-11123.

Winter, G. et al., Nature, vol. 349, 1991, pp. 293-299.

Huse et al., Science vol. 256, 1989, pp. 1275-1281.

Maddox et al., J. Exp. Med. vol. 158, 1983, pp. 1211-1226.

Radding, J.A. et al., Antimicrob. Agents Chemo. Ther, vol. 42, No. 5, 1998, pp. 1187-1194.

Broad Institute. Coccidioides Group: "Project Info" [Online] Retrieved from the Internet on Nov. 6, 2008: URL:http://www.broad.mit.edu/annotation/genome/coccidioides_group/Info.html>.

Polonelli L et al.,"The efficacy of acquired humoral and cellular immunity in the prevention and therapy of experimental fungal infections", Medical Mycology, Oxford, GB, vol. 38, No. Suppl. 01, Dec. 30, 2000, pp. 281-292.

Honegger, H. et al., "Yet another numbering scheme for immunoglobulin variable domains: an automatic modeling and analysis tool", J. Mol. Biol., 309, pp. 657-670 (2001).

Broad Institute, Data Coccidioides Group: "C. Immitis RS: CIMG_04729-Heat S" [Online] Retrieved from the Internet on Nov. 6, 2008]: URL:http://www.broad.mit.edu/annotation/genome/coccidioides_group/GeneDetails.html>.

Anonymous: "Mycograb", Internet article, [online], retrieved from URL: http://web.archive.org/web/20060616021547, Jun. 16, 2006; http://neutecpharma.com/mycograb.html, Sep. 9, 2008.

International Search Report PCT/EP2008/055087 dated Oct. 27, 2009.

Dolezai, O et al., "ScFv multimers of the anti-neuraminidase antibody NC10: shortening of the linker in single-chain Fv fragment assembled in $V_L$ lo $V_H$ orientation drives the formation of dimmers, trimers, tetramers and higher molecular mass multimers", Protein Engineering, vol. 13, No. 8, pp. 565-574, (2000).

Rowlands, H et al., "Human Recombinant Antibody Against *Candida*", The Pediatric Infectious Disease Journal, vol. 25, No. 10, pp. 959-960, (2006).

Nooney L et al., "Evaluation of Mycograb®, amphotericin B, caspofungin, and fluconazole in combination against *Cryptococcus neoformans* by checkerboard and time-kill methodologies", Diagnostic Microbiology and Infectious Disease, vol. 51, pp. 19-29, (2005).

Pachl J et al., "A Randomized, Blinded, Multicenter Trial of Lipd-Associated Amphotericin B Alone versus in Combination with an Antibody-Based Inhibitor of Heat Shock Protein 90 in Patients with Invasive Candidiasis", Mycograb and Invasive Candidiasis, vol. 42, pp. 1404-1413, (2006).

Burnie J et al., "Genetically recombinant antibodies: new therapeutics against candidiasis", Expert Opin. Biol. Ther. vol. 4, No. 2, pp. 233-241, (2004).

Matthews R et al., "Recombinant antibodies: a natural partner in combinatorial antifungal therapy", Vaccine, vol. 22, pp. 865-871, (2004).

Hodgetts, S et al., "Efungumab and caspofungin: pre-clinical data supporting synergy", Journal of Antimicrobial Chemotherapy, vol. 61, pp. 1132-1139, (2008).

Herbrecht R et al., "Mycograb for the treatment of invasive candidiasis", Clin Infect Dis., vol. 43, No. 8, pp. 1083-1084, (2006).

Excerpts from Briefing Book presented to Paul Ehrlich Institute (PEI) Jul. 2008. Version Jun. 19, 2008, pp. 8-9.

Questions and Answers on Recommendation for the Refusal of the Marketing Authorisation for Mycograb, European Medicines Agency, London, Nov. 16, 2006, pp. 1-2.

Semighini C et al., "Dynamic duo takes down fungal villains", PNAS, vol. 106, No. 9, pp. 2971-2972, (2009).

Cowen L et al., "Harnessing Hsp90 function as a powerful, broadly effective therapeutic strategy for fungal infectious disease", PNAS, (2008).

Karwa, R et al., "Efungumab: A Novel Agent in the Treatment of Invasive Candidiasis", The Annals of Pharmacotherapy, vol. 43, pp. 1818-1823, (2009).

\* cited by examiner

1: MWM Protein plus
3: IB_SOL w urea, n-r
4: REF_IM w urea, n-r 1:10
5: REF_IM w urea, n-r 1:50
6: REF_END w urea, n-r 1:10
7: REF_END w urea, n-r 1:50
8: IB_SOL w NLS, n-r
9: IB_SOL w urea, r
10: REF_IM w urea, r 1:10
11: REF_IM w urea, r 1:50
12: REF_END w urea, r 1:10
13: REF_END w urea, r 1:50
14: IB_SOL w NLS, r 1: MWM Protein_plus  2: Reference Biomeva
3: MYC 118, r        10: MYC 118, n-r
4: MYC 119; r        11: MYC 119 n-r
5: MYC 130; r        12: MYC 133 n-r
6: MYC 133; r        13: MYC 134 n-r
7: MYC 134; r        14: MYC 135 n-r
8: MYC 135; r        15: MYC 137 n-r
9: MYC 137, r        16: MYC 130 n-r 1: MWM Protein plus
2: MYC 106, origami r9: MYC 106, n-r
3: MYC 123; r10: MYC 123 n-r
4: MYC 136; r11: MYC 136 n-r
5: MYC 138; r12: MYC 138 n-r
6: MYC 139; r13: MYC 139 n-r
7: MYC 140; r14: MYC 140 n-r

ANTIBODY MOLECULES AND NUCLEIC ACIDS

This application claims benefit of EP Application No. 07107140.1, filed Apr. 27, 2007 and EP Application No. 07113353.2, filed Jul. 27, 2007, which in their entirety are herein incorporated by reference.

The present invention relates to novel antibody molecules specifically binding to fungal stress protein hsp90, nucleic acids encoding such peptides and pharmaceutical compositions and uses thereof.

An antibody fragment binding to the hsp90 fungal stress protein as well as therapeutic uses of it has been described e.g. in WO01/76627 or WO05/102386. The antibody fragment, also known as Mycograb® (Efungumab), is a fusion protein comprising the $V_H$ and $V_L$ domains of immunoglobulin connected by a linker peptide. Such antibody fragments are also known as "single chain variable fragment" (scFv). Mycograb® is produced by fermentation in *E. coli* in the form of inclusion bodies, which are extracted from the cell mass, refolded and subsequently purified by chromatographic steps under denaturing conditions. Characterization studies performed under native conditions have indicated that the efungumab protein has a tendency to form multimers or aggregates (the terms "multimers" and "aggregates" are used interchangeably herein). Such aggregates, in particular high molecular weight aggregates, may not be desirable for therapeutic uses. Thus, for therapeutic uses it may be desirable to eliminate or reduce the high molecular weight aggregates or to control aggregation such that the number of momomers, which a majority of such aggregates contain, are in a certain range, e.g. between 10 and 100 monomers, such as e.g. between 11 and 73 or 26 and 57 monomers.

The present invention now provides improved scFv peptides binding to hsp90 fungal stress protein, which have advantageous properties with respect to e.g. folding properties and/or formation of aggregates. The peptides of the invention are thus particularly useful for therapeutic uses.

According to one aspect of the present invention, there is provided a scFv peptide comprising a $V_H$ domain and a $V_L$ domain linked by an amino acid spacer, wherein the $V_H$ domain comprises a sequence with at least 80% sequence identity to the sequence of SEQ ID NO. 64 and the $V_L$ domain comprises a sequence with at least 80% sequence identity to the sequence of SEQ ID NO. 66 and wherein the scFv peptide comprises an additional feature selected from the group consisting of:
  (a) a substitution or deletion of an amino acid in the $V_H$ domain at a position corresponding to that selected from the group consisting of: $C_{28}$, $I_{29}$, $H_{68}$, $N_{85}$, $C_{97}$ and combinations thereof;
  (b) a substitution or deletion of an amino acid in the $V_L$ domain at a position corresponding to that selected from the group consisting of: $V_2$, $V_3$, $F_{10}$, $F_{14}$, $A_{39}$, $N_{76}$ and combinations thereof;
  (c) the amino acid spacer comprises the sequence $(GGGGS)_n$ wherein n is between 4 and 6;
  (d) the $V_H$ domain further comprises an N-terminal pelB signal sequence comprising the sequence of SEQ ID NO. 68 or a sequence having at least 80% sequence identity thereto;
  (e) the $V_L$ domain is located at the N-terminal end of the $V_H$ domain; and
  (f) combinations of features (a) to (e).

It is preferred that the $V_H$ domain comprises a sequence with at least 90%, 95%, 99% or 100% identity to the sequence of SEQ. ID NO. 64. It is also preferred that the $V_L$ domain comprises a sequence with at least 90%, 95%, 99% or 100% identity of the sequence of SEQ. ID NO. 66. It is to be understood that the additional feature is present irrespective of the level of sequence identity. For example, if the additional feature is a substitution of the amino acid at position $C_{28}$ then this substitution is present even in embodiments where the $V_H$ domain comprises a sequence with only 80% sequence identity to SEQ. ID NO. 64.

Conveniently, the substitution of the amino acid in the $V_H$ domain is selected from the group consisting of: $C_{28}Y$, $C_{28}S$, $I_{29}S$, $H_{68}R$, $N_{85}S$, $C_{97}Y$, $C_{97}S$ and combinations thereof. The substitution $C_{28}Y$ is particularly preferred.

Advantageously, the substitution of the amino acid in the $V_L$ domain is selected from the group consisting of: $V_2I$, $V_3Q$, $F_{10}S$, $F_{14}S$, $A_{39}K$, $N_{76}S$ and combinations thereof. Preferably, the scFv peptide comprises an amino acid sequence selected from the group consisting of SEQ ID NO. 8, 10, 12, 14, 16, 18, 20, 22, 24, 26, 28, 30, 32, 34, 36, 38, 40, 42, 44, 46, 48, 50, 52, 54, 56, 58, 60 and 62 wherein Xaa denotes an amino acid residue other than cysteine and wherein the N-terminal methionine residue may optionally be cleaved off. It is preferred that Xaa denotes a tyrosine residue.

In one embodiment Xaa is Tyr (Y). In another embodiment Xaa is Ala (A), Leu (L), Ile (I), Val (V), Pro (P) or Met (M); in yet another embodiment Xaa is Phe (F) or Try (W); in yet another embodiment Xaa is Gly (G); in yet another embodiment X is Ser (S) or Thr (T); in yet another embodiment Xaa is Glu (E) or Asp (D); in yet another embodiment Xaa is Gln (Q) or Asn (N); in yet another embodiment Xaa is Arg (R), Lys (K) or His (H).

Preferably the scFv peptide further comprises a purification tag, more preferably a sequence of 6 histidine residues at the C-terminus.

In accordance with another embodiment of the present invention, there is provided a scFv peptide consisting of, or consisting essentially of, an amino acid sequence as set forth SEQ ID NO. 8, 10, 12, 14, 16, 18, 20, 22, 24, 26, 28, 30, 32, 34, 36, 38, 40, 42, 44, 46, 48, 50, 52, 54, 56, 58, 60 and 62 wherein said peptides may optionally comprise a purification tag such as e.g. a His-Tag (e.g. as set forth in SEQ ID NO. 10, 22 or 34).

The purification Tags typically do not contribute to the therapeutic effect of the molecule and may therefore be removed after purification of the scFv fragments of the present invention.

In accordance with another aspect of the present invention, there is provided a scFv peptide comprising an amino acid sequence as set forth in SEQ ID NO. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 and 62. In one embodiment, there is provided a scFv peptide consisting of, or consisting essentially of, an amino acid sequence as set forth SEQ ID NO. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 and 62 wherein said peptides may optionally also comprise a purification tag such as e.g. a His-Tag (e.g. as set forth in SEQ ID NO. 2, 4 or 20).

As readily appreciated by the skilled person, the first Met residue of the peptides of the present invention may be also cleaved off in vivo, e.g. by *E. coli* MAP (methionine amino peptidase) if expressed in *E. coli*.

The scFv peptides of the present invention comprise two domains linked by an amino acid spacer (the terms "spacer" and "linker" are used interchangeably), e.g. having the amino acid sequence $(GGGGS)_n$ wherein n is an integer from 1 to 12, e.g. 1, 2, 3, 4 or 5. One of the domains, designated as $V_H$, corresponds to the heavy chain part of the antibody fragment (corresponding e.g. to amino acid residues 2 to 122 in the scFv fragment of amino acid sequence set forth in SEQ ID NO. 2 and SEQ ID NO. 30, or amino acid residues 132 to 152 in SEQ ID NO. 32). The other domain, designated as $V_L$, corresponds to the light chain part of the antibody fragment (corresponding e.g. to amino acid residues 138 to 246 in SEQ ID NO. 2, or amino acid residues 138-246 in SEQ ID NO. 12, or amino acid residues 2 to 110 in SEQ ID NO. 32). The VH or the VL domain may be located at the N-terminus of the scFv peptides of the present invention, i.e. the molecules may be linked as follows: VH-linker-VL or VL-linker-VH.

The optional pelB signal sequence results in subcellular localisation of the peptide to the periplasmic membrane, when expressed in *E. coli*, in order to improve solubility of the peptide.

In one embodiment, there is provided a scFv fragment comprising an amino acid sequence as set forth in SEQ ID NO. 30 or 32. In another embodiment, there is provided a scFv peptide consisting of, or consisting essentially of, an amino acid sequence as set forth SEQ ID NO. 30 or 32 wherein said peptides may optionally also comprise a purification tag such as e.g. a His-Tag.

In one aspect, the present invention provides scFv fragments comprising a VH and VL domain and a linker according to the present invention (e.g. as set forth in SEQ ID NO. 2, 4, 6, 8, 10, 12, 14, 16, 18, 20, 22, 30, 32 or 34) having at least one amino acid substituted at one or more of the following positions: C29X, I30X, H69X, N86X, C98X, V139X, V140X, F147X, F151X, A176X, N213X, wherein X denotes an amino acid other than as set forth in SEQ ID NO. 2 (the numbering is as set forth in SEQ ID NO. 2 and corresponding amino acid positions in other mutants can be easily determined). In a preferred embodiment, the present invention provides scFv fragments having at least one of the following amino acid substitution: C29Y or C29S, I30S, H69R, N86S, C98Y or C98S, V139I, V140Q, F147S, F151S, A176K, N213S. It is to be appreciated that numbering of amino acids in relation to this aspect includes the N-terminal methionine residue.

In one embodiment, there is provided a scFv fragment comprising an amino acid sequence as set forth in SEQ ID NO. 24, 26 or 28. In another embodiment, there is provided a scFv peptide consisting of, or consisting essentially of, an amino acid sequence as set forth SEQ ID NO. 24, 26 or 28 wherein said peptides may optionally also comprise a purification tag such as e.g. a His-Tag.

The peptides of the present invention are useful as therapeutics. Accordingly, in one aspect of the present invention, there is provided a pharmaceutical composition comprising a scFv peptide according to the present invention, e.g. comprising an amino acid sequence as set forth in SEQ ID NO. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 and 62 wherein Xaa is defined as above, in combination with a pharmaceutically acceptable excipient, diluent or carrier. Details of suitable excipients are provided in *Remington's Pharmaceutical Sciences and US Pharmacopoeia*, 1984, Mack Publishing Company, Easton, Pa., USA. Exemplary excipients include pharmaceutical grade (Ph Eur) Urea and L-Arginine (Ph Eur). For example, a typical formulation of an scFv peptide of the invention is 10 mg of pure scFv peptide, 150 mg of pharmaceutical grade (Ph Eur) Urea and 174 mg L-Arginine (Ph Eur) reconstituted in 5 ml water.

An scFv peptide or a pharmaceutical composition of the invention may be administered in a dosage in the range of 0.1 to 10 mg/kg body weight of the patient. A dosage in the range 0.5 to 5 mg/kg body weight is preferred, with a dosage of around 1 mg/kg being particularly preferred. The pharmaceutical composition may be administered orally.

The peptides of the present invention are useful in the treatment of fungal infections e.g. as disclosed in WO01/76627 or WO05/102386 each of which is hereby incorporated by reference. For example, the peptides of the present invention are useful in the treatment of systemic fungal infections such as invasive candidiasis or invasive aspergillosis or invasive meningitis e.g. virulent *Candida* species *C. albicans*, *C. tropicalis* and *C. krusei* and the less virulent species *C. parapsilosis* and *Torulopsis glabrata*. The peptides of the present invention are also useful in the treatment of infections by *Candida, Cryptococcus, Histoplasma, Aspergillus, Torulopsis, Mucormycosis, Blastomycosis, Coccidioidomycosis, Paracoccidioidomycosis* organism or *malaria*. Accordingly, the present invention provides a method of treating a patient with a fungal infection comprising administering to the patient an effective amount of a scFv peptide of the present invention, e.g. comprising an amino acid sequence as set forth in SEQ ID NO. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 and 62 wherein Xaa is defined as above. The N-terminal Met may optionally be cleaved off.

The peptides of the present invention are particularly useful for combination therapies. Accordingly, in another aspect, the present invention provides a composition or a combined preparation comprising a scFv peptide of the present invention, e.g. comprising an amino acid sequence as set forth in SEQ ID NO. 2, 4, 6, 8, 10, 12, 14, 16, 18 20, 22, 24, 26, 28, 30, 32, 34, 36, 38, 40, 42, 44, 46, 48, 50, 52, 54, 56, 58, 60 and 62 (the N-terminal Met may optionally be cleaved off), wherein Xaa is defined as above, and a antifungal agent such as e.g. a polyene antifungal or a echinocandin antifungal or an azole antifungal. Examples of antifungals useful as combination partners of scFv peptides of the present invention include e.g. amphotericin B, derivatives of amphotericin B such as AmBisome, amphotericin-B lipid complex (Abelcet), amphotericin-B colloidal dispersion (Amphocil) and amphotericin-B intralipid emulsion; nystatin; 5-fluorocytosine; caspofungin, anidulafungin, micafungin, LY303366; azoles such as isavuconazole, voriconazole, itraconazole, fluconazole, miconazole, ketoconazole, posaconazole, anidulafungin, micafungin, griseofulvin, terbinafine. Though such combination may be a fixed dose combination, generally, the scFv peptide and its combination partner are not packaged as fixed dose combinations. The combined preparations of the present invention may be for simultaneous, separate or sequential use in the treatment of fungal infections. The peptides of the present invention may also be used in combination with more than one antifungal agent, e.g. with amphotericin B and 5-fluorocytosine, a fingin and Amphotericin B or an echinocandin plus azole.

In another embodiment, the present invention provides a method of treating a patient with a fungal infection comprising administering to the patient an effective amount of a scFv peptide of the present invention, e.g. comprising an amino acid sequence as set forth in SEQ ID NO. 2, 4, 6, 8, 10, 12, 14, 16, 18, 20, 22 24, 26, 28, 30, 32, 34, 36, 38, 40, 42, 44, 46, 48, 50, 52, 54, 56, 58, 60 and 62 (the N-terminal Met may optionally be cleaved off), wherein Xaa is defined as above, and at least one of the antifungal agents described above. Preferred combination partners are amphotericin B or derivatives of amphotericin B, caspofungin, anidulafungin, micafungin, voriconazole, itraconazole. The combination partners may be administered simultaneously, separately or sequentially.

In one embodiment of the present invention, the fungus causing the infection is resistant or partially resistant against an antifungal combination partner of the peptides of the invention.

The peptides of the present invention are also useful in the treatment of cancer, or a condition involving raised levels of TNFα and/or IL-6 such as autoimmune diseases or sepsis e.g. as disclosed in WO06/003384 or WO07/077,454 (PCT/GB2007/000029) each of which is hereby incorporated by reference. For instance, the peptides of the present invention are useful in the treatment of leukemia such as e.g. lymphoid (lymphocytic) leukaemia (CLL), acute myeloid (myeloblastic) leukaemia (AML), acute lymphoid (lymphoblastic) leukaemia (ALL), chronic myeloid leukaemia (CML), carcinoma of the breast, carcinoma of the colon, prostate, multiple myeloma; or for the treatment of sepsis targeting human hsp90 (WO07/077,454). Accordingly, the present invention provides a method of treating a patient with a cancer disease or a condition involving raised levels of TNFα and/or IL-6 (e.g. autoimmune disease, SIRS or sepsis) comprising administering to the patient an effective amount of a scFv peptide of the present invention, e.g. comprising an amino acid sequence as set forth in SEQ ID NO. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 and 62 (the N-terminal Met may optionally be cleaved off), wherein Xaa is defined as above.

In some embodiments, the autoimmune disease is Crohn's disease, rheumatoid arthritis, ulcerative colitis or systemic lupus erythermatosus.

The peptides of the present invention are useful for combination therapies with anticancer agents. Examples of suitable anticancer agents include doxorubicin, daunorubicin, epirubicin, herceptin, docetaxel, cisplatin, imatinib (Gleevec®), paclitaxel, cytarabine or hydroxyurea. Accordingly, the present invention provides a composition or a combined preparation comprising a scfv peptide of the present invention, e.g. comprising an amino acid sequence as set forth in SEQ ID NO. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 and 62 (the N-terminal Met may optionally be cleaved off), wherein Xaa is defined as above, and a anticancer agent selected from the group consisting of doxorubicin, daunorubicin, epirubicin, herceptin, docetaxel, cisplatin, imatinib, paclitaxel and hydroxyurea. Also provided are methods of treating a patient with a cancer disease comprising administering to the patient in need an effective amount of a scFv of the present invention, e.g. peptide comprising an amino acid sequence as set forth in SEQ ID NO. 2, 4, 6, 8, 10, 12, 14, 16, 18 20, 22, 24, 26, 28, 30, 32, 34, 36, 38, 40, 42, 44, 46, 48, 50, 52, 54, 56, 58, 60 and 62 (the N-terminal Met may optionally be cleaved off), wherein Xaa is defined as above, and at least one of the anticancer agent selected from the group consisting of doxorubicin, daunorubicin, epirubicin, herceptin, docetaxel, cisplatin, imatinib, paclitaxel and hydroxyurea.

In accordance with another aspect of the present invention, there are provided improved nucleic acid molecules encoding scFv peptides as described and improved nucleic acid constructs which are particularly useful for expressing such scFv peptides e.g. in *E. coli*. The nucleic acid constructs of the present invention for instance lead to improved expression of the scFv peptides in *E. coli*, e.g. with respect to homogeneity and titer of the expressed scFv peptide.

Preferably, the nucleic acid molecule further comprises the sequence $(taa)_n$ located at the 3' end of the sequence encoding the scFv peptide wherein n is 1 or 2.

According to another aspect of the present invention, there is provided a nucleic acid molecule comprising a sequence encoding a $V_H$ domain comprising a sequence having at least 80% sequence identity to the sequence of SEQ ID NO. 64 and a $V_L$ domain comprising a sequence having at least 80% sequence identity to the sequence of SEQ ID NO. 66 and further comprising the sequence $(taa)_n$ located at the 3' end of the sequence encoding the $V_H$ or $V_L$ domains wherein n is 1 or 2. The provision of multiple stop codons at the 3' terminus avoids erroneous read-through events.

In another aspect the present invention provides a nucleic acid molecule, e.g. a DNA or RNA molecule, comprising a nucleotide sequence as set forth in SEQ ID NO. 3, 5, 7, 9, 11, 13, 15, 17, 19, 21, 23, 25, 27, 29, 31, 33, 35, 37, 39, 41, 43, 45, 47, 49, 51, 53, 55, 57, 59, or 61 wherein nnn denotes a codon coding for an amino acid other than Cys. For instance, in one embodiment, nnn may code for Tyr such as e.g. TAT. In another aspect, the present invention provides a nucleic acid molecule comprising a nucleotide sequence as set forth in SEQ ID NO. 1, 3, 5, 11, 15 or 19. As appreciated by the skilled person, nucleic acid sequences can be readily modified without altering the encoded amino acid sequence. Nucleic acid molecules based on a nucleotide sequence comprising a nucleotide sequence as set forth in SEQ ID NO. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, or 61. with one or more (e.g. up to 10, 20, 50 or 100) such silent mutations are also comprised within the scope of the present invention. Further encompassed are nucleic acid molecules which have (i) at least 80% identity, preferably at least 90%, 95%, 99% or 100% identity to SEQ. ID NO. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, or 61; or (ii) hybridize under high stringency conditions to the nucleic acid molecules having a sequence as set forth in SEQ ID NO. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, or 61. The term high stringency conditions is readily understood by the skilled person and may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). Suitable ranges of such stringency conditions for nucleic acids of varying compositions are described in Krause and Aaronson (1991) Methods in Enzymology, 200:546-556.

In one embodiment, the present invention provides a vector molecule comprising a nucleotide sequence of a nucleic acid molecule of the invention, e.g. as set forth in SEQ ID NO. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, or 61. Preferably, such vector molecule is suitable for expressing the nucleic acid molecules as set forth in SEQ ID NO. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, or 61. in e.g. *E. coli*. Suitable expression vectors are readily known to the skilled person. An example of suitable vector includes for instance pGEX or pET. Another embodiment provides a host cell, e.g. *E. coli*, comprising such a vector molecule.

In another embodiment there is provided a method for producing a scFv peptide of the present invention, e.g. comprising an amino acid sequence as set forth in SEQ ID NO. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 or 62 (the N-terminal Met may optionally be cleaved off), wherein Xaa is defined as above which comprises culturing a host cell having incorporated therein an expression vector containing under control of suitable transcriptional control elements a nucleic acid sequence of a nucleic acid molecule of the invention e.g. as described in SEQ ID NO. 3, 5, 7, 9, 11, 13, 15, 17, 19, 21, 23, 25, 27, 29, 31, 33, 35, 37, 39, 41, 43, 45, 47, 49, 51, 53, 55, 57, 59, or 61 under conditions sufficient for expression of said peptides in the host cell, e.g. *E. coli*, thereby causing the production of said peptide; and recovering the peptide produced by said cell.

The percentage "identity" between two sequences is determined using the BLASTP algorithm version 2.2.2 (Altschul, Stephen F., Thomas L. Madden, Alejandro A. Schäffer, Jinghui Zhang, Zheng Zhang, Webb Miller, and David J. Lipman (1997), "Gapped BLAST and PSI-PLAST: a new generation of protein database search programs", Nucleic Acids Res. 25:3389-3402) using default parameters. In particular, the BLAST algorithm can be accessed on the Internet using the URL http://www.ncbi.nlm.nih.gov/blast/.

BRIEF DESCRIPTION OF THE SEQUENCE LISTINGS

Figure 1:
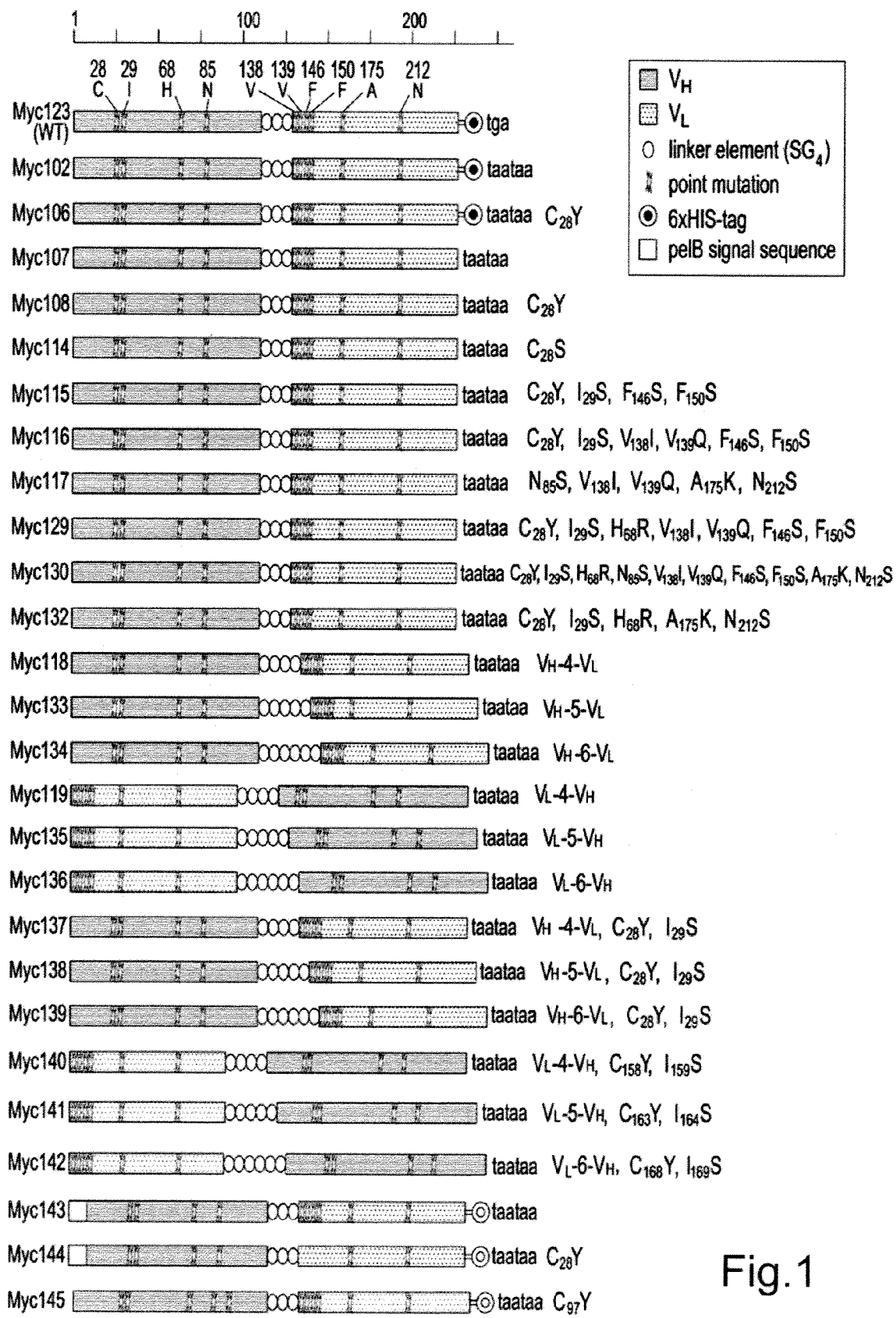
FIG. 1 is a diagram showing schematically the sequence of the wild type Mycograb scFv peptide and Mycograb mutants. Stop codons of the nucleic acid molecules encoding the respective peptides are also shown at the C-terminal end.

SEQ ID NO. 1 is Myc123
SEQ ID NO. 2 is the peptide sequence encoded by SEQ ID NO. 1
SEQ ID NO. 3 is Myc102, Mycograb-6H-TAA
SEQ ID NO. 4 is the peptide sequence encoded by SEQ ID NO. 3
SEQ ID NO. 5 is Myc101, Mycograb-TAA
SEQ ID NO. 6 is the peptide sequence encoded by SEQ ID NO. 5
SEQ ID NO. 7 is MycC29X-TAA, e.g.: Myc105, MycC29Y-TAA
SEQ ID NO. 8 is the peptide sequence encoded by SEQ ID NO. 7

SEQ ID NO. 9 is MycC29X-6H-TAA, e.g.: Myc106, MycC29Y-6H-TAA, Myc113, MycoC29S-6H-TAA
SEQ ID NO. 10 is the peptide sequence encoded by SEQ ID NO. 9
SEQ ID NO. 11 is Myc107, Myco-4-TAA
SEQ ID NO. 12 is the peptide sequence encoded by SEQ ID NO. 11
SEQ ID NO. 13 is MycoC29X-4-TAA, e.g.: Myc108, MycoC29Y-4-TAA; Myc114, MycoC29S-4-TAA
SEQ ID NO. 14 is the peptide sequence encoded by SEQ ID NO. 13
SEQ ID NO. 15 is Myc109, N-Myco-4-TAA
SEQ ID NO. 16 is the peptide sequence encoded by SEQ ID NO. 15
SEQ ID NO. 17 is N-MycoC29X-4-TAA, e.g.: Myc 10, N-MycoC29Y-4-TAA
SEQ ID NO. 18 is the peptide sequence encoded by SEQ ID NO. 17
SEQ ID NO. 19 is Myc111, N-Myco-6H-TAA
SEQ ID NO. 20 is the peptide sequence encoded by SEQ ID NO. 19
SEQ ID NO. 21 is N-MycoC29X-6H-TAA, e.g.: Myc112, N-MycoC29Y-6H-TAA
SEQ ID NO. 22 is the peptide sequence encoded by SEQ ID NO. 21
SEQ ID NO. 23 is Myc115, MycYSSS
SEQ ID NO. 24 is the peptide sequence encoded by SEQ ID NO. 23
SEQ ID NO. 25 is Myc116, MycYSIQSS
SEQ ID NO. 26 is the peptide sequence encoded by SEQ ID NO. 25
SEQ ID NO. 27 is Myc117, MycSIQKS
SEQ ID NO. 28 is the peptide sequence encoded by SEQ ID NO. 27
SEQ ID NO. 29 is Myc118, VH-2Bam-2VL
SEQ ID NO. 30 is the peptide sequence encoded by SEQ ID NO. 29
SEQ ID NO. 31 is Myc119, VL-2Bam-2VH
SEQ ID NO. 32 is the peptide sequence encoded by SEQ ID NO. 31
SEQ ID NO. 33 is Myc145, MycC98X-6H-TAA
SEQ ID NO. 34 is the peptide sequence encoded by SEQ ID NO. 33
SEQ ID NO. 35 is Myc129 (MycYSRIQSS)
SEQ ID NO. 36 is the peptide sequence encoded by SEQ ID NO. 35
SEQ ID NO. 37 is Myc130 (MycYSRSIQSSKS)
SEQ ID NO. 38 is the peptide sequence encoded by SEQ ID NO. 37
SEQ ID NO. 39 is Myc133
SEQ ID NO. 40 is the peptide sequence encoded by SEQ ID NO. 39
SEQ ID NO. 41 is Myc134
SEQ ID NO. 42 is the peptide sequence encoded by SEQ ID NO. 41
SEQ ID NO. 43 is Myc135
SEQ ID NO. 44 is the peptide sequence encoded by SEQ ID NO. 43
SEQ ID NO. 45 is Myc136
SEQ ID NO. 46 is the peptide sequence encoded by SEQ ID NO. 45
SEQ ID NO. 47 is Myc137
SEQ ID NO. 48 is the peptide sequence encoded by SEQ ID NO. 47
SEQ ID NO. 49 is Myc138
SEQ ID NO. 50 is the peptide sequence encoded by SEQ ID NO. 49
SEQ ID NO. 51 is Myc139
SEQ ID NO. 52 is the peptide sequence encoded by SEQ ID NO. 51
SEQ ID NO. 53 is Myc140
SEQ ID NO. 54 is the peptide sequence encoded by SEQ ID NO. 53
SEQ ID NO. 55 is Myc141
SEQ ID NO. 56 is the peptide sequence encoded by SEQ ID NO. 55
SEQ ID NO. 57 is Myc142
SEQ ID NO. 58 is the peptide sequence encoded by SEQ ID NO. 57
SEQ ID NO. 59 is Myc143
SEQ ID NO. 60 is the peptide sequence encoded by SEQ ID NO. 59
SEQ ID NO. 61 is Myc144
SEQ ID NO. 62 is the peptide sequence encoded by SEQ ID NO. 61
SEQ ID NO. 63 is the nucleotide sequence encoding the heavy chain of the wild type Myc123 scFv peptide.
SEQ ID NO. 64 is the peptide sequence encoded by SEQ ID NO. 63
SEQ ID NO. 65 is the nucleotide sequence encoding the light chain of the wild type Myc123 scFv peptide.
SEQ ID NO. 66 is the peptide sequence encoded by SEQ ID NO. 65.
SEQ ID NO. 67 is the nucleotide sequence of the pelB signal sequence.
SEQ ID NO. 68 is the peptide sequence encoded by SEQ ID NO. 67.
SEQ ID NO. 69 is the epitope from Candidal hsp90 for which the scFv peptide of SEQ ID NO. 2 (Mycograb) is specific.
SEQ ID NO. 70 is the epitope of a scrambled peptide used in the binding assay of Example 2.

EXPERIMENTAL

Example 1

E. coli host cells are transformed with the expression vector and cultivated in submers culture. At suitable OD600, expression of scFv is induced by derepression or activation of the inducible promorter (i.e. tac, trc or T7-lac promoter). This induction leads to accumulation of scFv in the host cell, resulting in production of insoluble inclusion bodies mainly made of aggregated scFv. After a suitable expression period, cells are harvested by centrifugation and disrupted. The insoluble inclusion bodies are subsequently isolated by gravimetric means.

The DNA sequences set forth in SEQ ID NO. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61 are inserted into an expression vector suitable for E. coli (i.e. pET). The protein is expressed in a Escherichia coli host and then purified by affinity chromatography. Standard molecular biology protocols are employed (see, for example, Harlow & Lane, supra; Sambrook, J. et al., 1989, Molecular Cloning: A Laboratory Manual, 2nd Edition, Cold Spring Harbor Laboratory Press, Cold Spring Harbor, N.Y.; Sambrook, J. & Russell, D., 2001, Molecular Cloning: A Laboratory Manual, 3rd Edition, Cold Spring Harbor Laboratory Press, Cold Spring Harbor).

After intracellular expression the scFv peptides are accumulated in the form of inclusion bodies within the E. coli cells. For purification, inclusion bodies are isolated and the product is extracted by solubilization and refolding. Purification to over 95% purity is achieved by ion exchange chromatography and immobilized metal affinity chromatography (IMAC).

Example 2

ELISA Activity Assay

1. Summary

The binding activity of MYC123 ("wild type" Mycograb) and mutant Mycograb peptides was detected in an ELISA using the peptide epitope of hsp 90 as antigen. Mycograb or mutant Mycograb became bound to biotinylated peptide, which in turn was bound to streptavidin-coated microtitre plates. A scrambled peptide was used as a control sequence. Detection was accomplished using a peroxidase conjugated anti-His antibody, which binds to the His region of the MYC 123 protein. The peroxidase reacted with the ABTS substrate to produce a green substance, the absorption of which was measured at 405 nm. The absorption at 405 nm is proportional to the activity of MYC123 in the solution. The activity was determined from the 6-point calibration curve for a reference standard and was indicated as % activity compared with the reference.

Figure 2:
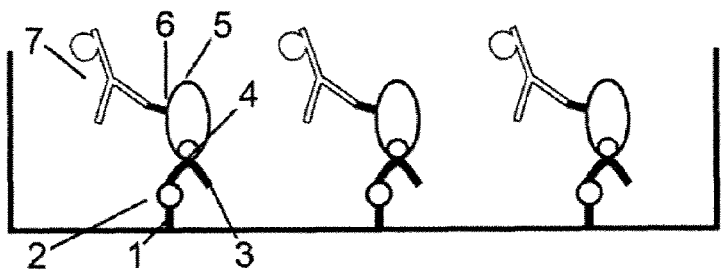
FIG. 2 is a diagram showing the principle of the ELISA assay of Example 2.

The principle of the ELISA is depicted in FIG. 2 in which Streptavidin 1 is coated on a plate and is bound to biotin 2. The biotin 2 is, in turn, bound to the Hsp 90 peptide 3 which is located in the Hsp90 binding site 4 of the MYC123 scFv peptide 5. The scFv peptide 5 has a His tag 6 to which becomes bound the Anti-His-Peroxidase detection antibody 7.

2. Principle and Source of Procedure

The ELISA utilised was a direct detection assay where Mycograb or mutant Mycograb was captured using a streptavidin surface microplate coated with a biotinylated antigenic peptide (Biotin-NKILKVIRKNIVKK—epitope sequence from candidal Hsp90). The presence of Mycograb or mutant Mycograb was then detected using an anti-His tag antibody conjugated to horse radish peroxidase. ABTS, a substrate for the horse radish peroxidise, was then added to the wells, and the concentration of Mycograb present was proportional to the absorbance measured at 405 nm. The activity of samples of Mycograb or mutant Mycograb was determined directly from a standard curve generated using the pre-existing Mycograb drug product reference material.

3. Materials 3.1 Equipment

Streptawell High Bind microtitre plates were supplied by Roche (Cat No. 11989685001). Assays were performed using a Bio-Rad Model 680 microplate reader. Hardware control was performed using the Microplate Manager Software version 5.2.1 (Bio-Rad, USA). Data analysis was performed using Microsoft Excel.

3.2 Chemicals and Reagents 3.2.1 Chemicals

All chemicals were of analytical grade unless otherwise stated.
Tris . . . Sigma T6791
Bovine Serum Albumin . . . Sigma A7030
Concentrated Hydrochloric acid . . . Sigma 32033-1
Phosphate Buffered Saline Tablets . . . Sigma P4417
Tween 20 . . . SigmaUltra P7949
Anti-His tag antibody HRP conjugate Sigma A7958
ABTS . . . Sigma A3219
Biotin-NKILKVIRKNIVKK (SEQ. ID NO: 69) Pepceuticals, UK
Biotin-SFKWGVTTSLSYFPK (SEQ. ID NO: 70) Pepceuticals, UK
Water, Milli-Q water 18.2MΩfiltered 0.22 μm pore size.

3.2.2 Reagents

Blocking Buffer Stock 1 (5% w/v BSA in Milli-Q water)
BSA . . . 2.5 g
Weighed out 2.5 g of BSA and added to 50 mL of Milli-Q water. Store at 4° C. for 1 week.
1M Tris Buffer pH 7.8
Tris . . . 121.24 g
Weighed out 121.24 g Tris and dissolved in 950 ml Milli-Q water with stirring. Checked and adjusted pH with drop-wise addition of Concentrated Hydrochloric Acid until pH was 7.8. Made up to 1 liter with Milli-Q water. Filtered through a 0.22 μm filter (Sartorius) and stored at room temperature for up to 1 month.
Sample Diluting Buffer (20 mM Tris pH 7.8 0.1% w/v BSA)
1 mL of 1M Tris stock solution was added to 48 ml of Milli-Q water and 1 ml of Blocking buffer Stock 1 solution. Made fresh for each experiment.
Wash Buffer (PBS+Tween 20 0.1% v/v)
Dissolved 5 PBS tablets in 900 mL of Milli-Q water, added 1 mL of Tween 20, stirred until tablets had dissolved and made up to 1000 mL with Milli-Q water. Stored at 4° C. for up to 1 week.
Blocking Buffer Stock 2 (Wash Buffer+5% w/v BSA)
BSA . . . 2.5 g
Weighed out 2.5 g of BSA and dissolved in 50 mL of Wash Buffer. Stored at 4° C. for 1 week.
Peptide Diluting Buffer (PBS+0.1% v/v Tween 20+0.1% w/v BSA)
1 mL of Blocking buffer Stock 2 was added to 49 mL of Wash buffer. Made fresh for each experiment.
Antigenic Peptide Solution
Biotin-NKILKVIRKNIVKK peptide . . . 10 mg.
A 2 mg/ml solution of the custom synthesised antigenic peptide solution was made up by weighing out 10 mg of peptide and dissolving it in 5 ml of Milli-Q water. 50-100 μl aliquots were dispensed into 1.5 ml Eppendorf tubes and stored frozen at −80° C. for up to one year.
Antigenic Peptide Working Solution (4 μg/mL Peptide in Peptide Diluting Buffer)
25 μL of Antigenic peptide solution (2 mg/mL) was added to 12.475 mL of Peptide Diluting Buffer to give a 4 μg/mL solution. Made fresh for each experiment.

3.2.3 Sample Preparation

Control Article

Resuspended 1×10 mg Mycograb reference batch (BN270603) in 5 ml of Milli-Q water, mixed gently to ensure all the powder in the vial was incorporated and dissolved. Centrifuge at 13,000 rpm for 5 minutes to remove any particulate matter. The protein concentration of this solution was then determined according to the standard UV protein concentration procedure.

Test Article

Resuspended 1×10 mg Mycograb or mutant Mycograb test material in 5 ml of Milli-Q water, and processed in an identical fashion to the Control Article.

Calibration Curve Standards

Control Article material was diluted in Sample Diluting buffer to give 5 mL of a 5 μg/mL top concentration sample. This solution was then used to generate two-fold serially diluted samples each in a final volume of 2 mL over a concentration range of 5-0.156 µg/mL.

4. Procedure

1. An aliquot of the 2 mg/ml stock solution of antigenic peptide was removed from the freezer and diluted 1:500 (25 µl peptide in 12.5 ml buffer) with PBS buffer containing 0.1% (w/v) BSA and 0.1% (v/v) Tween 20 to generate a working solution of 4 µg/ml peptide. A 96 well high bind StreptaWell plate (Roche) was coated from rows B-H with 100 µl of 4 µg/ml biotin-NKILKVIRKNIVKK peptide in 0.1% (w/v) BSA PBS-0.1% (v/v) Tween 20. 100 µl per well of 0.1% (w/v) BSA PBS-0.1% (v/v) Tween 20 were added to all wells in Row A. The plate was then stored overnight at 4° C.
2. The plate wells were then washed 3×30 sec with 200 µl of PBS 0.1% (v/v) Tween 20 buffer on a Thermo WellWash AC.
3. Mycograb and mutant Mycograb samples were prepared prior to loading by diluting down to 5 µg/ml in 20 mM Tris buffer pH 7.8, 0.1% (w/v) BSA from the resuspended Mycograb vial stock solution. Mycograb® samples were then prepared from this initial 5 µg/ml solution by serial dilution ×2 down to 0.15625 µg/ml with 20 mM Tris buffer pH 7.8, 0.1% (w/v) BSA. All the individual dilutions were performed in either 1.5 ml Eppendorf tubes (VWR Cat No 211-2139) or 7 ml Bijoux containers (VWR Cat. No. 215-0328), depending on the amount required for the experiment. 100 µl of each dilution sample was then loaded onto the plate in triplicate. A control set of blank wells containing 100 µl 20 mM Tris pH 7.8, 0.1% (w/v) BSA was also included in Row H.
4. The plate was left at room temperature for 1 hour and the wells then washed 3 times with PBS-0.1% (v/v) Tween 20 as described in step 2.
5. 100 µl of mouse monoclonal Anti-His HRP conjugate (Sigma A7058) was loaded into each well at a concentration of 1:2000 in 0.1% (w/v) BSA PBS-0.1% (v/v) Tween 20 and left for 1 hour at room temperature.
6. Wells were then washed as described above and the bound Mycograb® detected by the addition of 100 µl of ABTS® reagent. The colourimetric development was read at 405 nm with readings taken when the absorbance of the highest concentration samples in the second calibration curve reached 1.3 AU. The concentration of Mycograb® was proportional to the absorption at A405 nm.
7. The A405 nm absorbance results for the reference material were transferred into an Excel spreadsheet and a 6-point second order calibration function $y=a+bx+cx^2$ was plotted from the reference sample A405 nm minus blank versus concentration of Mycograb® in µg/ml with a correlation coefficient of $\geqq 0.99$. If an observed 'hook' effect existed, the highest concentration point was removed from the graph, leaving a 5-point calibration curve. Two individual well outliers (as determined by eye) per plate was removed from the data analysis under some circumstances, provided that there is no more than one outlier per triplicate measurement. Percentage activity was calculated using non-linear regression analysis to calculate apparent concentrations in the samples using the appropriate absorbance means.

The ELISA results obtained during the study are shown in Table 1.

TABLE 1

| | | | | Bioassay data | |
|---|---|---|---|---|---|
| | | Sample information | | ELISA | ELISA |
| No. | Sample | Sample info | Buffer composition | Site 1 [%] | Site 2 [%] |
| 1 | MYC123 WT DF.R | Wild type | 50 mM Tris, pH 9.0 | 71 | 95 |
| 2 | DP (#140602) | Wild type | 0.5 M urea, 0.2 M L-arginine pH 9.5 | 90 | 78 |
| 3 | MYC123 WT DOW.FT | Wild type | 50 mM Tris, 1 M sucrose, ~0.2% Tween20, 3 mM DTT, pH 3.0 | 135 | 130 |
| 4 | MYC123 WT DOW.FT | Wild type | 50 mM Tris, 3 mM DTT, pH 9.0 | 85 | 131 |
| 5 | MYC C28Y DF.R | C28Y | 50 mM Tris, pH 9.0 | 76 | 91 |
| 6 | MYC C28Y DOW.FT | C28Y | 50 mM Tris, 3.3 mM DTT, pH 9.0 | 79 | 98 |

Samples 1 and 3-6 are process intermediates (not final drug substance) obtained after prepurification of inclusion bodies, refolding and removal of detergent NLS (by Dowex chromatography or diafiltration). Sample 2 is an original wild type drug product produced by Biomeva/Thymoorgan and used in Phase III trials. The specification for the original drug product was 75-125% of the reference standard. All samples were judged as active (binding).

Example 3

Minimum Inhibitory Concentration Determination of *Cryptococcus neoformans*

Summary

In the MIC assay the antimycotic activity of MYC123, using *Cryptococcus neoformans* as model organism, was determined. This assay measures antifungal activity and may mimic the action of MYC 123 in the clinical setting.

The MIC of MYC 123 was determined by broth micro dilution according to the National Committee for Clinical Laboratory Standards document M27-A2 (2002). Briefly: RPMI medium was inoculated with $10^3$ CFU/ml of *C. neoformans*. MYC123 was added in decreasing concentrations to the medium (1024 µg/ml, 512 µg/ml, 256 µg/ml . . . ). The MIC plates were incubated at 37° C. for 72 h. The endpoints were determined as the concentration to produce optically clear wells (MIC-0) and the concentration resulting in a prominent decrease in turbidity (≧50% growth inhibition, MIC-2) compared with the growth control.

Method

Pre-Assay Preparation

Safety cabinet: A SAB plate was inoculated with *C. neoformans* and incubated for 48-72 hr at 35° C. The plate was sealed with parafilm.

Bench:

RPMI was prepared. Antifungal agents were prepared according to NCCLS methodology (M27-A2)—total of 11 concentrations in RPMI growth medium. Concentrations were at 2× the final concentration required for single MIC MIC Plate In a U-shaped 96-well plate—100 μl of the highest drug concentration to be tested (2× required concentration) was added to well 1 of rows A and B (assay done in duplicate). This was repeated across the columns on the plate with descending concentrations e.g. next concentration well 2 of rows A+B, next concentration well 3 of rows A+B. Well 12 contained growth medium only.

Safety Cabinet Inoculum Preparation—Direct colony suspension. A direct colony suspension of *Cryptococcus neoformans* was made from a 48-72 hr old plate into RMPI medium. This was adjusted to 0.5 MacFarlands standard (approx $1\times10^6$–$5\times10^6$ cfu/ml). A 1:50 dilution was made. A further 1:20 dilution (approx $1\times10^3$–$5\times10^3$ cfu/ml, 2× inoculum required) was made Safety cabinet: Plate inoculation. The plate was worked from well 12 to well 1. This avoided drug carryover. 100 μl of inoculum suspension was pipetted into each well (final inoculum ($0.5\times10^3$–$2.5\times10^3$ cfu/ml). Plates were sealed with parafilm.

Incubation

The MIC plates were incubated at 37° C. for 72 hrs. To check the inoculum, the inoculums suspension were serially diluted and 10l of the dilutions were plated out onto a SAB plate and incubated at 37° C. for 72 hrs.

Reading Results

Using a reading mirror; growth was compared with that of the 'no-drug' control (well 12) and growth scored as follows:

0—optically clear
1—slightly hazy
2—prominent decrease in growth (approx 50%)
3—slight reduction in turbidity
4—no reduction in turbidity MIC results obtained during the study as shown in Table 2

TABLE 2

| | Sample information | | | Bioassay data MIC 25 Feb. 2008/ 29 Feb. 2008 [μg/ml] |
|---|---|---|---|---|
| No. | Sample | Sample info | Buffer composition | |
| 1 | MYC123 WT DF.R | Wild type | 50 mM Tris, pH 9.0 | 128 |
| 2 | DP (#140602) | Wild type | 0.5 M urea, 0.2 M L-arginine pH 9.5 | 64 |
| 3 | MYC123 WT DOW.FT | Wild type | 50 mM Tris, 1 M sucrose, ~0.2% Tween20, 3 mM DTT, pH 3.0 | 16 |
| 4 | MYC123 WT DOW.FT | Wild type | 50 mM Tris, 3 mM DTT, pH 9.0 | 64 |
| 5 | MYC C28Y DF.R | C28Y | 50 mM Tris, pH 9.0 | 64 |
| 6 | MYC C28Y DOW.FT | C28Y | 50 mM Tris, 3.3 mM DTT, pH 9.0 | 64 |
| | Reference 070602 | | 0.5 M urea, 0.2 M L-arginine pH 9.5 | 128/64 |
| | Buffer FB | | 0.5 M urea, 0.2 M L arginine pH 9.5 | 512 or 256 |
| | Buffer Tris | | 50 mM Tris, pH 9.0 | >512 |
| | Buffer 6 | | 50 mM Tris, 3 mM DTT, 1 M sucrose, 0.2% Tween20, pH 3.0 | 16 |

Samples 1 and 3-6 were process intermediates (not final drug substances) obtained after prepurification of inclusion bodies, refolding and removal of detergent NLS (by Dowex chromatography or diafiltration). Sample 2 was on original wild type drug product produced by Biomeva/Thymoorgan and used in Phase III trials.

The MIC results obtained for the samples were compared with the results obtained for the corresponding buffer. All the samples were regarded active in comparison to the Reference 070602 besides sample 3. Sample 3 and the Buffer 6 gave the same results demonstrating that the buffer without MYC123 was toxic for the test organism. Values for the samples 1 and 4-6 were far from the values for Buffer Tris which indicates an increased reliability of the data.

Example 4

Summary

The aim of the Mycograb mutants was to obtain a mutant scFv peptide with improved structural properties compared with the wild type Mycograb. It was believed that through point mutations, especially the replacement of free cysteine by tyrosine, aggregation and formation of incorrect disulfide bonds during down stream processing should be reduced. It was also believed that exchanging the orientation of the heavy chain fragment with the light chain fragment and removing the HIS-Tag is be beneficial for formation of a native 3D structure of the Mycograb molecule.

After cloning, the constructs were sequenced prior to fermentation. The fermentation was scaled up to deliver enough material for inclusion body (IB) isolation and for further downstream processing. The expression constructs of the mutants were purified according to the adapted Biomeva process until the refold end step.

The physical parameters of a range of mutant Mycograb peptides was tested as set out in Examples 5 to 12.

An overview of the mutants tested and their mutations is given in Table 3. The wild type was included in the studies for comparison reasons.

TABLE 3

Name and structural properties of the 12 investigated Mycograb mutants and the wild type (myc 123)

| MUTANT | HIS tag | Linker length | VH-VL alignment | cysteines | additional mutations |
|---|---|---|---|---|---|
| MYC 118 | NO | 4X | VH N-terminal | 5 | |
| MYC 119 | NO | 4X | VL N-terminal | 5 | |
| MYC 130 | NO | 3X | VH N-terminal | 4 | C29Y, I30S, H69R, N86S, V139I, V140Q F147S, F151S, A176K, N213S |
| MYC 133 | NO | 5X | VH N-terminal | 5 | |
| MYC 135 | NO | 5X | VL N-terminal | 5 | |
| MYC 134 | NO | 6X | VH N-terminal | 5 | |
| MYC 137 | NO | 4X | VH N-terminal | 4 | C29Y, I30S |
| MYC 138 | NO | 5X | VH N-terminal | 4 | C29Y, I30S |
| MYC 106 origami | YES | 3X | VH N-terminal | 4 | oxidatives cytoplasma |
| MYC 136 | NO | 6X | VL N-terminal | 5 | |
| MYC 139 | NO | 6X | VH N-terminal | 4 | C29Y, I30S |
| MYC 123_Wt | YES | 3X | VH N-terminal | 5 | |
| MYC 140 | NO | 4X | VL N-terminal | 4 | C29Y, I30S |

The methodology used in the test assays will now be described.

Inclusion Body (IB) Isolation

4 L of fermentation broth obtained in LVA (Laborversuchsanstalt) from shake flask culture of Mutants Myc 118, 119, 130, 133 and Myc 135 were disintegrated with a high pressure homogenizer (LAB 40-15 RBFI) in RPP4 at 700 Bar for 2 cycles of 15 min each. The IBs were separated from the cell debris at lab scale with a bottle centrifuge at 10000 rpms for 20 min at 4° C. IBs were washed twice with water for laboratory use (WFL) and afterwards, a 20% (w/v) suspension in WFL was prepared. The suspension was stored in aliquots at −20° C.

IBs from mutants Myc 134, 137, 138, 106, 136, 139, 140 and Myc 123 (wt) were isolated at pilot scale in RPP4 because fermentation of these mutants was done at 30 L scale in bioreactors. IBs were separated from cell debris with a disc stack centrifuge. A 20% suspension (w/v) in WFI was prepared. This suspension was stored in aliquots at −20° C.

Solubilization

Solubilization with NLS (according to adapted Biomeva process). Solubilization of the 20% IB suspension was done by dilution with WFL to a protein concentration of 8 mg/ml followed by a 1:2 dilution with 100 mM Tris/Base, 4% NLS, pH 9.0 buffer. The solution was stirred at room temperature in a beaker until clarification but at least for 30 min. The time until start and end of clarification was recorded.

Alternative Solubilization with Urea, GuHCl, DTT. The alternative solubilization strategy was performed by a 1:10 dilution of a respective volume of 20% IB suspension with 20 mM Tris 8M Urea+/−5 mM DTT or 20 mM Tris, 6M GuHCl+/−5 mM DTT both at pH 9.0. The resulting concentration of urea and GuHCl was 7.2M and 5.2M respectively, due to the volume of the IB suspension solution.

Refolding of Solubilized IB's

Refolding with NLS. The refold was done by 1:4 dilution of the solubilization solution with a 50 mM Tris/Base buffer. The final concentration of NLS was 0.5%. Refolding was initiated by addition of 50 µM $CuCl_2$. Samples were taken and immediately submitted for RPC2 analysis prior and after $CuCl_2$ addition, then approximately 24, 48, 72 and 96 hours after $CuCl_2$ addition.

Refolding after solubilization with Urea, GuHCl. Refolding of a Mycograb solution after solubilization with 8M urea or 6M GuHCl+/−DTT was performed by 1:50 dilution with a buffer containing 20 mM Tris/Base, 1% NLS and 2 mM Cystin at pH 9.0.

For some mutants, dilution of a Mycograb solution after solubilization with urea by 1:10 with a buffer containing 20 mM Tris/Base, 0.5M L-arginine and 2 mM Cystin at pH 9.0 was also performed.

The refold solution was stirred for 96 hrs at 4° C. or 24 hrs at RT, respectively.

Refolding Kinetics

A refold kinetic was recorded for mutant Myc 119 in order to determine the required refolding time. A sample of a 20% IB suspension of Myc119 was solubilized as described above. Refolding was performed as described above, but samples were taken at respective time intervals and analyzed by RPC 2.

NLS removal by UF/DF from refolding solution. Mutants Myc119, Myc 137, Myc 106 and Myc 123 (wt) were solubilized and refolded as described above. After refolding, a buffer exchange of REF.END solution was performed with an Amicon stir cell with 10 kDa molecular weight cut-off. NLS concentration after each turn over volume was determined with RP-HPLC. 50 ml of REF.END solution were concentrated to 25 ml and then filled up again to 50 ml with diafiltration buffer. This procedure was carried out 4 times. Aggregation tendency after NLS removal was measured with SEC-HPLC running with formulation buffer.

SDS Page Analysis

SDS Page was performed using NuPAGE 4-12 BisTris gels and MOPS as running buffer. The run time was 65 minutes at 200 volt. A mass of 0.2-0.4 µg Mycograb was applied on each lane. After electrophoresis, the gels were stained with silver. For reducing SDS Page, 100 mM DTT was added to the sample.

Results

The expression construct of the mutants was analyzed at different stages in the down stream procedure with the analytical methods listed in Table 4:

TABLE 4

Code and description of process intermediates and the respective analytical assay

| CODE | Intermediate description | Analytical method |
|---|---|---|
| IB.RES | Resuspension of IB's (20% w/v) | RPC 1 |
| IB.SOL | Solubilized IB's | RPC 1, RPC 2 |
| REF.IM | Refold intermediate prior to $CuCl_2$ addition | RPC 1, RPC 2 |
| REF.END | Refold solution, endpoint | RPC 1, RPC 2, SEC 0.5% NLS, SDS PAGE red/non red, Pep-map, denat. SEC |

Table 5 gives a description of the analytical methods listed in Table 4 that were used for evaluation of the mutants. A comment is included describing the specificity of the particular assay.

TABLE 5

Analytical method, the respective response and Unit of Measurement (UoM) for the assays used to evaluate the mutant samples.

| Analytical method | Response | UoM | Comment |
|---|---|---|---|
| RPC 1 | total protein mass | mg/ml | This assay is not specific for Mycograb Sample is dissolved with SDS, DTT and urea |
| RPC II | chromatogram | $t_{R(monomer)}$ [min] | Assay can only be evaluated by overlay of chromatograms. Shift of the 'monomeric peak' indicates refolding |
| SEC 0.5% NLS | average molecuar weight | kDa | For samples containing 0.5% NLS. RT of peak maximum is correlated to MW. Broad elution peak from 43–900 kDa |
| SDS Page reducing | Monomeric/Dimeric band; Impurity content | band | Non-covalent aggregates are dissolved by reduction; in comparison to non reducing gel, semi-quantitative evaluation about aggregate content possible |
| SDS Page non-reducing | Monomer and aggregate bands | band | |
| Pep Map | Disulfide bridging | no, weak, strong and very strong signal | Ability to detect peptides depends on the sensitivity of the measuring device |
| SEC Formulation | average molecuar weight | kDa | For samples in a similar matrix as formulation buffer. RT of peak maximum is correlated to MW. |
| RPC NLS | NLS concentration | mg/ml | |

Further details of the respective assays for the investigated mutants are summarized and discussed in the following Examples 5 to 12.

Example 5

Mass Balance after Solubilization and Refolding—Results RPC1 Titer Determination Protein concentration prior and after solubilization and refolding of IB's was measured with the titer assay. As this assay measures all soluble protein present in the sample, mass balance should yield 100%. Mass balance for solubilization was calculated using equ. 1.

$$\% \, Sol = \frac{mg_{RPC1} IB.SOL}{mg_{RPC1} IB.RES} \quad \text{equ. 1}$$

where $mg_{RPC1}$ IB.SOL is the mass of protein in the solubilzation solution of the IB's calculated from concentration measurement by RPC 1 method and volume of IB SOL solution. $mg_{RPC1}$ IB.RES is the mass in the 20% IB suspension calculated from concentration measurement by RPC 1 method and volume of the solution after resuspension of the isolated IB's in DI.

Mass balance for refolding was calculated using equ. 2 and is expressed as % recovery. IB's solubilized with either 4% NLS, 8 M urea+/−5 mM DTT or 6M GuHCl+/−5 mM DTT were diluted and refolded as described in 3.3.1 and 3.3.2, respectively.

$$\% \, Ref = \frac{mg_{RPC1} Ref.END}{mg_{RPC1} IB.SOL} \quad \text{equ. 2}$$

where $mg_{RPC1}$ Ref.END is the mass of protein according to concentration measurement with RP-HPLC found in the refolding solution times volume of refolding solution. mg $_{RPC1}$ IB.SOL is the mass of protein found in the IB solubilisate, % REF is the recovery after refolding.

Figure 3:
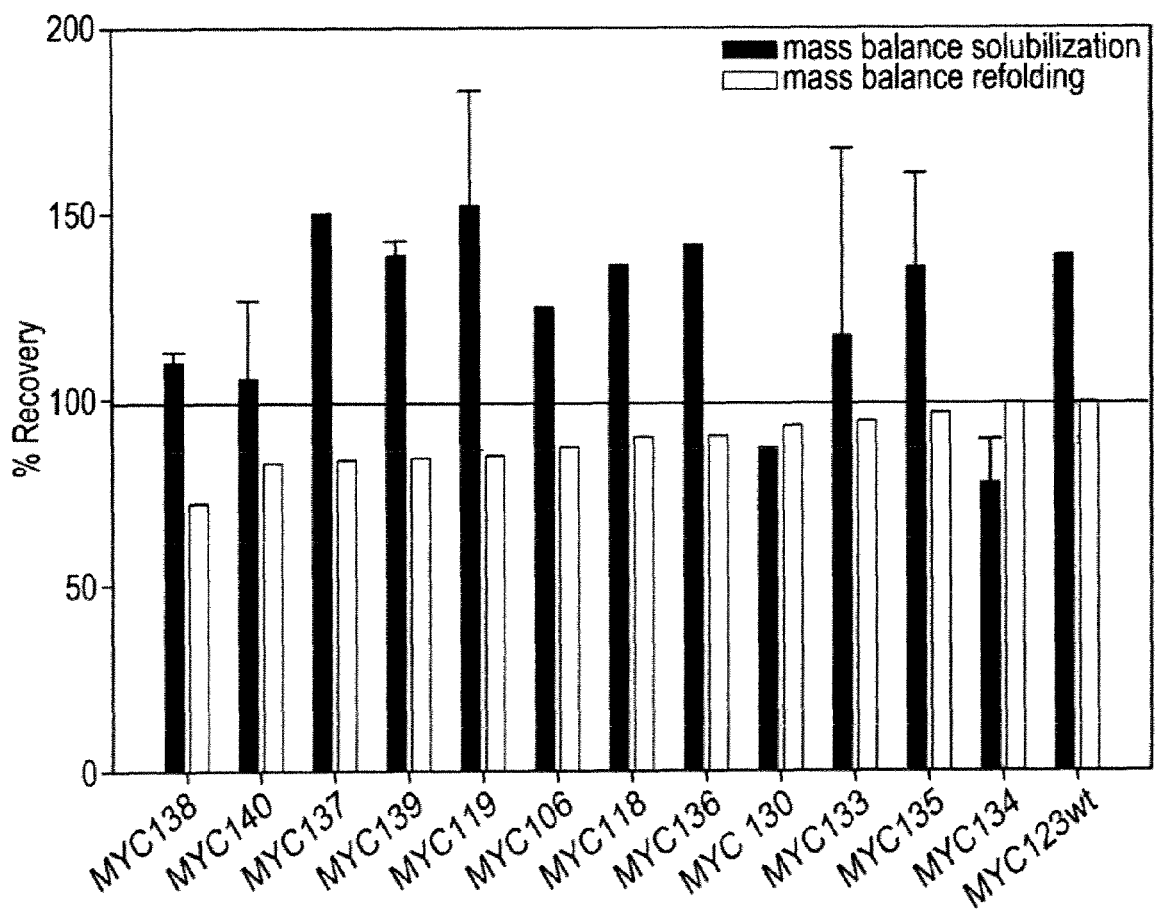
FIG. 3 is a graph in which the black bars show yield after solubilization with NLS of all investigated mutants. The error bars show the Standard deviation for samples analyzed twice. The white bars are a graphic representation of mass balance after NLS refolds of all investigated mutants. Mutants are ranked according to increasing refolding recovery values.

Mass balance after solubilization with 4% NLS and subsequent refolding of all mutants as calculated by equations 1 and 2 are illustrated in FIG. 3. Raw data can be found in Tables 6 and 7.

Table 6 shows the recovery after solubilization with NLS of the IB_RES suspension and recovery after refolding calculated from analytical method RPC I for all tested mutants. Also shown is the protein concentration in the IB-RES solution and protein concentration in the refolding solution determined by analytical method RPC I. Table 7 shows protein concentration determined by RPC I of IB_RES, IB_SOL and REF.END samples after solubilization with urea (SOL:urea) and solubilization with GuHCl (SOL:GuHCL). Refolding time was 96 hrs at 4° C. The dilution factor was 500 and 50 for IB_RES and IB_SOL, respectively to yield the REF.END solution.

TABLE 6

| Mutant # | c [mg/ml] IB_RES | Recovery solubilization (%) | c [mg/ml] ref.end | Recovery refolding (%) |
|---|---|---|---|---|
| MYC 138 | 27.2 | 110 | 1.18 | 72 |
| MYC 123wt | 54.9 | 138.75 | 1.65 | 99.2 |
| MYC 140 | 18.7 | 105.55 | 1.46 | 82.8 |
| MYC 137 | 19.2 | 150.25 | 1.83 | 83.7 |
| MYC 139 | 19.9 | 138.66 | 1.82 | 84.2 |
| MYC 119 | 13.6 | 152.27 | 1.59 | 84.84 |
| MYC 118 | 19.8 | 136.1 | 1.77 | 89.8 |
| MYC 136 | 15.1 | 141.5 | 1.76 | 90.1 |
| MYC 133 | 16.3 | 117.175 | 2.09 | 94.1 |
| MYC 135 | 11 | 135.65 | 1.82 | 96.3 |
| MYC 134 | 35.9 | 77.35 | 2.73 | 99.1 |
| MYC 106 | 13.7 | 124.75 | 2.95 | 87.1 |
| MYC 130 | 19.4 | 87 | 1.84 | 92.9 |

TABLE 7

| Mutant # | c IB_RES | c IB_SOL | SOL: urea c REF.end | SOL: GuHCl c REF.end |
|---|---|---|---|---|
| MYC 118 | 19.8 | 2 | 0.091 | 0.075 |
| MYC 119 | 13.6 | 3.46 | 0.07 | 0.056 |
| MYC 130 | 19.4 | 2.94 | 0.044 | 0.026 |
| MYC 133 | 16.3 | 1.34 | 0.023 | 0.0193 |
| MYC 135 | 11 | 1.41 | 0.035 | 0.042 |

Mass balance of solubilization was exceeding 100% for 10 of the 12 investigated mutants. This could be due to the fact that the IB suspension was a crude sample type and eventually, the IB's were not completely dissolved when the sample was taken, leading to an inhomogeneous solution and thus underestimating total protein concentration. Data variability is high, with a relative standard deviation for 6 mutants analyzed twice ranging from 2.6% (Myc 138) to 42.9% (Myc 133). % Recovery after refolding was between 72% (Myc 138) and 99% (Myc 134). The expected recovery is 100% (similar to recovery after solubilization). Recoveries after refolding were all lower than 100% and scatter not as much as for recovery after solubilization. This indicates that estimation of protein concentration in IB.SOL and REF.end samples is more accurate than in IB.RES samples. However, calculation of recovery primarily serves as a control for solubilization and refolding experiments.

Figure 4:
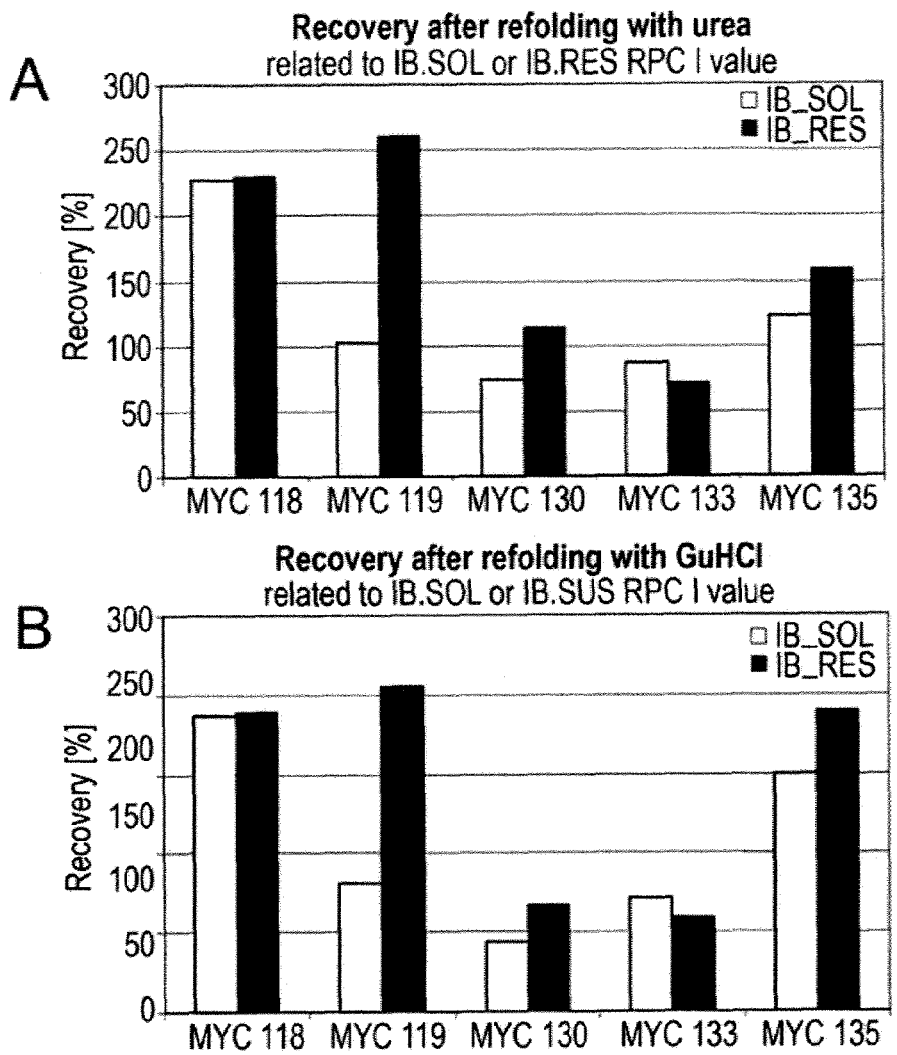
FIG. 4 shows graphs indicating the recovery after refolding for 5 selected mutants when urea and DTT was used as solubilizing agent (A) and when GuHCl and DTT were used as solubilizing agent (B). White bars: Recovery when mass of protein found in the IB.SOL solution was used for calculation (equ. 1) Black bars: Refolding recovery when mass of protein found in the IB.RES solution is used for calculation.

Refolding yields related to the solubilization solution IB.SOL and the IB suspension IB.RES when 8M urea or 6M GuHCl was used as solubilization agent are shown in FIG. 4.

The recovery varies from 44% to 230% reflecting the problems with measurement of protein concentration especially in IB.SOL and IB.RES samples, possibly due to insufficient homogenization prior to sampling.

Concentration in the REF.END samples after urea solubilization was comparable to concentration in REF.END after GuHCl solubilization (see Tables 6 and 7) though by an average factor of 1.2 higher. Dilution was thus consistent.

Example 6

Solubilization Time

Figure 5:
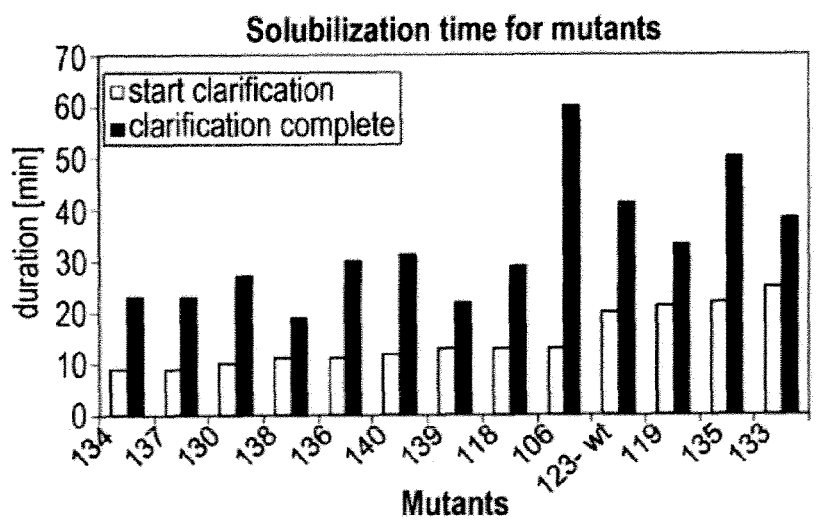
FIG. 5 is a graph showing the time required for a visible beginning clarification of a solubilization solution after addition of 4% NLS (white bars) and the time required until no further clarification was observed (black bars) for all tested mutants. Mutants are ranked according to the start time in ascending order.

Solubilization time with NLS was studied for all mutants. The time until the solution started to become clear and the time until no further clarification could be observed was recorded and is illustrated in FIG. 5.

In contrast to using 2% NLS, solubilization with Urea+/−DTT and GuHCl+/−DTT was 2-3 times faster.

Figure 6:
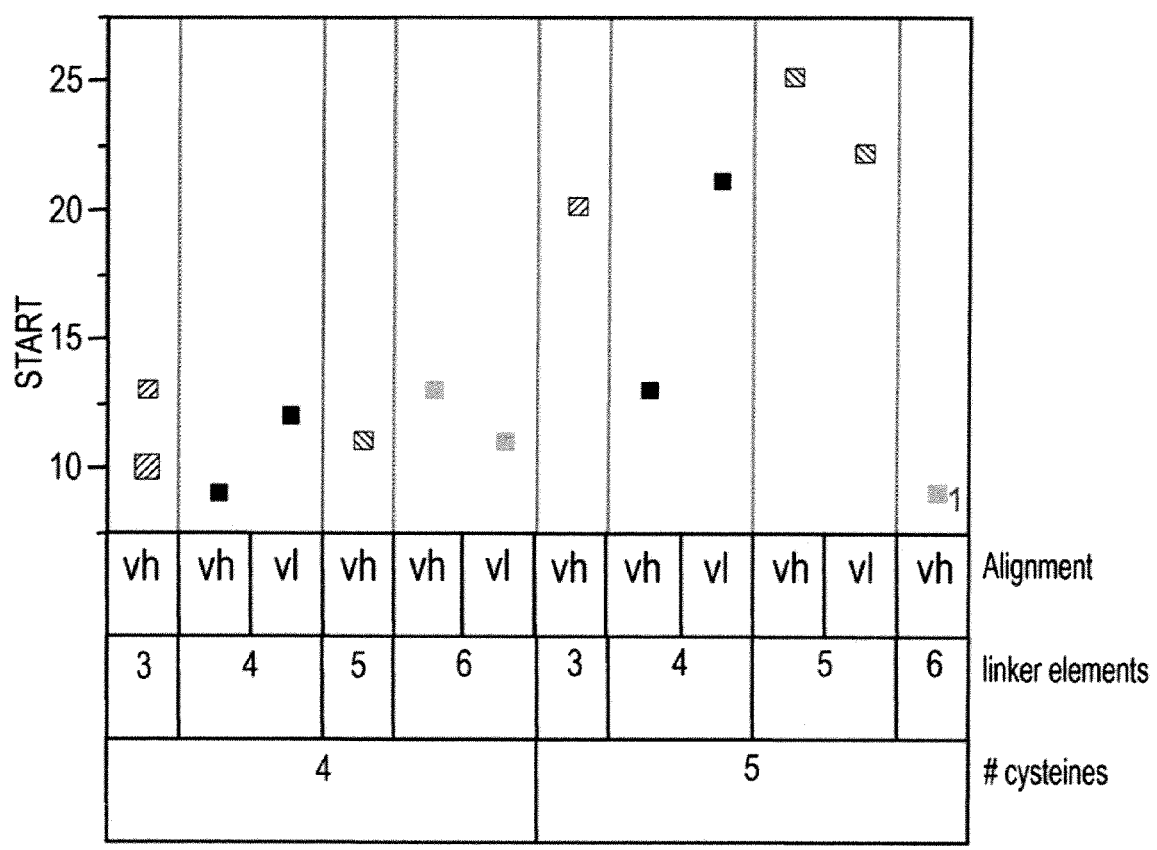
FIG. 6 is a variability chart for the response start of solubilization and indicates number of cysteines, number of linker elements and if the heavy (vh) or light chain (vl) fragment was at the N-terminus. 1: Mutant Myc 106 had the fastest solubilization start but contained 5 cysteines.

A correlation between the number of Cysteines and time required for clarification to start was found. With the exception of mutant 134 (5 cys), mutants with 4 cysteine residues solubilized faster than mutants with 5 cysteine residues. FIG. 6 shows a variability chart where START [min] of clarification is plotted versus the 3 categories: alignment of heavy or light chain fragment at the N-terminus, number of linker elements and cysteine residues. With exception of Myc 134, indicated with 1 in FIG. 6, data points in category with 4 Cysteines scatter around earlier solubilization start times than compared with data points in the category with 5 cysteines.

A regression model ($R^2$=0.72 when Myc 134 is excluded) predicted that start of solubilization would decrease from 20 min to 11.3 min for a Mycograb construct with 4 cysteines instead of 5 (model not shown).

Example 7

RPC 2—NLS Refolds

Mycograb REF.END samples solubilized and refolded according to Biomeva adapted process (described in Example 4) mutants were analyzed by RPC 2.

Figure 7:
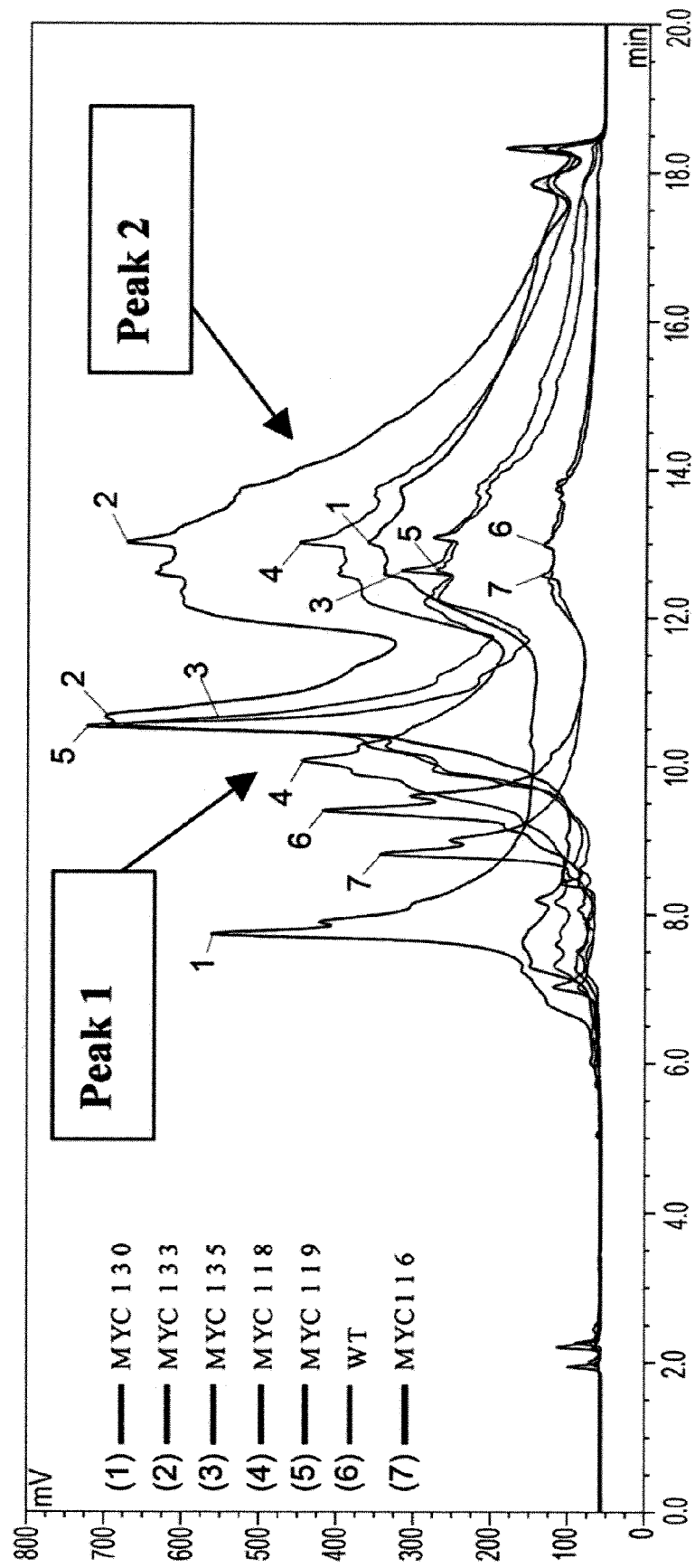
FIG. 7 shows chromatograms as an overlay of REF end samples of Mutants MYC 135, Myc 130, Myc 133, Myc 119, Myc 123 wild type and Myc 116.
Figure 8:
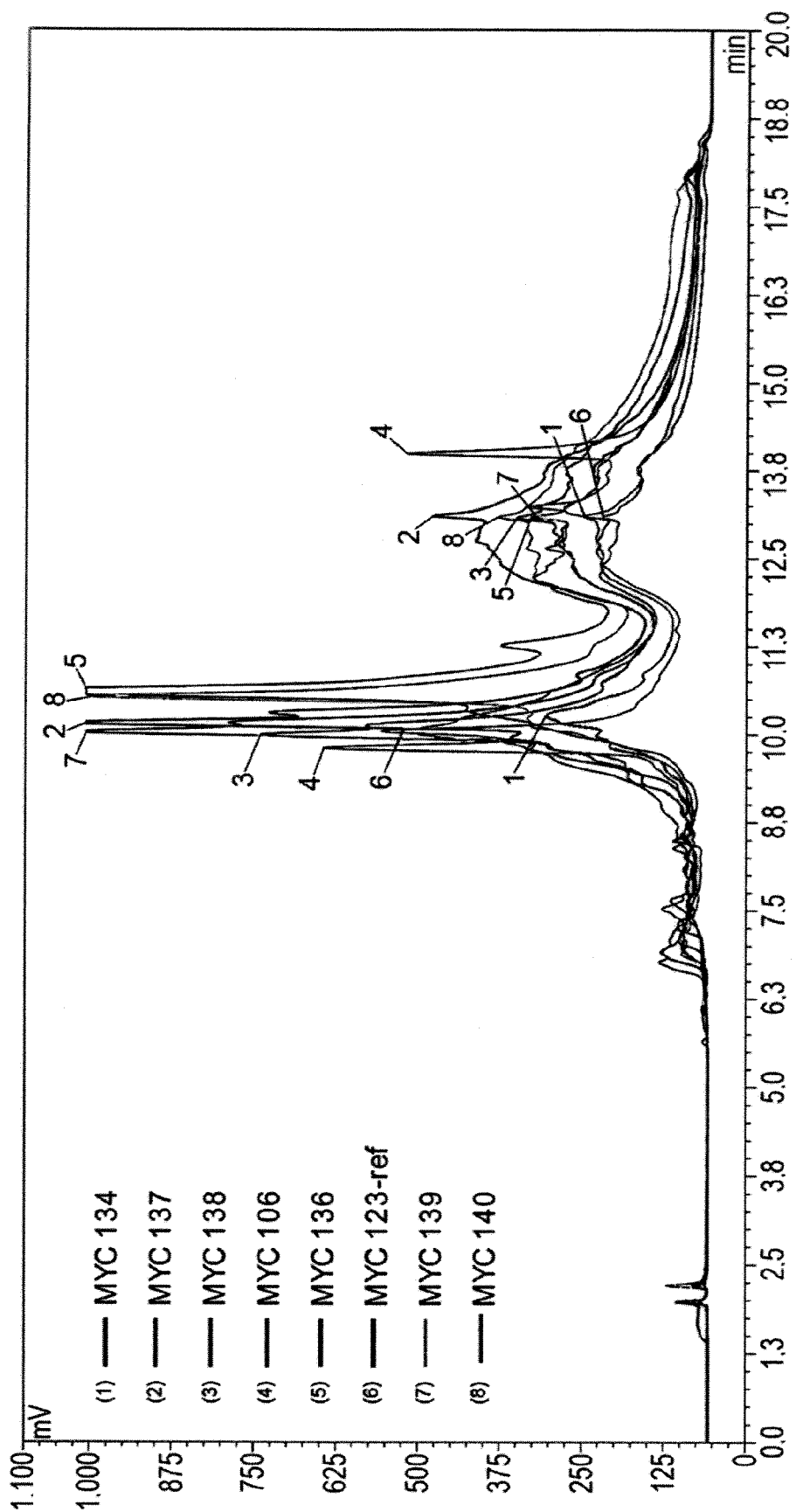
FIG. 8 shows chromatograms as an overlay of REF end samples of Mutants MYC 134, Myc 137, Myc 138, Myc 106 Myc 136, Myc 123 and Myc 139.

An overlay of REF.END samples from all investigated mutants including the wild type (MYC 123) is shown in FIG. 7 and FIG. 8. Mutant Myc 116 was screened earlier in lab DSP-DEV 1 and was included in the overlay for comparison reasons.

In FIG. 7, chromatograms of REF.END samples generated from IB's isolated at bench scale and in FIG. 8, chromatograms of REF.END samples generated from IB's isolated at larger scale in the pilot plant are shown.

Elution Profiles were Compared with Respect to:
 1. Retention time peak 1, reflecting hydrophobicity
 2. Shape of peak 1, reflecting presence of dimer and homogeneity of monomer species when the peak is sharp
 3. Ratio area of monomer/dimer peak (peak 1) to aggregate/impurity peak (peak 2), reflecting aggregate/impurity content Retention Time Peak 1, Reflecting Hydrophobicity The retention time of the monomer/dimer peak for the tested mutants is listed in Table 8.

TABLE 8

Retention time [min] of peak 1 in RPC2 for the tested mutants and the molecule properties

| Mutant | $t_r$ [min] | linker | cystein | chain orientation |
|---|---|---|---|---|
| MYC 130 | ave: 8.16 n = 3; RSD = 4.6% | 3X | 4 | VH |
| MYC 106 origami | 9.8 | 3X | 4 | VH |
| MYC 138 | 9.99 | 5X | 4 | VH |
| MYC 139 | 10.035 | 6X | 4 | VH |
| MYC 123_Wt | 10.041 | 3X | 5 | VH |
| MYC 118 | 10.075 | 4X | 5 | VH |
| MYC 137 | 10.116 | 4X | 4 | VH |
| MYC 134 | 10.26 | 6X | 5 | VH |
| MYC 140 | 10.526 | 4X | 4 | VL |
| MYC 119 | 10.535 | 4X | 5 | VL |
| MYC 135 | 10.558 | 5X | 5 | VL |
| MYC 136 | 10.637 | 6X | 4 | VL |
| MYC 133 | 10.659 | 5X | 5 | VH |

Retention time varies greatly with molecule construct. There is no trend of retention time (reflecting hydrophobicity) increasing with linker length, as would be expected. One linker element consists of four Glycines and one Serine residue. Glycine is hydrophobic in contrast to Serine, which is hydrophilic. However, the 4× higher Glycine content in the linker seems not to significantly increase the hydrophobicity as measured by retention time in RPC 2.

Figure 9:
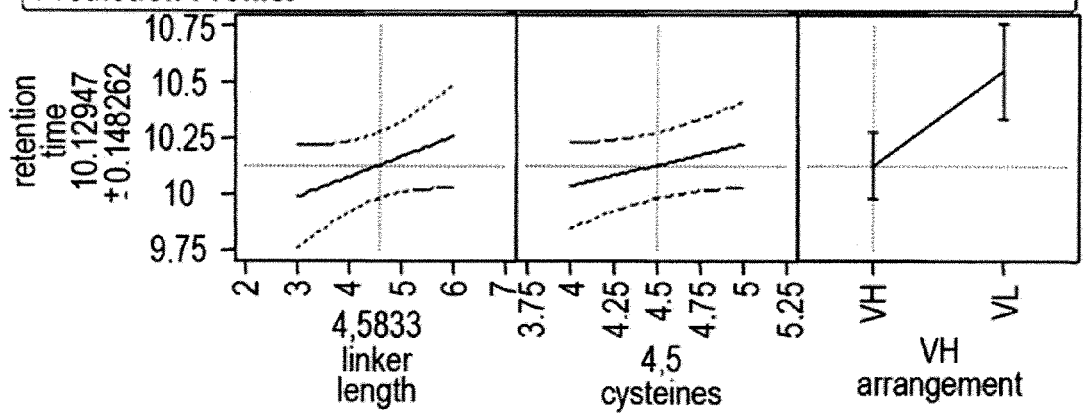
FIG. 9 shows scaled estimates and a prediction profiler of the following parameters: linker length, number of cysteines and Vh/Vl arrangement for the response retention time of mutants. The scaled estimates predict to what extent the retention time would shift when the parameter is increased from centerpoint (the red number in the prediction profiler plot on the x-axis) to a higher level.

Retention time of Myc 130 is shorter than for the rest of the mutants. 10 amino acids were replaced by amino acids of more hydrophilic (5 serines) nature, thus decreasing the hydrophobicity of the molecule und consequently resulting in earlier retention time. Excluding this data point from statistical analysis results in a model showing significant difference in retention time when the orientation of the VL is N-terminal compared to an orientation when its C-terminal. Retention time increases by 0.41 min when the VL element is located N-terminal compared with when its located C terminal. FIG. 9 shows the scaled estimates and a prediction profiler of the model with number of cysteines, linker length and chain fragment orientation as factors and retention time as response.

Figure 10:
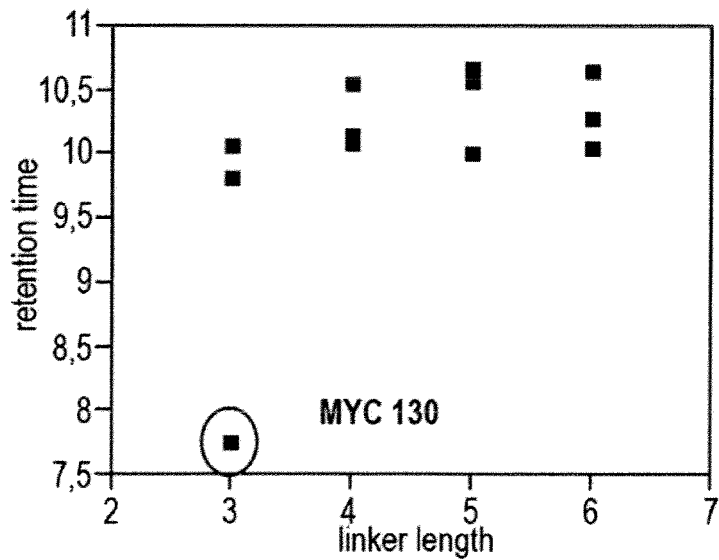
FIG. 10 is a plot of linker length versus retention time measured in RP-HPLC (RPC2) for tested mutants. The early retention time of MYC 130 compared with the other mutants is highlighted.

Note that retention time of Myc 130 was excluded from the model. A plot of retention time versus linker length, shown in FIG. 10, demonstrates that retention time for this construct is lower compared to the rest of the mutants because of point mutations resulting in more hydrophilic nature, as mentioned above.

Shape of Peak 1

It is assumed that a sharp peak 1 with no or only little shoulders reflects the homogeneity of a monomeric Mycograb. Peak shape was assessed by overlays of the RPC 2 chromatograms of REF.End samples from all mutants and sharpest peaks were determined for the mutants Myc 137, Myc 138 and Myc 139. Peak1 was sharper than the wild type Myc 123 and peaks 1 and 2 were almost base-line separated. This may be an indication that these constructs express the monomeric/dimeric protein with greater homogeneity than the wild type.

Ratio Area of Monomer/Dimer Peak

Impurity/aggregate content in relation to monomer/dimer was lowest for Myc 116 and MYC123 wt as shown in FIG. 7 (Myc 123 wt). However, analysis of these two samples was performed 3 months earlier by another laboratory and an increase of peak 2 was noticed over time. A chromatogram of REF.End sample from Myc 123 that was prepared and analyzed in the same month as REF.End samples of the tested mutants is shown in FIG. 8. Comparison of the chromatogram of MYC 123 shown in FIG. 7 with that of shown in FIG. 8 leads to the conclusion that sample preparation and analytical method are not exactly reproducible.

Figure 11:
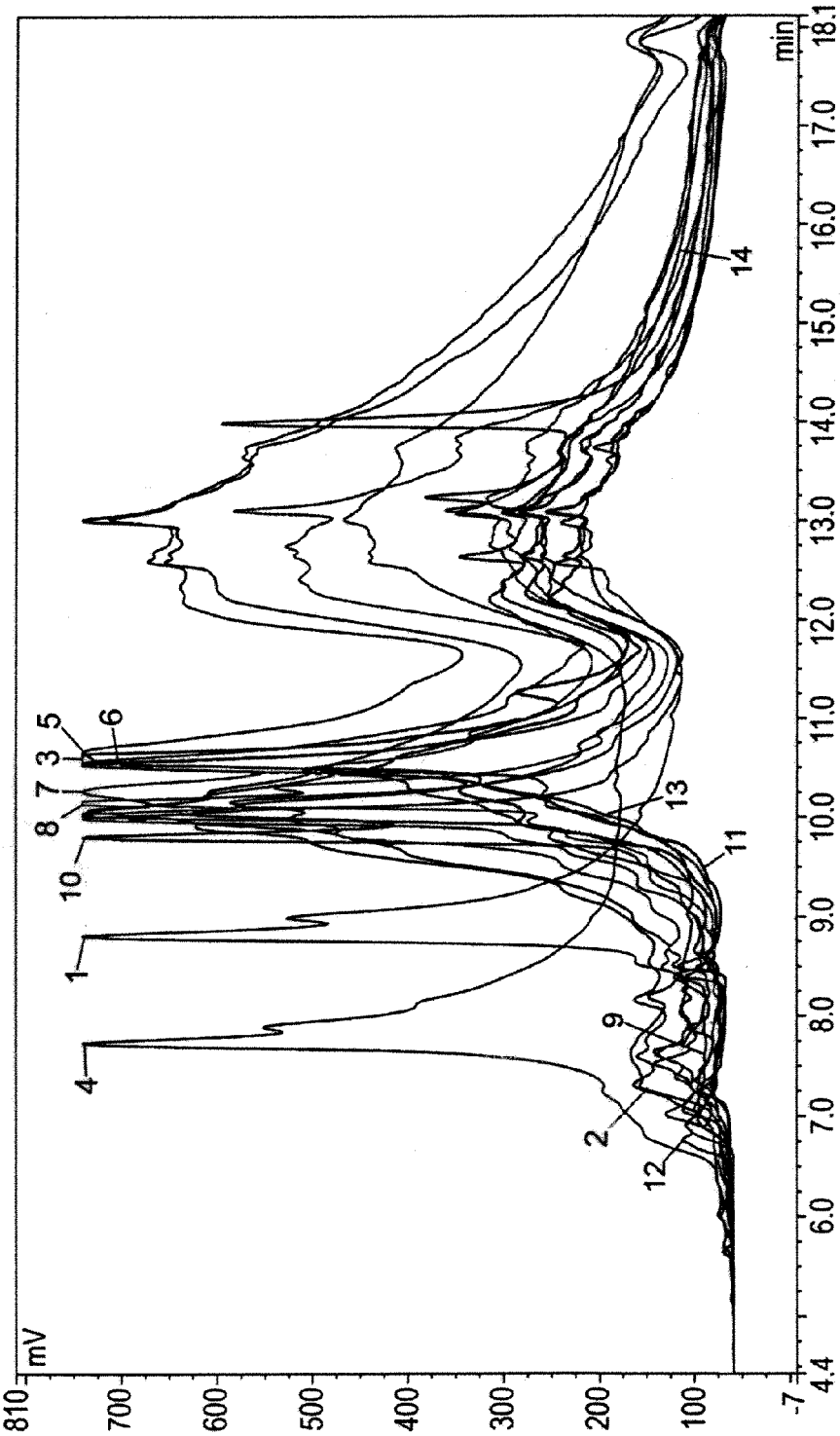
FIG. 11 shows a normalized overlay of all REF.END samples from FIGS. 7 and 8 for estimation of peak area from peak 2.

The area ratio of monomer/dimer peak to aggregate peak was determined by normalizing peak 1 to the same peak maximum. The peak area of peak 2 after normalization was ranked according to increasing size using visual area estimation. The normalized overview is shown in FIG. 11.

The Following Ranking could be Established:

Myc 116, Myc 139, Myc 136<Myc 119, Myc 12, Myc140<Myc137, Myc 135, Myc138<Myc106<Myc130<Myc 134<Myc118<Myc133

RPC 2 chromatograms of REF.End samples generated from IBs of mutants Myc 106, 134, 136-139 were processed in the pilot plant and showed lower impurity/aggregate peaks (cf FIG. 8) than IB's of mutants Myc 118-135 isolated at bench scale.

Example 8

RPC 2 Urea/GuHCl Refolds

Mutants Myc 118, 119, 130 and Myc 133 were dissolved with 7,6M Urea+/−DTT and 5,6M GuHCl+/−DTT and refolding was initiated by dilution in refolding buffer.

All REF.End samples did not show the monomer/dimer peak (peak 1) in RPC 2. A huge peak 2, assumed to be aggregates and impurities is predominant. A representative RP HPLC chromatogram of a refold end sample from mutant Myc 119 is given in FIG. 12. The sample was prepared as described in Example 4.

The monomer was expected to elute at approximately 10.5 min. Peaks eluting earlier are not identified and were not observed in refolds with 0.5% NLS. The huge peak 2 indicates strong aggregation. Similar elution profiles were obtained for all REF.End samples after urea/GuHCl solubilization.

Figure 13:
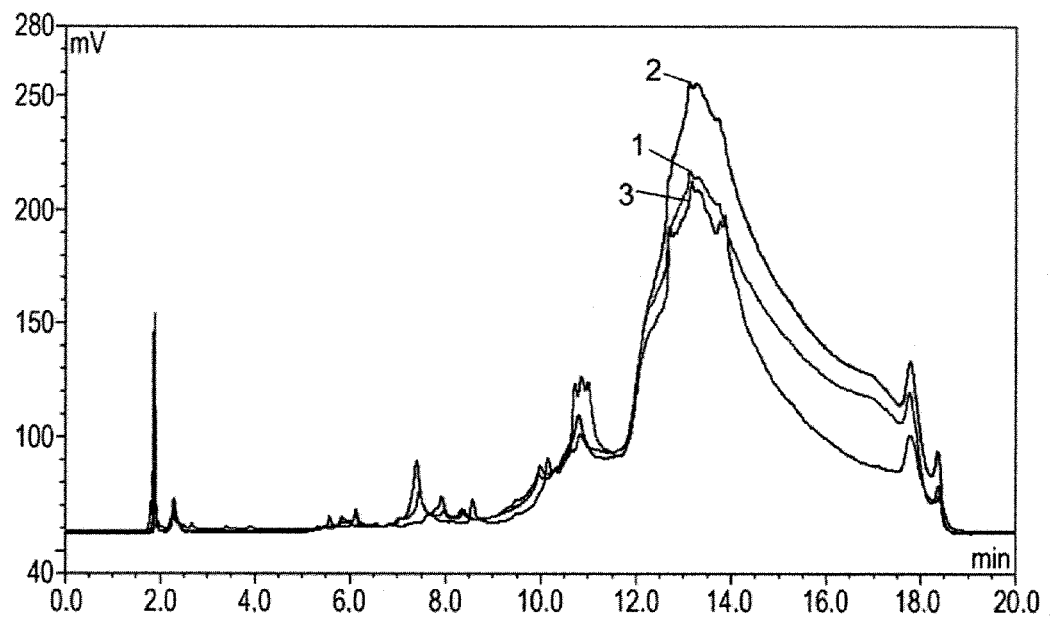
FIG. 13 is an RPC 2 chromatogram of a REF.End sample of MYC 119 after solubilization with 6M urea and 5 mM DTT and subsequent refolding by a 1:10 dilution.

Similar elution profiles were obtained when the refold was done by 1:10 dilution with a buffer containing 20 mM Tris/Base, 0.5M L-arginine and 2 mM Cystin at pH 9.0. A representative chromatogram is shown in FIG. 13.

Figure 14:
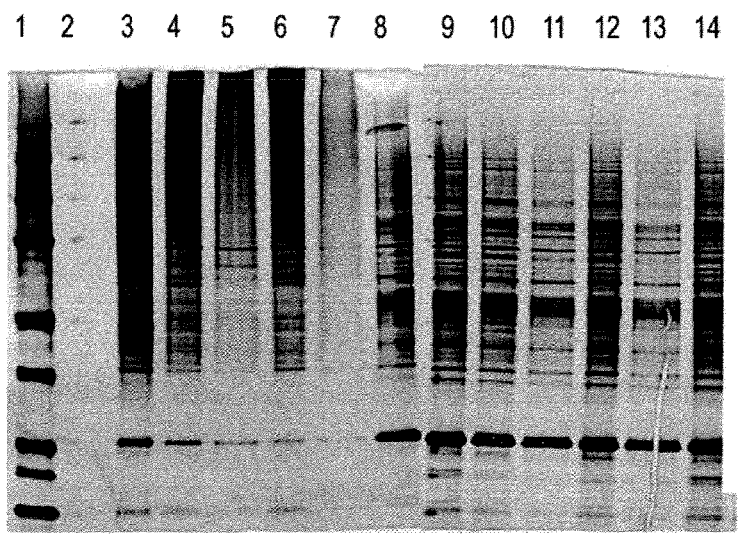
FIG. 14 is an image of a gel following SDS Page analysis of REF.IM and REF.END sample of MYC 119 after solubilization with 6M urea and refolding by a 1:10 and 1:50 dilution, respectively. Lanes 1-8: non reducing SDS Page, lanes 9-14: reducing SDS Page. R=reducing; n-r=non reducing

The strong aggregation tendency was confirmed by SDS-Page under non reducing conditions, a huge and intense HMW smear was detected for a REF.End sample, with no monomeric band visible after urea solubilization. This smear then disappeared when the sample was reduced and a monomeric Mycograb band appeared. In FIG. 14, SDS Page analysis of a reduced and non-reduced REF.End sample after urea solubilization is shown. Lanes 4-7 show REF.IM and REF.End sample of MYC 119 under non-reducing conditions at 2 different dilutions. Lanes 10-13 show the same sample under reducing conditions. The aggregate smear disappeared when the sample was reduced and the monomeric as well as the dimeric band became visible.

Figure 12:
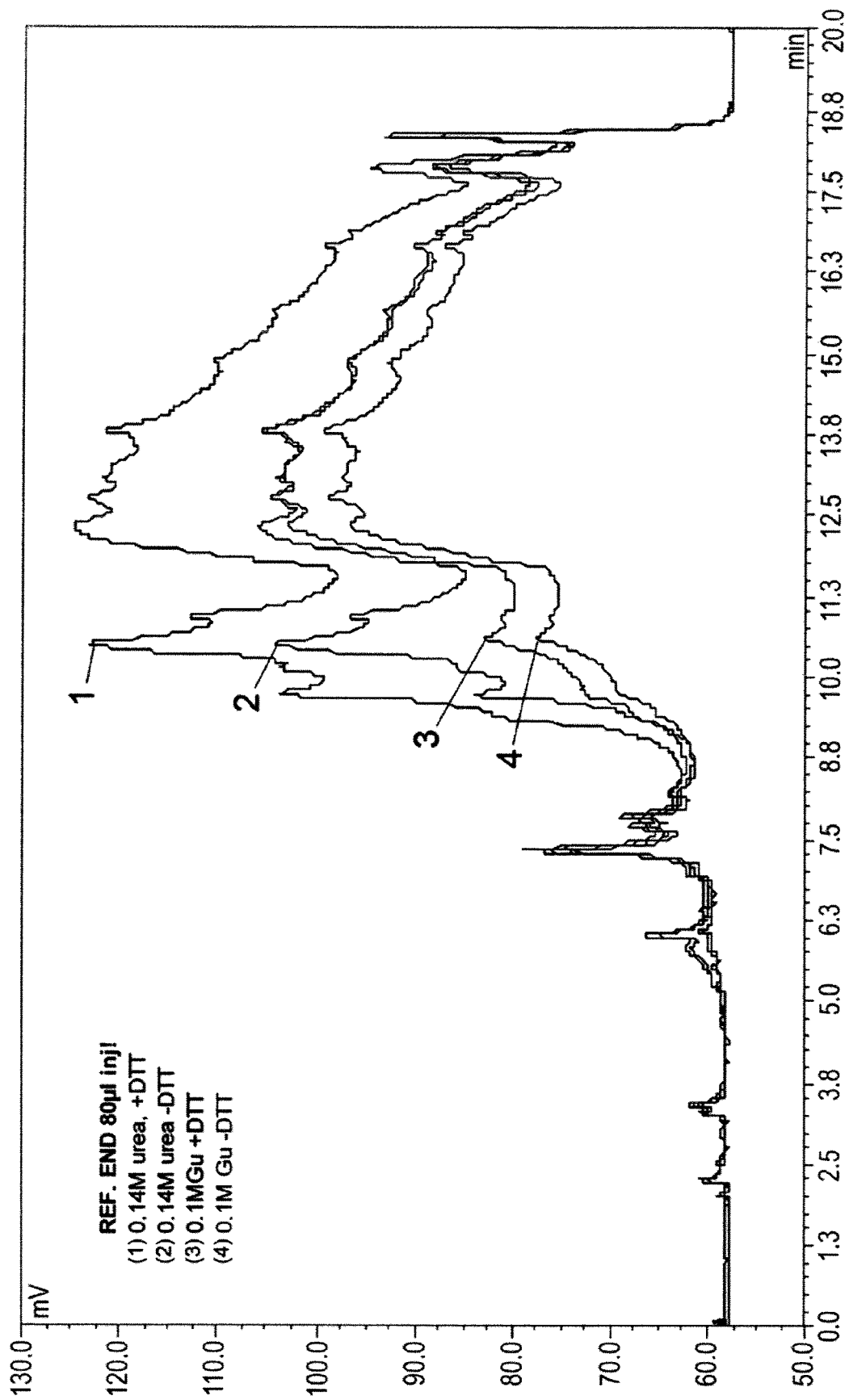
FIG. 12 shows a RP-HPLC 2 chromatogram overlay of a REF.End sample of MYC 119 solubilized with 8M urea +DTT, 8M urea, 6M GuHCl +DTT and 6M GuHCl dilution was 1:50 with a buffer containing 20 mM Tris, 2 mM cysteine, 1% NLS, pH 9.0.

Urea and GuHCl were present in the refolding solution at low concentration (0.14M in case of a 1:50 dilution and 0.72M in case of a 1:10 dilution for urea; for GuHCl, it was 0.11M in case of a 1:50 dilution and 0.56M in case of a 1:10 dilution) cannot prevent the protein from aggregation. Using DTT does not seem to have a significant effect on aggregation as RP-HPLC chromatograms (RPC 2) with and without DTT looked comparable, as shown in FIG. 12.

Figure 15:
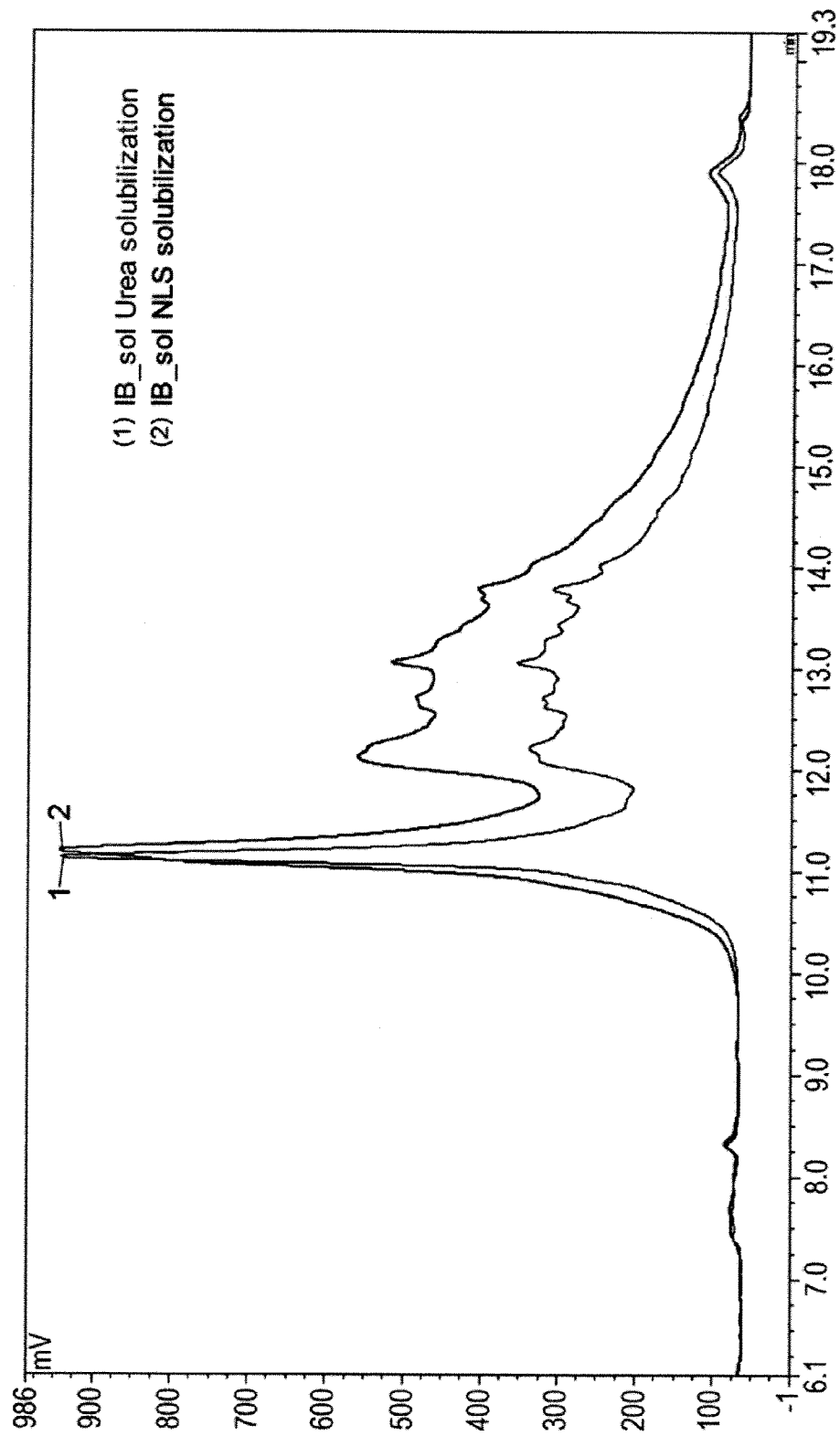
FIG. 15 is an RP-HPLC chromatogram overlay (RPC 2) of an inclusion body sample from mutant MYC 119 after solubilization with 6 M urea (black) and 4% NLS (blue).

In contrast to the REF.End sample, RPC 2 chromatogram of a IB.SOL sample dissolved with urea was comparable in terms of peak shape with a IB.SOL sample dissolved in 2% NLS. FIG. 15 shows an overlay of HPLC chromatograms.

SDS-Page analysis of a non-reduced IB.SOL sample showed stronger HMW bands when the sample was dissolved with urea than in case of a IB.SOL sample dissolved in 2% NLS. This is shown in FIG. 14: in lane 3, the sample was solubilized with urea and in lane 8, the sample was solubilized with 2% NLS. It can be concluded that peak 2 in RP-HPLC does not give an indication about aggregate content since peak 2 of an chromatogram overlay is even smaller for an IB.SOL sample in urea than in NLS.

Subsequent refolding did not yield a monomeric peak but the protein completely aggregates.

Example 9

SDS-PAGE Reducing and Non-Reducing

Reducing and non-reducing SDS-Page was performed to determine impurities and aggregates content in REF.End samples. With reducing SDS-Page Mycograb species appeared as monomeric and dimeric band and host cell impurity content in the sample could be distinguished from aggregated species when compared to a non-reducing SDS-Page gel. Non-reducing SDS Page showed Mycograb monomers, dimers and aggregates. Comparing a non-reduced SDS-Page silver stain gel with a reducing SDS-Page analysis, the amount of aggregated species could be evaluated semi-quantitatively.

Figure 16:
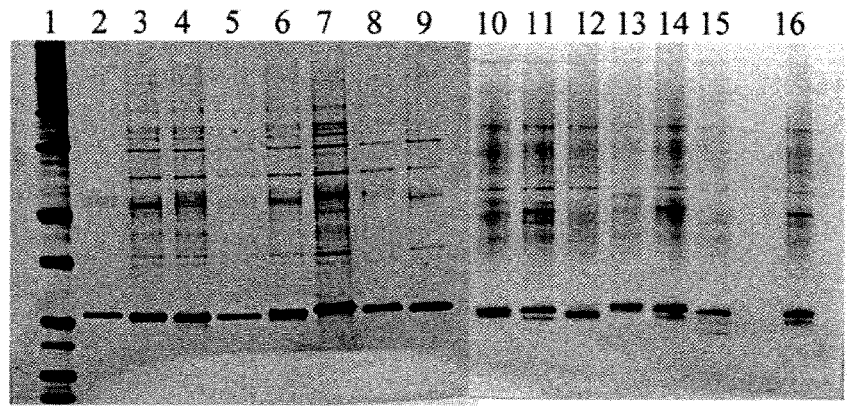
FIG. 16 shows images of: left gel: Reducing (r) SDS-Page for Mutants MYC 118, 119, 130, 133, 134, 135 and 137; and right gel: Non-reducing (n-r) SDS Page of the same samples
Figure 17:
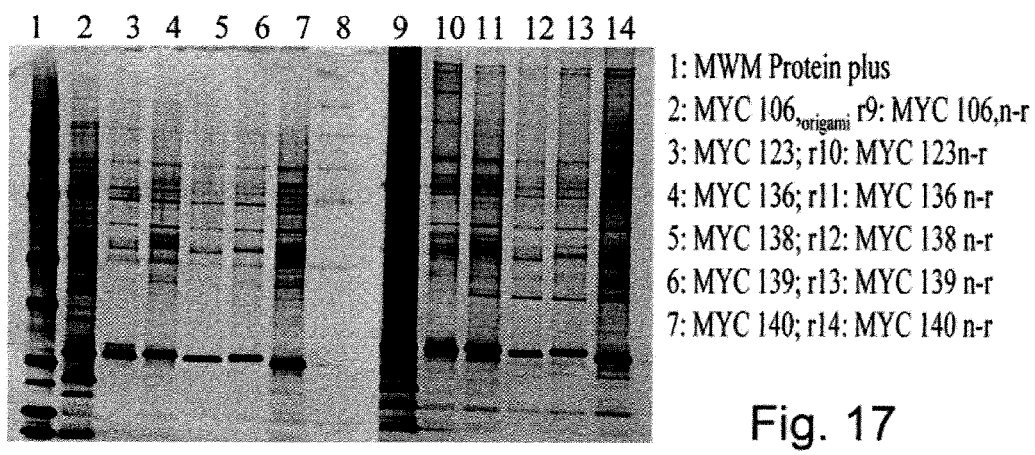
FIG. 17 shows images of:: left gel: Reducing SDS-Page for Mutants MYC 106, 123 wt, 136, 138, 139 and 140; and right gel: Non-reducing SDS Page of the same samples

Reducing and non-reducing SDS-Page gels of REF.END samples of all tested mutants are shown in FIG. 16 and FIG. 17.

The gel in FIG. 16 on the left side shows a reducing SDS-Page of REF.End samples from mutants MYC 118, 119, 130, 133, 134, 135, 137. The band at 30 kDa is monomeric Mycograb and it is predominant in all samples. According to the migration of the monomeric band, Mycograb expressed in mutant MYC 134 seems to have higher molecular weight than the other mutants analyzed on the gel. The same but to a lesser extend was detected for MYC 135. According to Table 9, MYC 134 has the highest theoretical molecular weight among the mutants shown in FIG. 16, followed by MYC 135.

In the non reducing SDS-Page gel, aggregated species as well as the dimer are visible. In lanes 13 (MYC 134) and 15 (MYC 137), HMW bands are fainter than in the other lanes. This would indicate a lower content of aggregated species, however, also the bands for the monomer are more faint.

Double bands of different migration time and intensity in comparison with each other were observed for all mutants with exception of Myc 133 shown in FIG. 16. Identification of these bands was hardly possible, however it was assumed that it was Mycograb Monomer of native like structure.

FIG. 17 shows a reducing and non-reducing SDS Page of REF.End samples from mutants MYC 106, 136, 138, 139, 140 and the wild type, MYC 123. Differences in MW for the different constructs could be determined according to different migration of the monomeric band. The bands in lanes 5 and 7 appeared at a slightly lower MW than the bands in lanes 2,3,6 and 4 which was in agreement with the theoretical MW listed in Table 9.

The mass of protein applied to the gel was not consistent; monomeric bands varied in intensity because protein concentration determination in the REF.End sample was not accurate enough. Thus semi-quanitative analysis of impurity content was not possible. However, the higher impurity content in REF.end sample of Myc 106 was obvious as the thickness of the monomeric band was comparable to one of Myc 140 but the intensity of the other bands was much higher.

SDS-Page analysis indicated that a REF.End sample of Myc 106 origami contained more HCP and product related impurities. However, this was not confirmed by RPC2 analytical method, where the area of peak 2 was in the same range as for the other mutants.

Example 10

SEC 0.5% NLS: Determination of Molecular Weight of Mycograb Species in the REF. END Sample All REF.END samples prepared according to the adapted Biomeva process (see Example 4) were analyzed with SEC—HPLC in 0,5% NLS and the average molecular weight was determined. An overlay of the SEC chromatograms is shown in FIG. 18 and FIG. 19.

The average molecular weight ranged from 48.6 kDa to 65.8 kDa. The broadness of the peaks reflects the heterogeneity of species in the sample. Though approximately 80% of the product was monomeric in REF.End samples, dimers and higher MW species were present as well as non-product related impurities, resulting in a broad elution peak.

Figure 18:
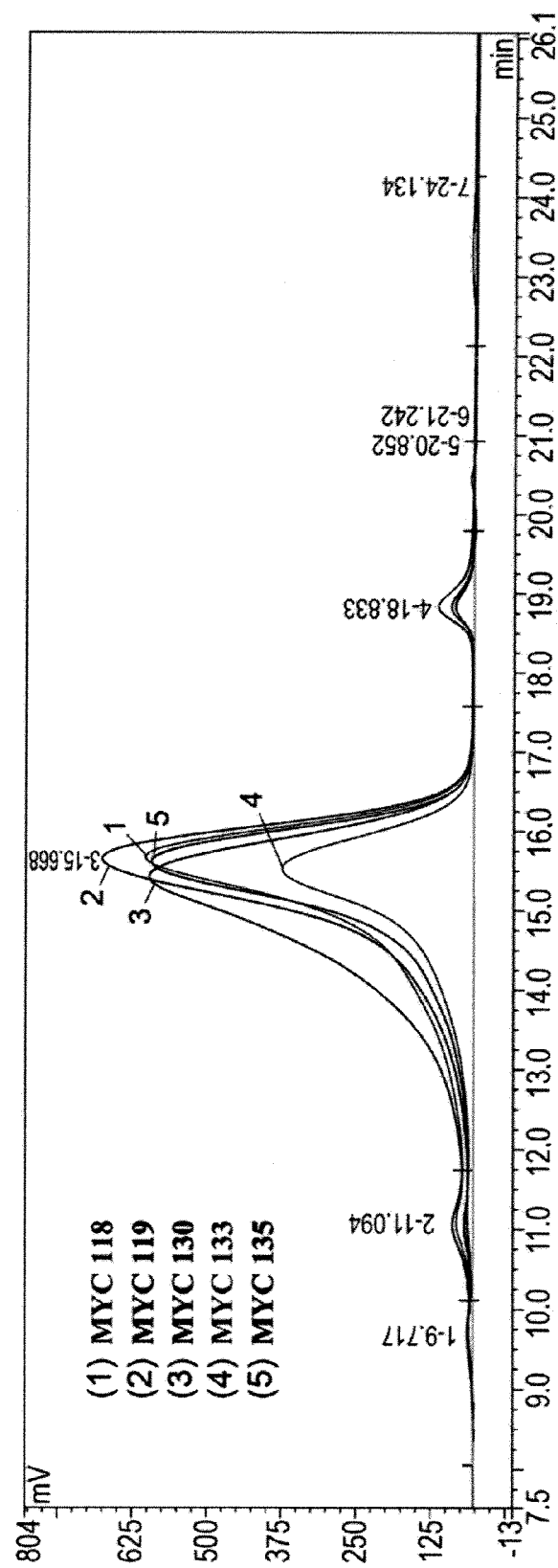
FIG. 18 is an overlay of SEC HPLC 0.5% NLS chromatograms of REF.End samples for the mutants Myc 118, Myc 119, Myc 130, Myc 133 and Myc 135. IBs from these mutants were isolated at bench scale.
Figure 19:
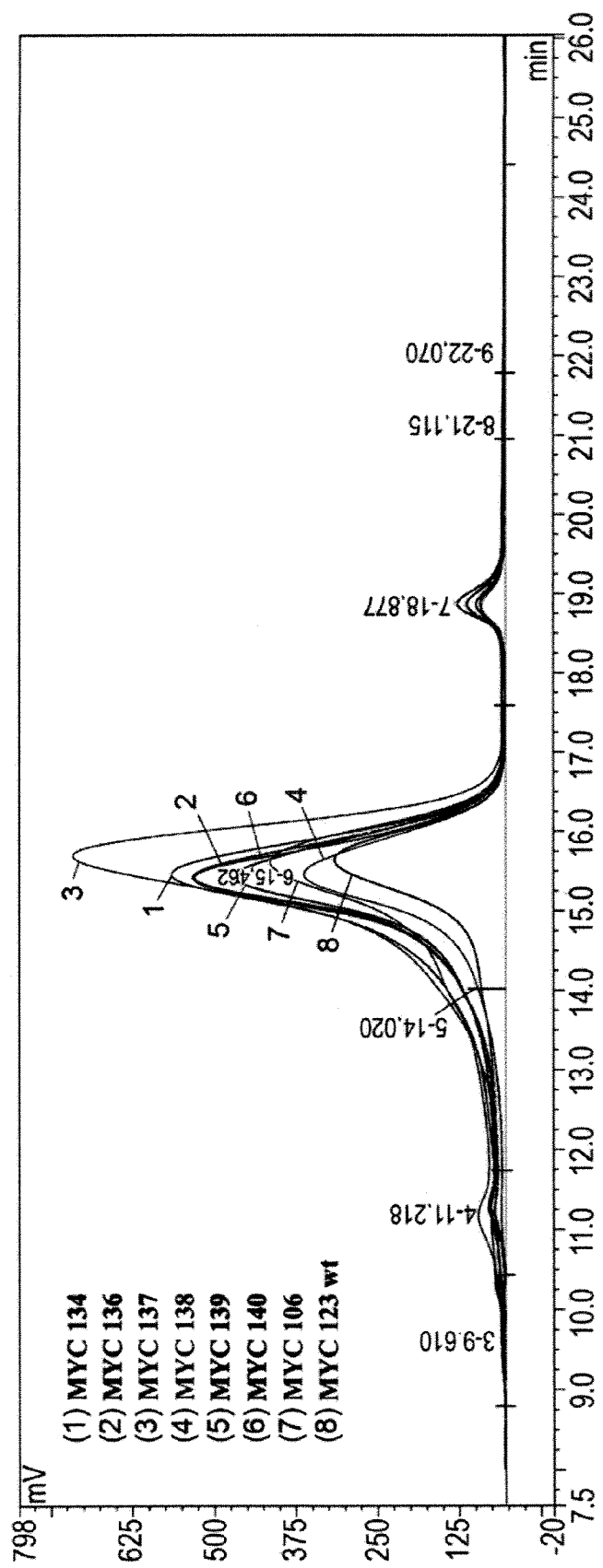
FIG. 19 is an overlay of SEC HPLC 0.5% NLS chromatograms of REF.End samples for the mutants Myc 134, Myc 136, Myc 137, Myc 138, Myc 139, Myc 140, Myc 106 and Myc 123 wild type. IBs from these mutants were isolated in the pilot plant.

In FIG. 18, the elution profile of Myc 130 sticks out because of increased fronting compared with the other investigated samples. This might have been due to increased heterogeneity in the sample because of the construct's nature (more hydrophilic) or due to an accidentally different sample treatment.

Samples shown in FIG. 18 were prepared simultaneously and stored at 4° C. for 5 days prior to analysis. Samples shown in FIG. 19 were prepared simultaneously and stored at 4° C. over night days prior to analysis. Samples seemed to be stable at 4° C. as MW of the constructs were in a similar range.

Fronting of Myc 130 may have beem due to higher amount of aggregated species compared with the other investigated samples. However, peak 2 in the corresponding RPC 2 chromatogram was not outstandingly large but it has been observed that there is only sometimes a correlation between increased MW determined by SEC 0.5% NLS and large peak 2 peak area, determined with RPC2.

Additionally, SDS-page of Myc 130 did not indicate a higher impurity content and increased heterogeneity of the sample. Other factors leading to fronting in SEC such as column overloading and increased temperature during analysis can be excluded as all samples were analyzed on the same day.

There was a very early retention time for Myc 130 in RPC2.

It was assumed that the average MW in a REF.End sample was increasing for an increasing amount of dimers, aggregates and impurities. The calculated MW of a monomeric Mycograb expressed in the different mutants was between 26 and 27 kDa because of the different linker length and other mutations. A table listing theoretical MW-calculated from the amino acids-, MW of the REF.End sample determined by SEC, # of amino acids, linker length and number of cysteines is given in Table 9.

TABLE 9

SEC-HPLC 0.5% NLS results of REF.End samples from all tested mutants. The mutants are ranked according to their theoretical molecular weight.

| MUTANT | MW theory | SEC | # aa | Linker length | Number of cysteines |
|---|---|---|---|---|---|
| MYC 130 | 26.1 | 65.8 | 246 | 3X | 4 |
| MYC 118 | 26.4 | 48.6 | 251 | 4X | 5 |
| MYC 137 | 26.466 | 47.1 | 251 | 4X | 4 |
| MYC 119 | 26.5 | 49.9 | 252 | 4X | 5 |
| MYC 140 | 26.55 | 49.3 | 252 | 4X | 4 |
| MYC 133 | 26.7 | 57.9 | 256 | 5X | 5 |
| MYC 138 | 26.78 | 51.0 | 256 | 5X | 4 |
| MYC 135 | 26.8 | 52.2 | 257 | 5X | 5 |
| MYC 136 | 27.018 | 64.6 | 261 | 6X | 5 |
| MYC 134 | 27.062 | 62.6 | 261 | 6X | 5 |
| MYC 139 | 27.09 | 64.7 | 261 | 6X | 4 |
| MYC 123Wt | 27.32 | 63.5 | 256 | 3X | 5 |
| MYC 106 origami | 27.38 | 61.5 | 256 | 3X | 4 |

Theoretical MW was plotted versus MW determined by SEC and a linear relationship with a correlation coefficient of 0.77 was found when the data point for Myc 130 was excluded.

Figure 20:
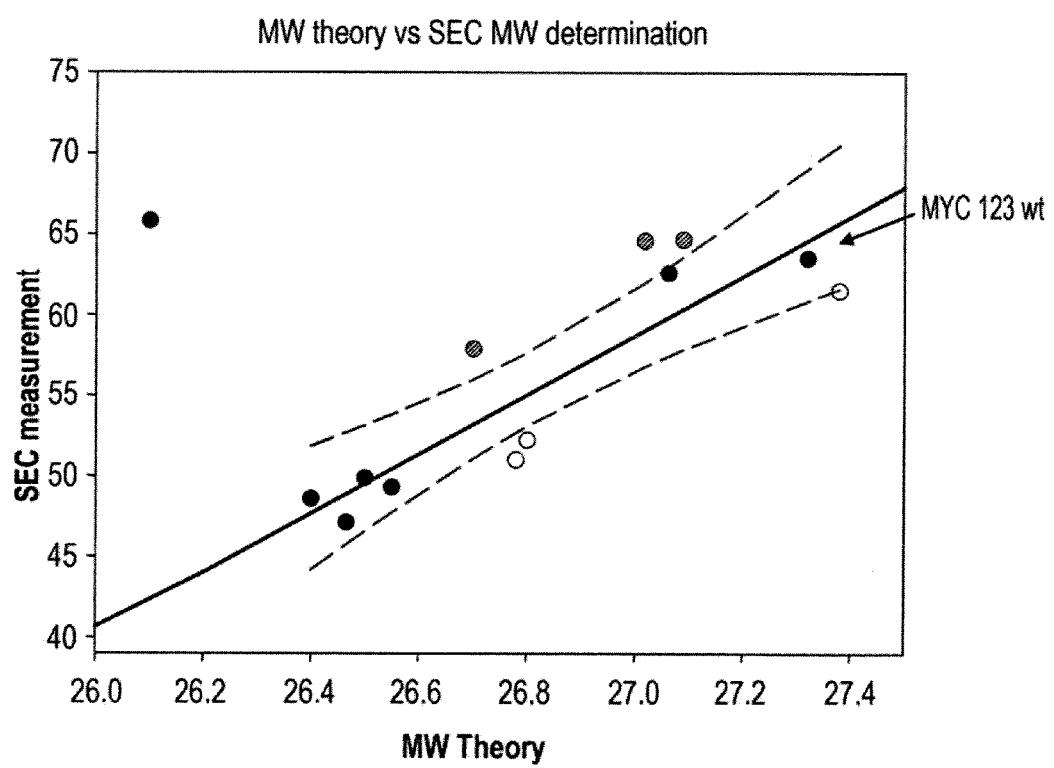
FIG. 20 shows a scatter plot and linear regression (continuous line) of measured MW versus theoretical MW of REF.End samples for all mutants. The 95% confidence interval for the fit is also shown (dashed line). The dot at top left shows MYC 130. The dots within the dashed lines are within the 95% CI and therefore not significantly different from the wildtype. The dots below both dashed lines represent mutants with lower average MW than predicted and the dots above both dashed lines represent mutants where a higher average MW was measured than predicted.

Mutants Myc 106, Myc 138 and Myc 135, represented by dots to the right of the lower dashed line in FIG. 20, had a lower average MW than the wild type. Mutants Myc 133, 136 and 139, represented by dots to the left of the higher dashed line had a higher average MW than the wild type. However, assay variability has to be taken into account. Additionally, from FIG. 19 it can be seen that the mass of injected protein was not always the same as peak area for some of the samples. Formation of covalent aggregates should be decreased for mutants with 4 cysteines as compared with Mycograb with 5 cysteines because no free cysteine in mutants with 4 cysteines is available after formation of intermolecular SS bridges. Intermolecular covalent aggregates are formed during refolding even with a mutant with only 4 cysteines but it would be likely that the amount is lower than for a mutant with 5 cysteines.

Example 11

SEC Formulation: NLS removal by UF/DF from Refolding Solution to Measure Aggregation Tendency In order to evaluate aggregation tendency of Mycograb mutants, the NLS concentration was lowered by an average factor of 5 from the REF.End solution with ultra/diafiltration using a stir cell. The total buffer volume used during diafiltration divided by the retentate volume is the diafactor and was 2.5.

The rationale of this experiment was to investigate aggregation tendency of the mutants when the dissolving agent NLS is lowered to a concentration at which aggregation cannot be prevented anymore.

It was assumed that formation of aggregates can be assessed with SEC-HPLC formulation. The elution buffer contained 0.5M urea buffer but no NLS to suppress aggregation.

Increase in molecular weight was used as a measure of tendency to aggregate and allows the mutants to be compared.

Mutants Myc 137, Myc 106, Myc 119 and the wild type Myc 123 were selected for a first set of experiments. Table 10 shows the molecular weight (MW) in kDa determined by SEC—HPLC running in formulation buffer and concentration of NLS (%) determined by RP-HPLC for REF.End samples from mutants MYC 119, 137, 106 and MYC 123 before and after UFDF. The NLS reduction factor was calculated from NLS concentration in the sample prior to UFDF (# 2) divided by the concentration of NLS after UFDF (#3). The % increase MW based on SEC HPLC 0,5% NLS was calculated from the MW of the .REF.END sample (#1) and the MW after UFDF (#3) for the respective Mutant.

TABLE 10

| Sample no. | Sample code | MYC 123 MW [kDa] | c NLS % | MYC 119 MW [kDa] | c NLS % | MYC 106 origami MW [kDa] | c NLS % | MYC 137 MW [kDa] | c NLS % |
|---|---|---|---|---|---|---|---|---|---|
| #1 | REF. END* | 63.5[] | n.d | 49.3[] | n.d | 61.5 [kDa][] | n.d | 47.1[] | n.d |
| #2 | Prior to UFDF | 214 | 0.52 | 359 | 0.58 | 202 | 0.607 | 212 | 0.57 |
| #3 | After YFDF | 178 | 0.08 | 245 | 0.171 | 184 | 0.132 | 194 | 0.114 |
|  | NLS reduction factor |  | 6.5 |  | 3.4 |  | 4.6 |  | 5 |
|  | % increase MW based on* | 180% |  | 397% |  | 199% |  | 312% |  |

*The molecular weight was determined with an analytical SEC HPLC method containing 0.% NLS in the running buffer (SEC HPLC 0.5% NLS).
[**]data from Table 9.

The apparent high molecular weight determined by SEC HPLC (running with formulation buffer) of the sample prior to UFDF was due to aggregation of protein during analysis.

The sample prior to UFDF still contained 0.5% NLS. As the sample migrated through the column, NLS was more strongly retarded than the protein and consequently aggregation occurred. Therefore this analytical method was not suited to determine molecular weight of samples containing NLS.

In order to determine molecular weight of Mycograb in the REF.End sample, SEC HPLC with 0.5% NLS in the running buffer was used. The increase in MW after removal of NLS in the REF.End sample by UFDF was calculated as described above in relation to Table 10. Values are shown in row 6 of Table 10. MYC 123 showed the smallest increase in MW whereas MYC 119 had the strongest increase, 400%.

MYC 123 has a lower aggregation tendency than MYC 119 based on these data. However, it has to be considered that the analytical SEC HPLC may have an influence on the protein structure and on the formation of aggregates. Moreover, increase of MW is calculated from data obtained from two different analytical methods and it cannot be assessed if the MW of a sample is similar when it is determined with the two different methods.

In Table 11, the mutants are ranked according to increase in MW after NLS removal together with the mutations. It has to be noted that the two mutants with a 3× linker element have significantly lower % of MW increase compared with mutants with a 4× linker element.

TABLE 11

Increase of molecular weight after removal of NLS by UFDF for the 4 investigated mutants.

| MUTANT | % molecular weight increase | HIS tag | Linker length | VH-VL alignment | cysteins |
|---|---|---|---|---|---|
| MYC 123 Wt | 180 | YES | 3X | VH N-terminal | 5 |
| MYC 106 origami | 199 | YES | 3X | VH N-terminal | 4 |
| MYC 137 | 312 | NO | 4X | VH N-terminal | 4 |
| MYC 119 | 397 | NO | 4X | VL N-terminal | 5 |

Figure 21:
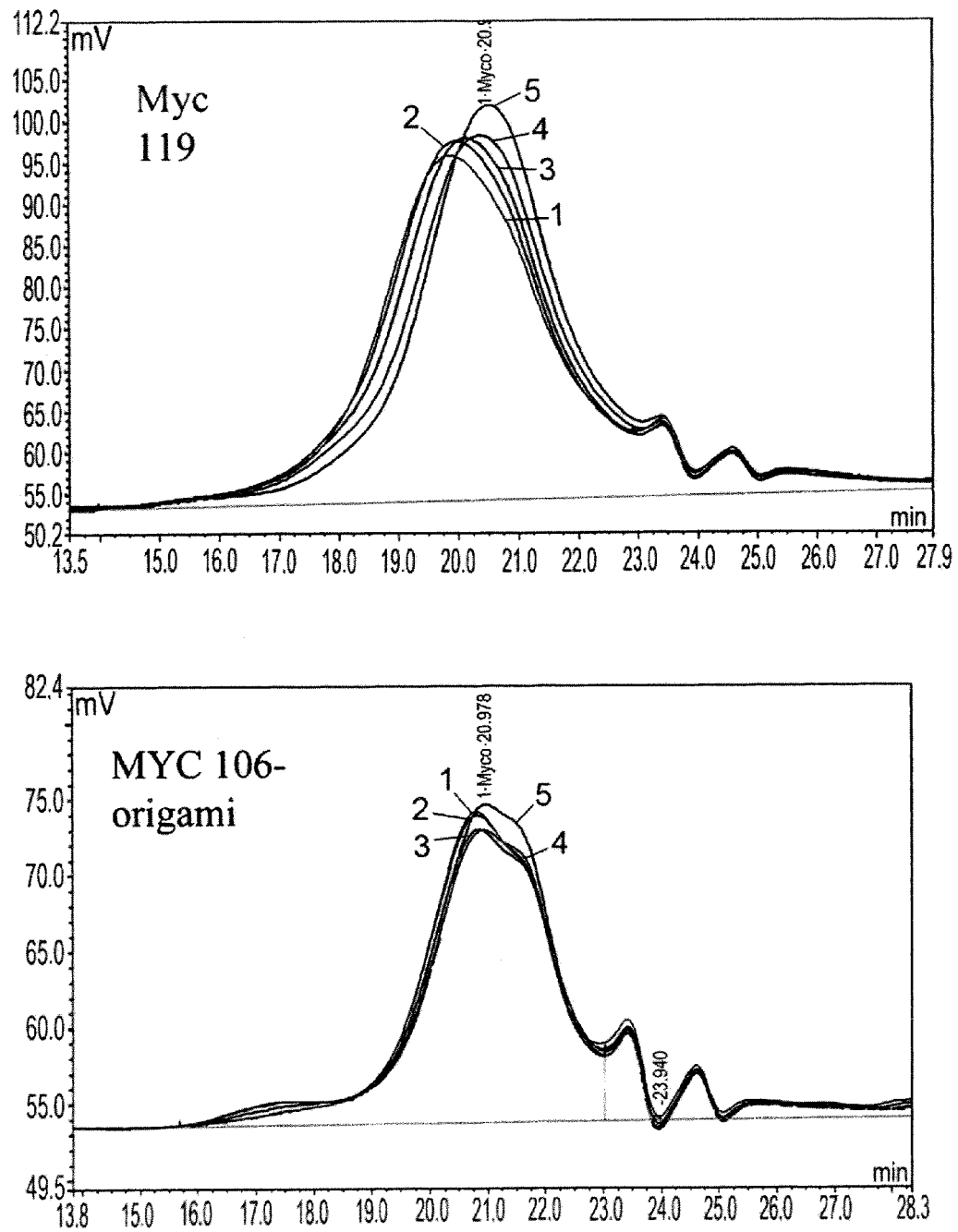
FIG. 21 shows SEC-HPLC (formulation) chromatograms for REF.END samples of Myc 119, Myc 106-origami, Myc 123 wt and Myc 137 after UFDF against 50 mM Tris, pH 9.0 buffer. Samples were taken after each volume reconstitution. Sample prior to UFDF treatment (5), after $1^{st}$ buffer exchange step (2), $2^{nd}$ buffer exchange step (3), $3^{rd}$ (4) and last (5) step.
Figure 21:
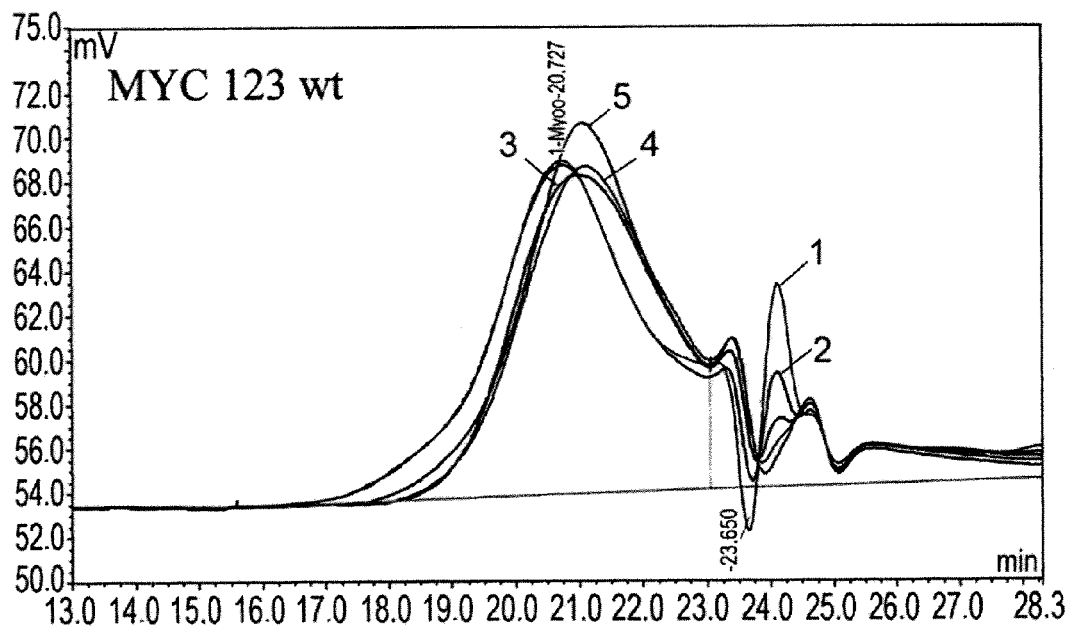
Figure 21:
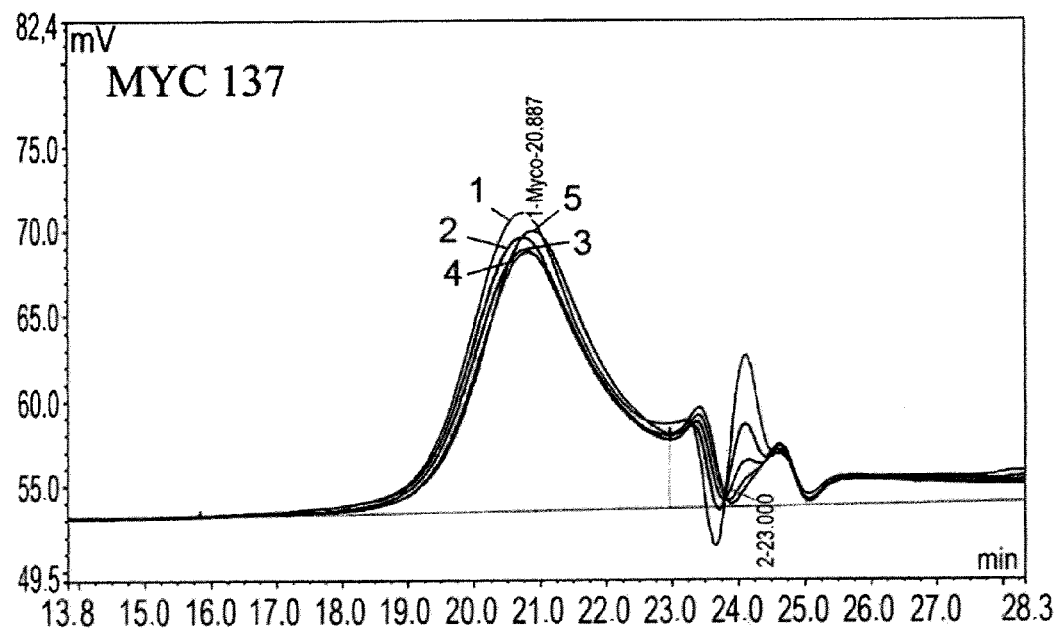
Figure 22:
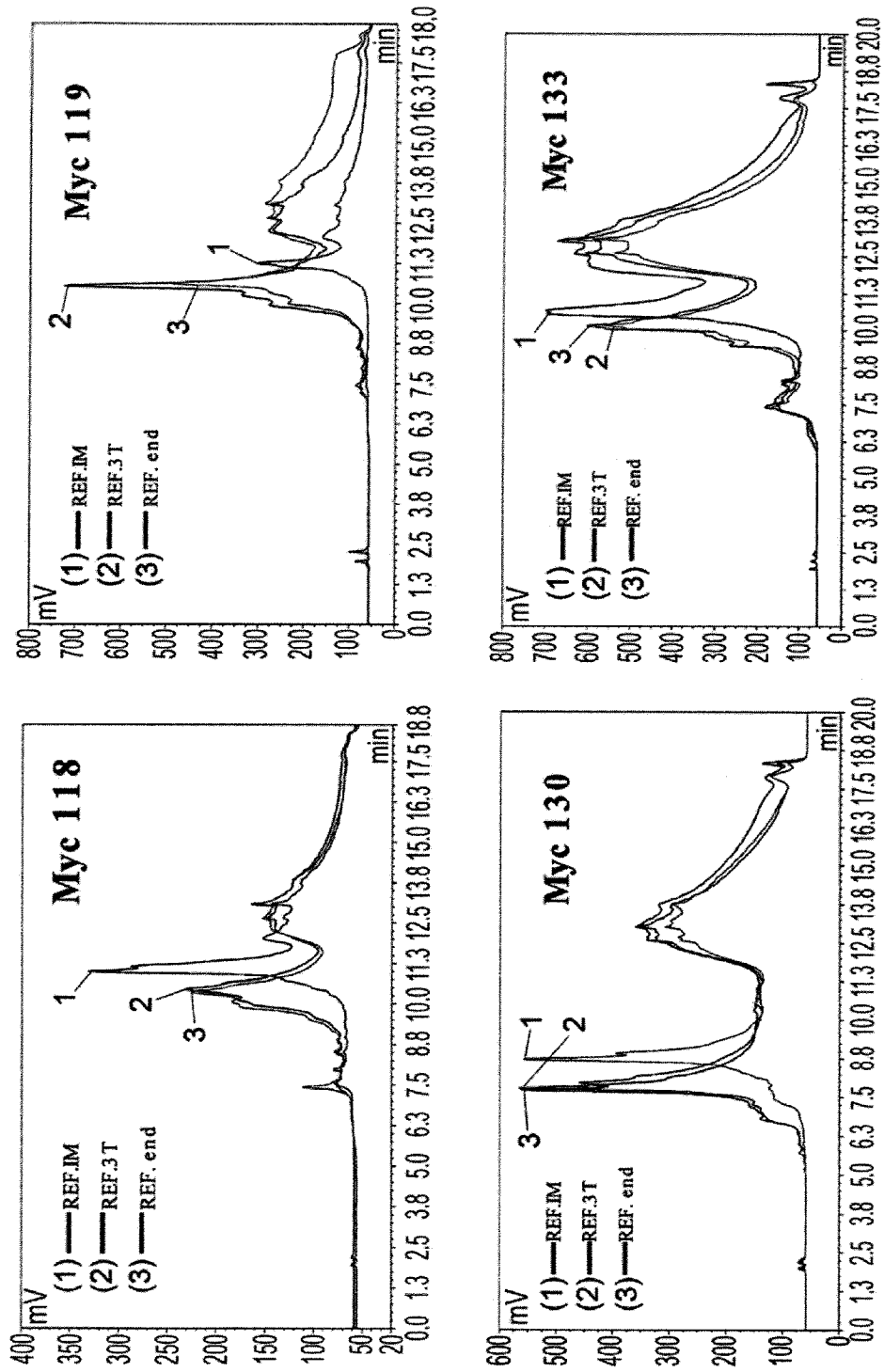
FIG. 22 shows RP-HPLC 2 chromatograms of REF.IM, REF.3T and REF. END samples for all tested mutants.
Figure 22:
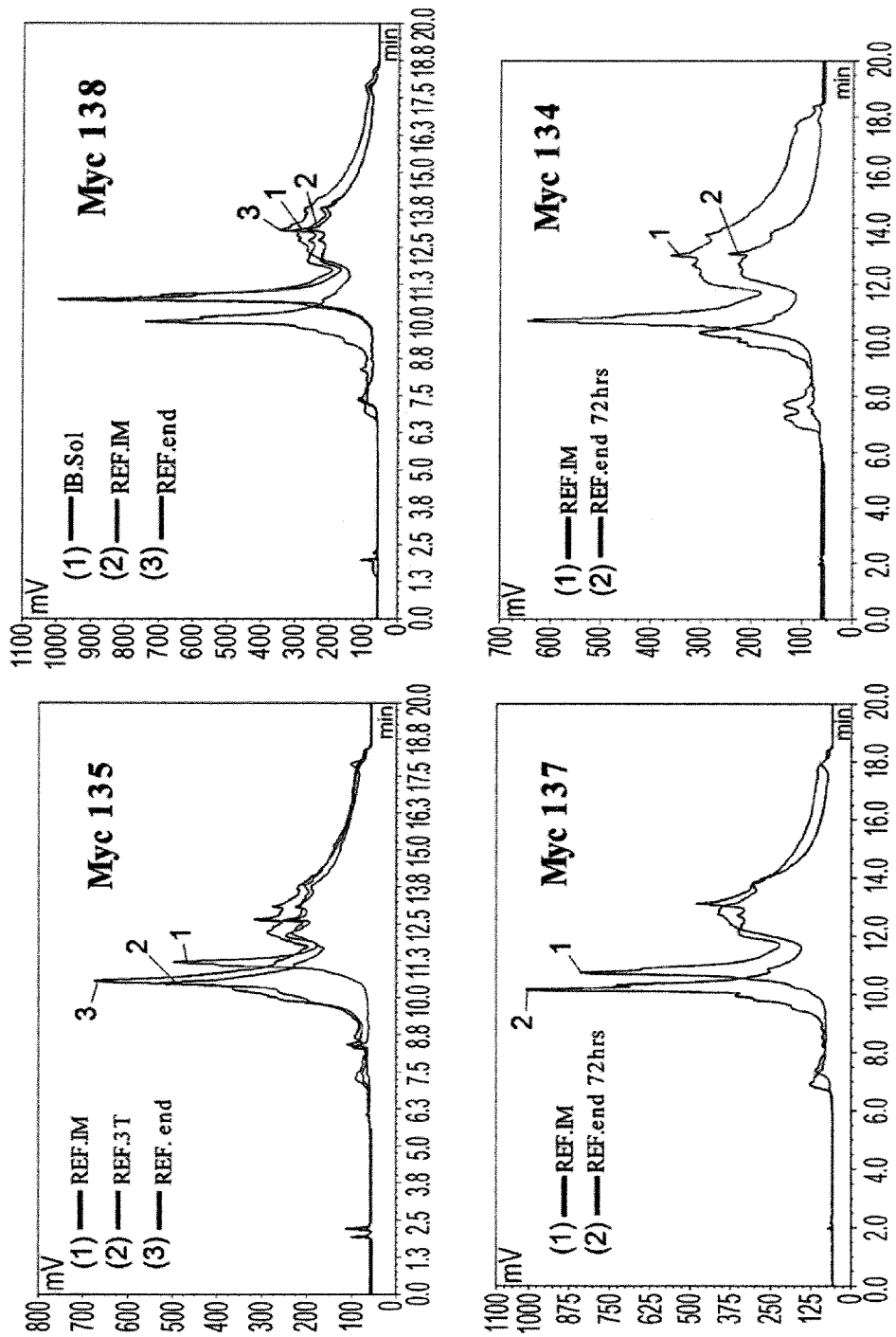
Figure 22:
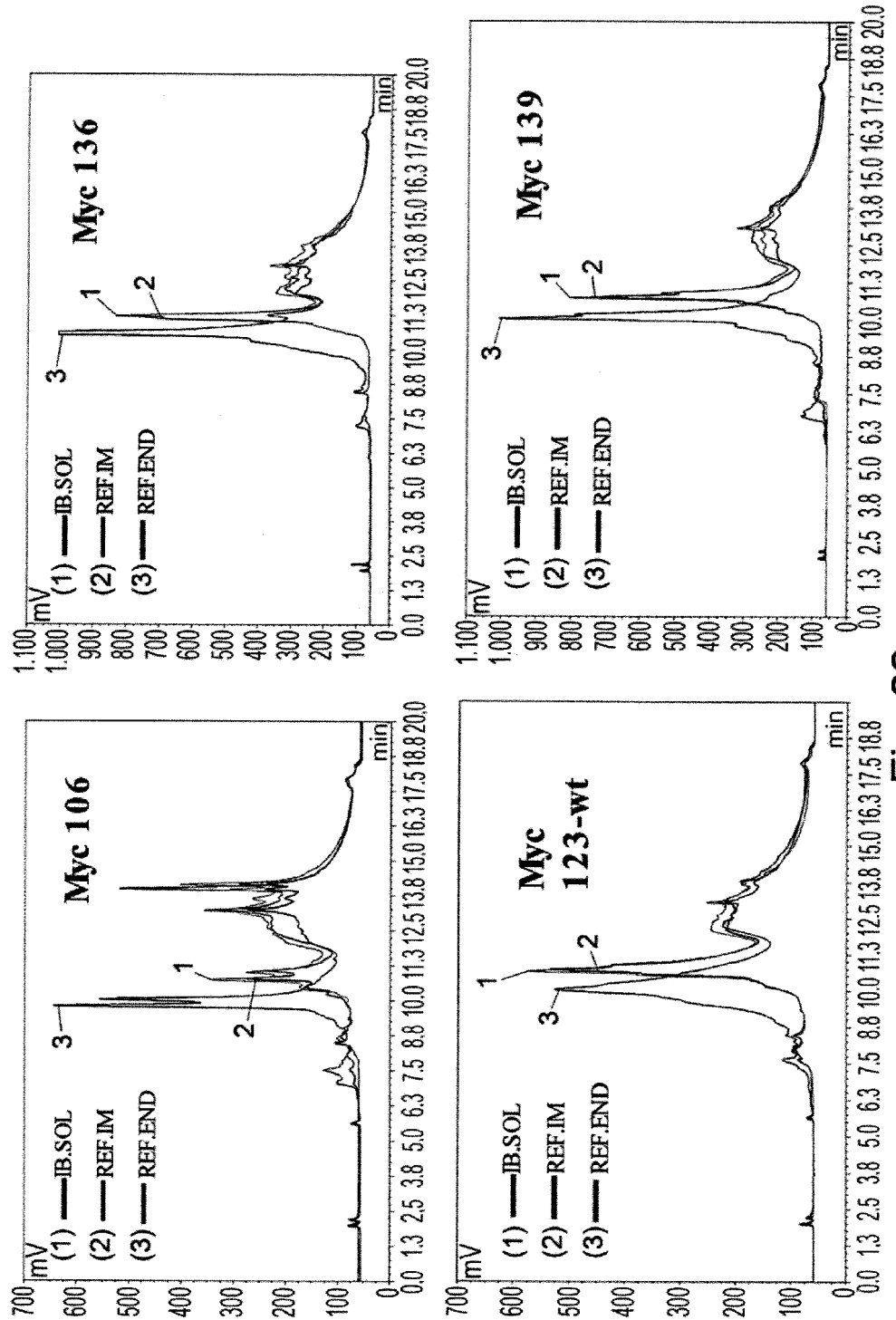
Figure 22:
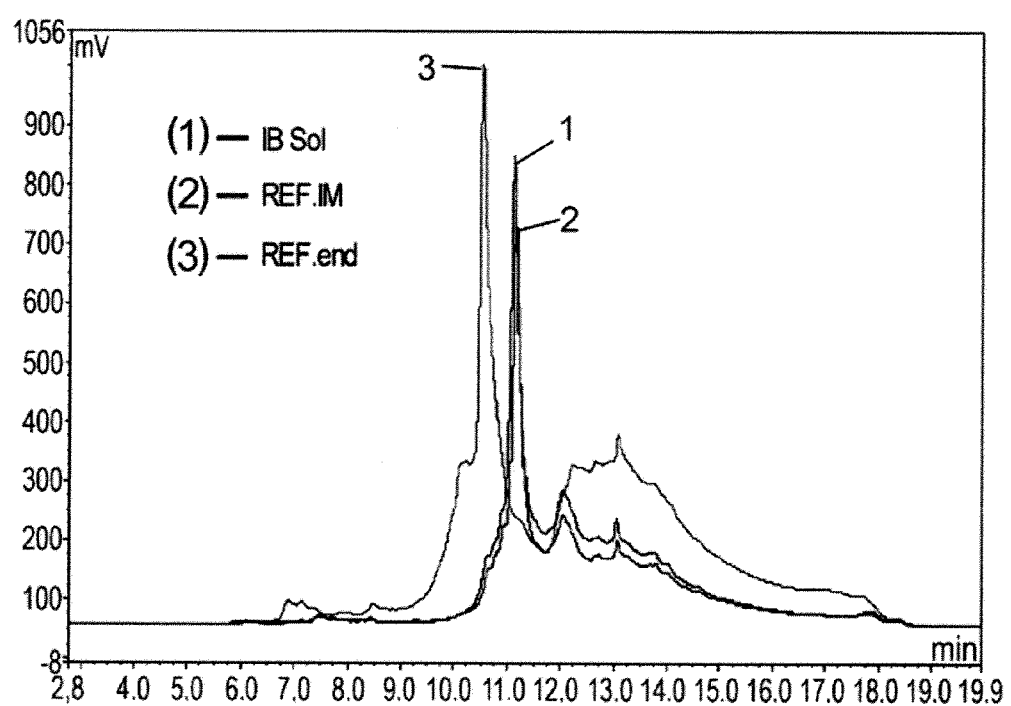

FIG. 21 shows an overlay of the SEC HPLC chromatograms obtained from the sample prior to UFDF and after each volume reconstitution. The shape of the elution peaks did not significantly change with reduction of NLS concentration. Consequently, the MW of the sample also remained constant with reduction of NLS. This might be an indication that there is a limit in the concentration of surfactant below which aggregation is initiated but does not proceed further. However, the impact of the analytical method on the MW of the sample is not known and may be the reason why all samples have similar MW.

The NLS concentration was reduced on average (n=5) to a concentration of 0.124% after 5 volume reconstitutions, corresponding to a diavolume of 2.5. Theoretically, for a retention R=0 of NLS, the calculated remaining NLS concentration should be 0.020%. Equation 3 was used for calculation of the theoretical remaining NLS concentration:

$$c_{retentat}=c_{feed}\times(e^{(R-1)\times[INVCF+N]}) \qquad \text{equ. 3}$$

where $C_{retentat}$ is the concentration of NLS in the retentate, $c_{feed}$ is the concentration of NLS in the feed solution. R is the retention, the fraction of solute that is retained by the membrane. VCF is the volume concentration factor and N is the diavolume which is the total buffer volume introduced to the operation during diafiltration divided by the retentate volume.

The discrepancy between the theoretical and the measured concentration of NLS in the retentate is an indication for retention of NLS by the membrane greater than 0. This might be due to interaction between NLS and the protein, membrane and/or other components. The ability to deform can also cause unwanted retention.

Example 12

Pep-Map Analysis

REF.End samples of all mutants were analyzed for disulfide bridging with peptide map. Prior to analysis, the sample was alkylated with iodoacetamide, digested with trypsin and subjected to LC-MS. UV peaks of the single peptides were identified with mass spectrometry. The peptides with free SH groups, correctly and incorrectly formed S—S bonds as well as dimeric peptides were, whenever possible, semi-quantitatively determined.

A correctly folded construct with 5 cysteines forms an S—S bond between Cys 23 and Cys 97 which corresponds to T3 and T9 respectively. The bond T3-T9 is located in the light chain. The other disulfide bond is on the heavy chain between Cys 159 and Cys 224, corresponding to T12 and T17. The 5th cysteine is located at Cys28 and corresponds to the T4 peptide.

A construct with 4 cysteines always lacks the Cys 28 residue, the correct S—S bridges are similar as for a construct with 5 cysteines.

Mutants 118, 119, 130, 135, 133, 134, 137 and C28Y+HIS (106) as well as C28Y−HIS (108) were analyzed in lab AL1. Mutants 106 origami, 136, 138, 139, 140 and the wild type 123 were analyzed in analytical lab AL2 with a different device. The sensitivity of the mass spectrometer in AL1 is higher than that in AL2 and therefore, a semi-quantitative analysis of mutants analyzed in AL2 could not be obtained. However, it was possible to determine if correctly formed SS bridges are present.

A summary of the obtained data is given in Table 12. The results are compiled in 3 categories: free SH, bridged cysteines and dimeric cysteines. Free cysteines indicate a SH group that did not form a disulfide bond. Bridged cysteines are intramolecular disulfide bonds and dimeric cysteines represent intermolecular disulfides. W indicates that a weak signal for the respective peptide was detected and X represents peptides giving strong signals. Mutants analyzed in AL 2 are labeled with *.

TABLE 12

Pep Map analysis of all tested mutants

| | | Mutants with 5 cysteins | | | | | | Mutants with 4 cysteins | | | | | | | |
|---|---|---|---|---|---|---|---|---|---|---|---|---|---|---|---|
| | | Myc 118 | Myc 119 | Myc 133 | Myc 134 | Myc 135 | Myc 123* | Myc 106* origami | Myc 130 | Myc 137 | Myc 138* | Myc 139* | Myc 140* | Myc 106 (C28Y + HIS) | Myc 108 (C28Y − HIS) |
| Free | Free SH at T4 | w | w | w | | | | no T4! | | | | | | | |
| cysteins | All other free SH | w | w | w | w | w | X | | | | | | | | |
| bridged | correct disulfides | | | | | | | | | | | | | | |
| cysteins | T3-T9 | w | w | w | | w | | | X | X | | | | X | X |
| | T12-T17 | X | X | X | | | | | | X | | | | X | X |
| | incorrect disulfides | | | | | | | | | | | | | | |
| | all other combinations | X | X | X | X | X | X | X | X | X | X | w | X | X | X |

TABLE 12-continued Pep Map analysis of all tested mutants

| | | Mutants with 5 cysteins | | | | | Myc | Mutants with 4 cysteins | | | | | Myc 106 | Myc 108 |
|---|---|---|---|---|---|---|---|---|---|---|---|---|---|---|
| | | Myc 118 | Myc 119 | Myc 133 | Myc 134 | Myc 135 | Myc 123* | 106* origami | Myc 130 | Myc 137 | Myc 138* | Myc 139* | Myc 140* | (C28Y + HIS) | (C28Y − HIS) |
| Dimers | T9-T9 | X | | w | w | | | | X | w | | | | w | w |
| | other dimers | | | | | | w | | | | | | | | |

A 'correctly' folded Mycograb with 5 cysteines should give a significant signal for free SH at the T4 peptide and no signal corresponding to other free SH groups. Additionally, a strong signal for the correct disulfides T3-T9 and T12-T17 is expected and incorrect SS bonds should not be present. Lastly, no intermolecular SS bonds should be present.

A 'correctly' folded Mycograb with 4 cysteines should not have any free SH groups. Only the correct S—S bonds T3-T9 and T12-T17 should be detected. Additionally, no intermolecular SS bonds should be present.

Table 12 shows that neither the wild type nor any of the mutants gave strong signals for the correct S—S bonds only. It has to be considered that the REF.End sample consists of a population of differently folded and covalently aggregated species, so that a mixture of all possible combinations of disulfide bonds and free SH groups is present. However, a promising mutant should at least show significant signals for both of the correct S—S bridges which is the case for MYC 137 and the mutants C28Y+HIS and C28Y−HIS.

In 5 cases, only incorrect S—S bonds were found, where no, or only a weak, signal was obtained for the correct disulfide bonds.

Signals for MYC 123, MYC 138, MYC 139 and MYC 140 were extremely weak and reanalysis of the samples did not yield higher signals. Though Mycograb specific peptides were found, the cysteine containing peptides gave no or only a weak signal. This might be due to ineffective digestion of the respective portion of the protein with trypsin because of structurally blocked cleaving sites. It was also noted that mutants with increased linker length (5 and 6× instead of 3×) were more difficult to digest and consequently signals for the late eluting peptides could not or could only hardly be detected.

Interestingly, covalent disulfides were, with one exception, only formed between the two T9 peptides, corresponding to Cys 97 residues.

Mutants Myc 118, 119, 130, 133, 137 and the mutants C28Y+HIS and C28Y−HIS gave stronger signals for correct S—S bonds than the wild type. However, it has to be considered that Myc 123 was analyzed with a different mass spectrometer of lower sensitivity and hence signal intensities cannot be compared. Signals from peptides of Myc 123 can be compared with signals from mutants 106 origami, 136, 138, 139 and 140. For none of these constructs, correct disulfide bridges were obtained. Only signals for incorrect disulfides were found.

Pep Map results for Myc 137, Myc C28Y+HIS and Myc C28Y−HIS were most promising with significant signals for both correct disulfide bridges. Mutants Myc 118, Myc 119 and Myc 133 also showed a certain amount of native like disulfide bridging, however, the signal for T12-T17 was weak.

Mutant Myc 130 showed strong signals for the T12-T17 SS bond, but the second correct disulfide was not found.

CONCLUSIONS

Correlations of Analytical Results

The best recoveries after refolding were obtained with the MYC 123 (wt) and MYC 134, as determined by the titer assay with Poros column (RPC 1).

The solubilization of IBs with chaotropic agents was faster than solubilization with NLS. RPC 2 chromatograms of IBs solubilized with urea or NLS were comparable. However, SDS Page indicated a stronger dissolving power of NLS as the aggregate smear was reduced compared with IBs solubilized with urea, see FIG. 14.

Refolding after solubilization with chaotropic agents by dilution and use of different additives such as Cysteine, L-Arginine, 1% NLS and low concentration of urea/GuHCl did not show a monomeric peak in RPC 2, see FIG. 12 and FIG. 13. The protein completely aggregated which was confirmed by SDS Page, non reducing and the RPC 2 chromatogram showed a huge peak 2.

The determination of MW with SEC HPLC 0.5% NLS correlated with an $R^2$ of 0.77 with the theoretically calculated MW when 1 outlier was excluded. The resolving power of SDS PAGE was not sufficient to detect all subtle differences in MW, but a migration time difference was seen between two mutants of a MW differing by 0.6 kDa in theory and 14 kDa as measured with SEC HPLC (MYC 134 and MYC 118, respectively).

RPC 2 chromatography was able to confirm decreased hydrophobicity of a mutant where 10 hydrophobic amino acids were replaced by more hydrophilic ones (MYC 130). The linker element did not have easy access to binding sites of the stationary phase and did not therefore have influence on retention behavior. It was also observed that Pep Map analysis for constructs with increased linker length gave weaker signals for the peptides of interest compared with constructs with shorter linker. It appeared that the linker element was not easily accessible for the digesting enzyme.

RPC2 chromatograms for MYC 137, 138 and 139 showed the sharpest peak which is attributed to a Mycograb Monomer compared with the other tested mutants, indicating increased homogeneity of the sample.

Pep Map analysis showed that almost no free SH group was present in REF.End samples for mutants with 4 Cysteines. This indicates an almost complete formation of disulfide bridges (incorrect and correct ones) as well as formation of covalent aggregates. For mutants with 5 cysteines, weak signals were obtained for various free SH groups but only mutants Myc 118, Myc 119 and Myc 133 had a free SH group at T4, the location of the 5th cysteine which should remain reduced in the 'native.' monomer. This is an indication that the SH group on the T4 peptide preferably forms SS bonds because all mutants with 5 cysteines gave signals for free SH groups but only in 3 of them a free SH group at T4 was detected.

MW determined with SEC HPLC is very dependent on the buffer matrix in the sample. A couple of SEC HPLC methods had to be established with a running buffer similar to the buffer of the sample. The matrix dependency of MW determination makes comparison of MW across process steps difficult (Table 10).

The UFDF experiment showed that NLS is to some extent retained in the sample solution and cannot efficiently be removed.

The results obtained with Pep Map of Mutants MYC C28Y+HIS, C28Y–HIS and MYC 137 were particularly promising. The results indicate that a mutant with a HIS tag and only 4 cysteines is particularly preferred. The HIS tag is required for purification with IMAC, a purification step of high efficiency. A construct with only 4 cysteines is more likely to form correct disulfides and covalent aggregates.

Effects of Mutations

The most beneficial effect of the mutations can be attributed to the removal of the 5th cysteine. The number of correct disulfide bonds was increased compared with constructs with 5 cysteines. Additionally, solubility of the IBs was enhanced compared with constructs with 5 cysteines.

Exchanging the orientation of the heavy and light chain fragment had a minor effect on retention time in RPC 2 where the retention time decreased when the VL element was C terminal compared with an N-terminal orientation.

The tendency of the peptides to aggregate after NLS removal may be increased with the number of linker elements.

The invention claimed is:

1. A purified scFv peptide comprising a VH domain and a VL domain linked by an amino acid spacer, wherein the $V_H$ domain comprises the amino acid sequence set forth as SEQ ID NO: 64 and the $V_L$ domain comprises the amino acid sequence set forth as SEQ ID NO: 66, and wherein the scFv peptide comprises a substitution of an amino acid in the $V_H$ domain at the position corresponding to $C_{28}$ of SEQ ID NO: 64.

2. The scFv peptide according to claim 1, wherein the substitution of the amino acid in the VH domain is $C_{28}Y$.

3. The scFv peptide according to claim 1, wherein the substitution of the amino acid in the $V_H$ domain is $C_{28}S$.

4. The scFv peptide according to claim 1, further comprising a purification tag.

5. A purified scFv peptide comprising the amino acid sequence selected from the group consisting of SEQ ID NO:8, 10 and 14, wherein Xaa denotes an amino acid residue other than cysteine and wherein the N-terminal methionine residue may optionally be cleaved off.

6. A pharmaceutical composition comprising the scFv peptide according to claim 1 in combination with a pharmaceutically acceptable excipient, diluent or carrier.

7. The pharmaceutical composition of claim 6 further comprising an antifungal agent.

8. The pharmaceutical composition according to claim 7, wherein the antifungal agent is selected from the group consisting of an azole antifungal agent, a polyene antifungal agent, and an echinocandin antifungal agent.

9. The scFv peptide according to claim 1, wherein the amino acid spacer comprises the sequence (GGGGS)n, and wherein the integer n is 1 to 12.

10. A pharmaceutical composition comprising the scFv peptide according to claim 9 in combination with a pharmaceutically acceptable excipient, diluent or carrier.

11. A purified scFv peptide comprising the amino acid sequence as set forth as SEQ ID NO: 10, wherein Xaa is tyrosine or serine aid wherein the N-terminal methionine residue may optionally be cleaved off.

12. The scFv peptide of claim 11, wherein said scFv peptide is encoded by a nucleic acid sequence having $(taa)_2$ located at the 3' end of said nucleic acid sequence.

13. The scFv peptide of claim 11, wherein Xaa is serine.

14. The scFv peptide of claim 11, wherein Xaa is tyrosine.

15. The purified peptide according to claim 11, consisting of amino acids 2-256 of SEQ ID NO: 10, wherein Xaa is tyrosine.

16. A pharmaceutical composition comprising the scFv peptide of claim 15 in combination with a pharmaceutically acceptable excipient, diluent or carrier.

17. The pharmaceutical composition according to claim 16, further comprising an antifungal agent.

18. The pharmaceutical composition according to claim 17, wherein the antifungal agent is selected from the group consisting of an azole antifungal agent, a polyene antifungal agent, and an echinocandin antifungal agent.

* * * * *

SEQUENCE LISTING

<160> NUMBER OF SEQ ID NOS: 71

<210> SEQ ID NO 1
<211> LENGTH: 771
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(771)

<400> SEQUENCE: 1

```
atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt tgc atc atc tct      96
Gly Glu Ser Leu Arg Ile Ser Cys Lys Gly Ser Gly Cys Ile Ile Ser
            20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
    50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
65                  70                  75                  80 gct tac ctg caa tgg aac agc ctg aaa gcg agc gac acc gcg atg tac     288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg     336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt     384
Gly Gln Gly Thr Leu Val Thr Val Ser Ser Gly Gly Gly Gly Ser Gly
        115                 120                 125 ggt ggc ggc agc ggc ggc ggc agc gat gtt gtg atg acc cag agc         432
Gly Gly Gly Ser Gly Gly Gly Gly Ser Asp Val Val Met Thr Gln Ser
    130                 135                 140 ccg agc ttc ctg agc gcg ttc gtt ggt gac cgt atc acc att acc tgc     480
Pro Ser Phe Leu Ser Ala Phe Val Gly Asp Arg Ile Thr Ile Thr Cys
```

```
                                                    -continued
145                 150                 155                 160
cgc gcc agc agc ggc atc agc cgc tat ctg gcg tgg tat cag caa gca      528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa      576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc      624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac      672
Thr Leu Thr Ile Asn Ser Leu Gln Pro Glu Asp Phe Ala Thr Tyr Tyr
    210                 215                 220 tgc caa cac ctg aat agc tat ccg ctg acc ttc ggt ggc ggc acc aaa      720
Cys Gln His Leu Asn Ser Tyr Pro Leu Thr Phe Gly Gly Gly Thr Lys
225                 230                 235                 240 gtg gac atc aaa cgc gcg gcc gca ctc gag cac cac cac cac cac cac      768
Val Asp Ile Lys Arg Ala Ala Ala Leu Glu His His His His His His
                245                 250                 255 tga                                                                   771

<210> SEQ ID NO 2
<211> LENGTH: 256
<212> TYPE: PRT
<213> ORGANISM: Artificial
<220> FEATURE:
<223> OTHER INFORMATION: Synthetic Construct

<400> SEQUENCE: 2

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Cys Ile Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Val Val Met Thr Gln Ser
    130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Asn Ser Leu Gln Pro Glu Asp Phe Ala Thr Tyr Tyr
    210                 215                 220
```

```
Cys Gln His Leu Asn Ser Tyr Pro Leu Thr Phe Gly Gly Gly Thr Lys
225                 230                 235                 240

Val Asp Ile Lys Arg Ala Ala Ala Leu Glu His His His His His
                245                 250                 255

<210> SEQ ID NO 3
<211> LENGTH: 774
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(774)

<400> SEQUENCE: 3 atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
1               5                  10                  15 ggt gaa tct ctg cgt atc tct tgc aaa ggt tct ggt tgc atc atc tct      96
Gly Glu Ser Leu Arg Ile Ser Cys Lys Gly Ser Gly Cys Ile Ile Ser
            20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
    50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
65                  70                  75                  80 gct tac ctg caa tgg aac agc ctg aaa gcg agc gac acc gcg atg tac     288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg     336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt     384
Gly Gln Gly Thr Leu Val Thr Val Ser Ser Gly Gly Gly Gly Ser Gly
        115                 120                 125 ggt ggc ggc agc ggc ggc ggc agc gat gtt gtg atg acc cag agc         432
Gly Gly Gly Ser Gly Gly Gly Gly Ser Asp Val Val Met Thr Gln Ser
    130                 135                 140 ccg agc ttc ctg agc gcg ttc gtt ggt gac cgt atc acc att acc tgc     480
Pro Ser Phe Leu Ser Ala Phe Val Gly Asp Arg Ile Thr Ile Thr Cys
145                 150                 155                 160 cgc gcc agc agc ggc atc agc cgc tat ctg gcg tgg tat cag caa gca     528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa     576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc     624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac     672
Thr Leu Thr Ile Asn Ser Leu Gln Pro Glu Asp Phe Ala Thr Tyr Tyr
    210                 215                 220 tgc caa cac ctg aat agc tat ccg ctg acc ttc ggt ggc ggc acc aaa     720
Cys Gln His Leu Asn Ser Tyr Pro Leu Thr Phe Gly Gly Gly Thr Lys
225                 230                 235                 240
```

```
gtg gac atc aaa cgc gcg gcc gca ctc gag cac cac cac cac cac cac    768
Val Asp Ile Lys Arg Ala Ala Ala Leu Glu His His His His His His
            245                 250                 255 taa taa                                                             774
```

<210> SEQ ID NO 4
<211> LENGTH: 256
<212> TYPE: PRT
<213> ORGANISM: Artificial
<220> FEATURE:
<223> OTHER INFORMATION: Synthetic Construct

<400> SEQUENCE: 4

```
Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Cys Ile Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Asp Val Val Met Thr Gln Ser
    130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Asn Ser Leu Gln Pro Glu Asp Phe Ala Thr Tyr Tyr
    210                 215                 220

Cys Gln His Leu Asn Ser Tyr Pro Leu Thr Phe Gly Gly Gly Thr Lys
225                 230                 235                 240

Val Asp Ile Lys Arg Ala Ala Ala Leu Glu His His His His His His
                245                 250                 255
```

<210> SEQ ID NO 5
<211> LENGTH: 756
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(756)

<400> SEQUENCE: 5

```
atg gct gaa gtt caa ctt gtt gaa tct ggt gct gaa gtt aaa aaa ccg    48
```

```
Met Ala Glu Val Gln Leu Val Glu Ser Gly Ala Glu Val Lys Lys Pro
1               5                   10                  15 ggt gaa tct ctg cgt atc tct tgc aaa ggt tct ggt tgc atc atc tct    96
Gly Glu Ser Leu Arg Ile Ser Cys Lys Gly Ser Gly Cys Ile Ile Ser
            20                  25                  30 tct tac tgg atc agc tgg gtt cgt cag atg ccg ggt aag ggc ctg gaa    144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg    192
Trp Met Gly Lys Ile Asp Pro Gly Asp Ser Tyr Ile Asn Tyr Ser Pro
50                  55                  60 agc ttt cag ggc cat gtt acc atc agc gcc gat aaa agc att aac acc    240
Ser Phe Gln Gly His Val Thr Ile Ser Ala Asp Lys Ser Ile Asn Thr
65                  70                  75                  80 gct tac ctg caa tgg aac agc ctg aaa gcg agc gac acc gcg atg tac    288
Ala Tyr Leu Gln Trp Asn Ser Leu Lys Ala Ser Asp Thr Ala Met Tyr
                85                  90                  95 tac tgt gcc cgt ggt ggt cgt gac ttc ggt gat agc ttc gat tac tgg    336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt    384
Gly Gln Gly Thr Leu Val Thr Val Ser Ser Gly Gly Gly Gly Ser Gly
        115                 120                 125 ggt ggc ggc agc ggc ggc ggc agc gat gtt gtg atg acc cag agc        432
Gly Gly Gly Ser Gly Gly Gly Gly Ser Asp Val Val Met Thr Gln Ser
130                 135                 140 ccg agc ttc ctg agc gcg ttc gtt ggt gac cgt atc acc att acc tgc    480
Pro Ser Phe Leu Ser Ala Phe Val Gly Asp Arg Ile Thr Ile Thr Cys
145                 150                 155                 160 cgc gcc agc agc ggc atc agc cgc tat ctg gcg tgg tat cag caa gca    528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa    576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc    624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac    672
Thr Leu Thr Ile Asn Ser Leu Gln Pro Glu Asp Phe Ala Thr Tyr Tyr
210                 215                 220 tgc caa cac ctg aat agc tat ccg ctg acc ttc ggt ggc ggc acc aaa    720
Cys Gln His Leu Asn Ser Tyr Pro Leu Thr Phe Gly Gly Gly Thr Lys
225                 230                 235                 240 gtg gac atc aaa cgc gcg gcc gca ctg gaa taa taa                    756
Val Asp Ile Lys Arg Ala Ala Ala Leu Glu
                245                 250

<210> SEQ ID NO 6
<211> LENGTH: 250
<212> TYPE: PRT
<213> ORGANISM: Artificial
<220> FEATURE:
<223> OTHER INFORMATION: Synthetic Construct

<400> SEQUENCE: 6

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Cys Ile Ile Ser
            20                  25                  30
```

```
Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Ser Gly Gly Gly Ser Asp Val Val Met Thr Gln Ser
    130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Asn Ser Leu Gln Pro Glu Asp Phe Ala Thr Tyr Tyr
    210                 215                 220

Cys Gln His Leu Asn Ser Tyr Pro Leu Thr Phe Gly Gly Gly Thr Lys
225                 230                 235                 240

Val Asp Ile Lys Arg Ala Ala Ala Leu Glu
                245                 250

<210> SEQ ID NO 7
<211> LENGTH: 756
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(756)
<220> FEATURE:
<221> NAME/KEY: misc_feature
<222> LOCATION: (85)..(87)
<223> OTHER INFORMATION: A codon encoding an amino acid other than
      cysteine

<400> SEQUENCE: 7 atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt nnn atc atc tct      96
Gly Glu Ser Leu Arg Ile Ser Cys Lys Gly Ser Gly Xaa Ile Ile Ser
            20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
    50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
65                  70                  75                  80
```

```
gct tac ctg caa tgg aac agc ctg aaa gcg agc gac acc gcg atg tac       288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg       336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggc ggc agc ggt           384
Gly Gln Gly Thr Leu Val Thr Val Ser Ser Gly Gly Gly Ser Gly
        115                 120                 125 ggt ggc ggc agc ggc ggc ggc agc gat gtt gtg atg acc cag agc           432
Gly Gly Gly Ser Gly Gly Gly Ser Asp Val Val Met Thr Gln Ser
    130                 135                 140 ccg agc ttc ctg agc gcg ttc gtt ggt gac cgt atc acc att acc tgc       480
Pro Ser Phe Leu Ser Ala Phe Val Gly Asp Arg Ile Thr Ile Thr Cys
145                 150                 155                 160 cgc gcc agc agc ggc atc agc cgc tat ctg gcg tgg tat cag caa gca       528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa       576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc       624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac       672
Thr Leu Thr Ile Asn Ser Leu Gln Pro Glu Asp Phe Ala Thr Tyr Tyr
    210                 215                 220 tgc caa cac ctg aat agc tat ccg ctg acc ttc ggt ggc ggc acc aaa       720
Cys Gln His Leu Asn Ser Tyr Pro Leu Thr Phe Gly Gly Gly Thr Lys
225                 230                 235                 240 gtg gac atc aaa cgc gcg gcc gca ctg gaa taa taa                        756
Val Asp Ile Lys Arg Ala Ala Ala Leu Glu
                245                 250

<210> SEQ ID NO 8
<211> LENGTH: 250
<212> TYPE: PRT
<213> ORGANISM: Artificial
<220> FEATURE:
<221> NAME/KEY: misc_feature
<222> LOCATION: (29)..(29)
<223> OTHER INFORMATION: The 'Xaa' at location 29 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 8

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Xaa Ile Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95
```

```
Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Ser Gly
        115                 120                 125

Gly Gly Gly Ser Gly Gly Gly Ser Asp Val Val Met Thr Gln Ser
    130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
                180                 185                 190

Thr Gly Val Pro Ser Arg Phe Ser Gly Ser Gly Ser Gly Thr Glu Phe
                195                 200                 205

Thr Leu Thr Ile Asn Ser Leu Gln Pro Glu Asp Phe Ala Thr Tyr Tyr
            210                 215                 220

Cys Gln His Leu Asn Ser Tyr Pro Leu Thr Phe Gly Gly Gly Thr Lys
225                 230                 235                 240

Val Asp Ile Lys Arg Ala Ala Ala Leu Glu
                245                 250

<210> SEQ ID NO 9
<211> LENGTH: 774
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(774)
<220> FEATURE:
<221> NAME/KEY: misc_feature
<222> LOCATION: (85)..(87)
<223> OTHER INFORMATION: A codon encoding an amino acid other than
      cysteine

<400> SEQUENCE: 9 atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt nnn atc atc tct     96
Gly Glu Ser Leu Arg Ile Ser Cys Lys Gly Ser Gly Xaa Ile Ile Ser
            20                  25                  30 tct tac tgg atc agc tgg gtt cgt cag atg ccg ggc aag ggc ctg gaa    144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg    192
Trp Met Gly Lys Ile Asp Pro Gly Asp Ser Tyr Ile Asn Tyr Ser Pro
    50                  55                  60 agc ttt cag ggc cat gtt acc atc agc gcc gat aaa agc att aac acc    240
Ser Phe Gln Gly His Val Thr Ile Ser Ala Asp Lys Ser Ile Asn Thr
65                  70                  75                  80 gct tac ctg caa tgg aac agc ctg aaa gcg agc gac acc gcg atg tac    288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg    336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt    384
Gly Gln Gly Thr Leu Val Thr Val Ser Ser Gly Gly Gly Gly Ser Gly
        115                 120                 125
```

| | | |
|---|---|---|
| ggt ggc ggc agc ggc ggc ggc agc gat gtt gtg atg acc cag agc<br>Gly Gly Gly Ser Gly Gly Gly Ser Asp Val Val Met Thr Gln Ser<br>130 135 140 | | 432 |
| ccg agc ttc ctg agc gcg ttc gtt ggt gac cgt atc acc att acc tgc<br>Pro Ser Phe Leu Ser Ala Phe Val Gly Asp Arg Ile Thr Ile Thr Cys<br>145 150 155 160 | | 480 |
| cgc gcc agc agc ggc atc agc cgc tat ctg gcg tgg tat cag caa gca<br>Arg Ala Ser Ser Gly Ile Ser Arg Tyr Leu Ala Trp Tyr Gln Gln Ala<br>165 170 175 | | 528 |
| ccg ggt aaa gca ccg aaa ctg ctg atc tat gct gca agc acc ctg caa<br>Pro Gly Lys Ala Pro Lys Leu Leu Ile Tyr Ala Ala Ser Thr Leu Gln<br>180 185 190 | | 576 |
| acc ggc gtt ccg agc cgt ttt agc ggt agc ggc agc ggc acc gag ttc<br>Thr Gly Val Pro Ser Arg Phe Ser Gly Ser Gly Ser Gly Thr Glu Phe<br>195 200 205 | | 624 |
| acc ctg acc atc aac agc ctg caa ccg gag gat ttt gcc acc tat tac<br>Thr Leu Thr Ile Asn Ser Leu Gln Pro Glu Asp Phe Ala Thr Tyr Tyr<br>210 215 220 | | 672 |
| tgc caa cac ctg aat agc tat ccg ctg acc ttc ggt ggc ggc acc aaa<br>Cys Gln His Leu Asn Ser Tyr Pro Leu Thr Phe Gly Gly Gly Thr Lys<br>225 230 235 240 | | 720 |
| gtg gac atc aaa cgc gcg gcc gca ctc gag cac cac cac cac cac cac<br>Val Asp Ile Lys Arg Ala Ala Ala Leu Glu His His His His His His<br>245 250 255 | | 768 |
| taa taa | | 774 |

```
<210> SEQ ID NO 10
<211> LENGTH: 256
<212> TYPE: PRT
<213> ORGANISM: Artificial
<220> FEATURE:
<221> NAME/KEY: misc_feature
<222> LOCATION: (29)..(29)
<223> OTHER INFORMATION: The 'Xaa' at location 29 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 10
```

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Xaa Ile Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Asp Val Val Met Thr Gln Ser
    130                 135                 140

Pro Ser Phe Leu Ser Ala Phe Val Gly Asp Arg Ile Thr Ile Thr Cys

```
                145                 150                 155                 160
Arg Ala Ser Ser Gly Ile Ser Arg Tyr Leu Ala Trp Tyr Gln Gln Ala
                165                 170                 175
Pro Gly Lys Ala Pro Lys Leu Leu Ile Tyr Ala Ala Ser Thr Leu Gln
                180                 185                 190
Thr Gly Val Pro Ser Arg Phe Ser Gly Ser Gly Ser Gly Thr Glu Phe
                195                 200                 205
Thr Leu Thr Ile Asn Ser Leu Gln Pro Glu Asp Phe Ala Thr Tyr Tyr
                210                 215                 220
Cys Gln His Leu Asn Ser Tyr Pro Leu Thr Phe Gly Gly Gly Thr Lys
225                 230                 235                 240
Val Asp Ile Lys Arg Ala Ala Ala Leu Glu His His His His His His
                245                 250                 255

<210> SEQ ID NO 11
<211> LENGTH: 744
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(744)

<400> SEQUENCE: 11 atg gct gaa gtt caa ctt gtt gaa tct ggt gct gaa gtt aaa aaa ccg    48
Met Ala Glu Val Gln Leu Val Glu Ser Gly Ala Glu Val Lys Lys Pro
1               5                   10                  15 ggt gaa tct ctg cgt atc tct tgc aaa ggt tct ggt tgc atc atc tct    96
Gly Glu Ser Leu Arg Ile Ser Cys Lys Gly Ser Gly Cys Ile Ile Ser
                20                  25                  30 tct tac tgg atc agc tgg gtt cgt cag atg ccg ggc aag ggc ctg gaa   144
Ser Tyr Trp Ile Ser Trp Val Arg Gln Met Pro Gly Lys Gly Leu Glu
            35                  40                  45 tgg atg ggt aaa att gat ccg ggc gac agc tat att aac tac agc ccg   192
Trp Met Gly Lys Ile Asp Pro Gly Asp Ser Tyr Ile Asn Tyr Ser Pro
        50                  55                  60 agc ttt cag ggc cat gtt acc atc agc gcc gat aaa agc att aac acc   240
Ser Phe Gln Gly His Val Thr Ile Ser Ala Asp Lys Ser Ile Asn Thr
65                  70                  75                  80 gct tac ctg caa tgg aac agc ctg aaa gcg agc gac acc gcg atg tac   288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg   336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt   384
Gly Gln Gly Thr Leu Val Thr Val Ser Ser Gly Gly Gly Gly Ser Gly
        115                 120                 125 ggt ggc ggc agc ggc ggc ggc agc gat gtt gtg atg acc cag agc       432
Gly Gly Gly Ser Gly Gly Gly Gly Ser Asp Val Val Met Thr Gln Ser
130                 135                 140 ccg agc ttc ctg agc gcg ttc gtt ggt gac cgt atc acc att acc tgc   480
Pro Ser Phe Leu Ser Ala Phe Val Gly Asp Arg Ile Thr Ile Thr Cys
145                 150                 155                 160 cgc gcc agc agc ggc atc agc cgc tat ctg gcg tgg tat cag caa gca   528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa   576
Pro Gly Lys Ala Pro Lys Leu Leu Ile Tyr Ala Ala Ser Thr Leu Gln
```

```
                      180                 185                 190
acc ggc gtt ccg agc cgt ttt agc ggt agc ggc agc ggc acc gag ttc        624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac        672
Thr Leu Thr Ile Asn Ser Leu Gln Pro Glu Asp Phe Ala Thr Tyr Tyr
    210                 215                 220 tgc caa cac ctg aat agc tat ccg ctg acc ttc ggt ggc ggc acc aaa        720
Cys Gln His Leu Asn Ser Tyr Pro Leu Thr Phe Gly Gly Gly Thr Lys
225                 230                 235                 240 gtg gac atc aaa cgc gcg taa taa                                        744
Val Asp Ile Lys Arg Ala
                245
```

<210> SEQ ID NO 12
<211> LENGTH: 246
<212> TYPE: PRT
<213> ORGANISM: Artificial
<220> FEATURE:
<223> OTHER INFORMATION: Synthetic Construct

<400> SEQUENCE: 12

```
Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Cys Ile Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Val Val Met Thr Gln Ser
    130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Asn Ser Leu Gln Pro Glu Asp Phe Ala Thr Tyr Tyr
    210                 215                 220

Cys Gln His Leu Asn Ser Tyr Pro Leu Thr Phe Gly Gly Gly Thr Lys
225                 230                 235                 240

Val Asp Ile Lys Arg Ala
                245
```

<210> SEQ ID NO 13
<211> LENGTH: 744

<210> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(744)
<220> FEATURE:
<221> NAME/KEY: misc_feature
<222> LOCATION: (85)..(87)
<223> OTHER INFORMATION: A codon encoding an amino acid other than cysteine

<400> SEQUENCE: 13

```
atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
 1               5                  10                  15 ggt gaa tct ctg cgt atc tct tgc aaa ggt tct ggt nnn atc atc tct      96
Gly Glu Ser Leu Arg Ile Ser Cys Lys Gly Ser Gly Xaa Ile Ile Ser
             20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
         35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
     50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
 65                  70                  75                  80 gct tac ctg caa tgg aac agc ctg aaa gcg agc gac acc gcg atg tac     288
Ala Tyr Leu Gln Trp Asn Ser Leu Lys Ala Ser Asp Thr Ala Met Tyr
                 85                  90                  95 tac tgt gcc cgt ggc ggt cgt gac ttc ggt gat agc ttc gat tac tgg     336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt     384
Gly Gln Gly Thr Leu Val Thr Val Ser Ser Gly Gly Gly Gly Ser Gly
        115                 120                 125 ggt ggc ggc agc ggc ggc ggc agc gat gtt gtg atg acc cag agc         432
Gly Gly Gly Ser Gly Gly Gly Gly Ser Asp Val Val Met Thr Gln Ser
    130                 135                 140 ccg agc ttc ctg agc gcg ttc gtt ggt gac cgt atc acc att acc tgc     480
Pro Ser Phe Leu Ser Ala Phe Val Gly Asp Arg Ile Thr Ile Thr Cys
145                 150                 155                 160 cgc gcc agc agc ggc atc agc cgc tat ctg gcg tgg tat cag caa gca     528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa     576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc     624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac     672
Thr Leu Thr Ile Asn Ser Leu Gln Pro Glu Asp Phe Ala Thr Tyr Tyr
    210                 215                 220 tgc caa cac ctg aat agc tat ccg ctg acc ttc ggt ggc ggc acc aaa     720
Cys Gln His Leu Asn Ser Tyr Pro Leu Thr Phe Gly Gly Gly Thr Lys
225                 230                 235                 240 gtg gac atc aaa cgc gcg taa taa                                     744
Val Asp Ile Lys Arg Ala
                245
```

<210> SEQ ID NO 14
<211> LENGTH: 246
<212> TYPE: PRT
<213> ORGANISM: Artificial
<220> FEATURE:
<221> NAME/KEY: misc_feature
<222> LOCATION: (29)..(29)
<223> OTHER INFORMATION: The 'Xaa' at location 29 stands for Lys, Asn, Arg, Ser, Thr, Ile, Met, Glu, Asp, Gly, Ala, Val, Gln, His, Pro, Leu, Tyr, Trp, Cys, or Phe.
<220> FEATURE:
<223> OTHER INFORMATION: Synthetic Construct

<400> SEQUENCE: 14

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Xaa Ile Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Val Val Met Thr Gln Ser
    130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Asn Ser Leu Gln Pro Glu Asp Phe Ala Thr Tyr Tyr
    210                 215                 220

Cys Gln His Leu Asn Ser Tyr Pro Leu Thr Phe Gly Gly Gly Thr Lys
225                 230                 235                 240

Val Asp Ile Lys Arg Ala
                245

<210> SEQ ID NO 15
<211> LENGTH: 744
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(744)

<400> SEQUENCE: 15 atg gcg gaa gtg cag ctg gtt gaa tct ggt gct gaa gtt aaa aaa ccg      48
Met Ala Glu Val Gln Leu Val Glu Ser Gly Ala Glu Val Lys Lys Pro

```
                 1               5                   10                  15
ggt gaa tct ctg cgt atc tct tgc aaa ggt tct ggt tgc atc atc tct        96
Gly Glu Ser Leu Arg Ile Ser Cys Lys Gly Ser Gly Cys Ile Ile Ser
             20                  25                  30 tct tac tgg atc agc tgg gtt cgt cag atg ccg ggc aag ggc ctg gaa        144
Ser Tyr Trp Ile Ser Trp Val Arg Gln Met Pro Gly Lys Gly Leu Glu
         35                  40                  45 tgg atg ggt aaa att gat ccg ggc gac agc tat att aac tac agc ccg        192
Trp Met Gly Lys Ile Asp Pro Gly Asp Ser Tyr Ile Asn Tyr Ser Pro
     50                  55                  60 agc ttt cag ggc cat gtt acc atc agc gcc gat aaa agc att aac acc        240
Ser Phe Gln Gly His Val Thr Ile Ser Ala Asp Lys Ser Ile Asn Thr
 65                  70                  75                  80 gct tac ctg caa tgg aac agc ctg aaa gcg agc gac acc gcg atg tac        288
Ala Tyr Leu Gln Trp Asn Ser Leu Lys Ala Ser Asp Thr Ala Met Tyr
                 85                  90                  95 tac tgt gcc cgt ggc ggt cgt gac ttc ggt gat agc ttc gat tac tgg        336
Tyr Cys Ala Arg Gly Gly Arg Asp Phe Gly Asp Ser Phe Asp Tyr Trp
             100                 105                 110 ggt cag ggc acc ctg gtg acc gtg agc agc ggt ggt ggc ggc agc ggt        384
Gly Gln Gly Thr Leu Val Thr Val Ser Ser Gly Gly Gly Gly Ser Gly
         115                 120                 125 ggt ggc ggc agc ggc ggc ggc agc gat gtt gtg atg acc cag agc            432
Gly Gly Gly Ser Gly Gly Gly Ser Asp Val Val Met Thr Gln Ser
     130                 135                 140 ccg agc ttc ctg agc gcg ttc gtt ggt gac cgt atc acc att acc tgc        480
Pro Ser Phe Leu Ser Ala Phe Val Gly Asp Arg Ile Thr Ile Thr Cys
145                 150                 155                 160 cgc gcc agc agc ggc atc agc cgc tat ctg gcg tgg tat cag caa gca        528
Arg Ala Ser Ser Gly Ile Ser Arg Tyr Leu Ala Trp Tyr Gln Gln Ala
                 165                 170                 175 ccg ggt aaa gca ccg aaa ctg ctg atc tat gct gca agc acc ctg caa        576
Pro Gly Lys Ala Pro Lys Leu Leu Ile Tyr Ala Ala Ser Thr Leu Gln
             180                 185                 190 acc ggc gtt ccg agc cgt ttt agc ggt agc ggc agc ggc acc gag ttc        624
Thr Gly Val Pro Ser Arg Phe Ser Gly Ser Gly Ser Gly Thr Glu Phe
         195                 200                 205 acc ctg acc atc aac agc ctg caa ccg gag gat ttt gcc acc tat tac        672
Thr Leu Thr Ile Asn Ser Leu Gln Pro Glu Asp Phe Ala Thr Tyr Tyr
     210                 215                 220 tgc caa cac ctg aat agc tat ccg ctg acc ttc ggt ggc ggc acc aaa        720
Cys Gln His Leu Asn Ser Tyr Pro Leu Thr Phe Gly Gly Gly Thr Lys
225                 230                 235                 240 gtg gac atc aaa cgc gcg taa taa                                        744
Val Asp Ile Lys Arg Ala
                 245

<210> SEQ ID NO 16
<211> LENGTH: 246
<212> TYPE: PRT
<213> ORGANISM: Artificial
<220> FEATURE:
<223> OTHER INFORMATION: Synthetic Construct

<400> SEQUENCE: 16

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Cys Ile Ile Ser
            20                  25                  30

Ser Tyr Trp Ile Ser Trp Val Arg Gln Met Pro Gly Lys Gly Leu Glu
```

```
                 35                  40                  45
Trp Met Gly Lys Ile Asp Pro Gly Asp Ser Tyr Ile Asn Tyr Ser Pro
     50                  55                  60

Ser Phe Gln Gly His Val Thr Ile Ser Ala Asp Lys Ser Ile Asn Thr
 65                  70                  75                  80

Ala Tyr Leu Gln Trp Asn Ser Leu Lys Ala Ser Asp Thr Ala Met Tyr
                 85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Gly Gly Gly Gly Ser Gly
        115                 120                 125

Gly Gly Gly Ser Gly Gly Gly Ser Asp Val Val Met Thr Gln Ser
    130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Asn Ser Leu Gln Pro Glu Asp Phe Ala Thr Tyr Tyr
    210                 215                 220

Cys Gln His Leu Asn Ser Tyr Pro Leu Thr Phe Gly Gly Gly Thr Lys
225                 230                 235                 240

Val Asp Ile Lys Arg Ala
                245

<210> SEQ ID NO 17
<211> LENGTH: 744
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(744)
<220> FEATURE:
<221> NAME/KEY: misc_feature
<222> LOCATION: (85)..(87)
<223> OTHER INFORMATION: A codon encoding an amino acid other than
      cysteine

<400> SEQUENCE: 17 atg gcg gaa gtg cag ctg gtt gaa tct ggt gct gaa gtt aaa aaa ccg      48
Met Ala Glu Val Gln Leu Val Glu Ser Gly Ala Glu Val Lys Lys Pro
 1               5                  10                  15 ggt gaa tct ctg cgt atc tct tgc aaa ggt tct ggt nnn atc atc tct      96
Gly Glu Ser Leu Arg Ile Ser Cys Lys Gly Ser Gly Xaa Ile Ile Ser
             20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
         35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
     50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
 65                  70                  75                  80
```

```
gct tac ctg caa tgg aac agc ctg aaa gcg agc gac acc gcg atg tac      288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg      336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt      384
Gly Gln Gly Thr Leu Val Thr Val Ser Ser Gly Gly Gly Gly Ser Gly
        115                 120                 125 ggt ggc ggc agc ggc ggc ggc agc gat gtt gtg atg acc cag agc          432
Gly Gly Gly Ser Gly Gly Gly Ser Asp Val Val Met Thr Gln Ser
    130                 135                 140 ccg agc ttc ctg agc gcg ttc gtt ggt gac cgt atc acc att acc tgc      480
Pro Ser Phe Leu Ser Ala Phe Val Gly Asp Arg Ile Thr Ile Thr Cys
145                 150                 155                 160 cgc gcc agc agc ggc atc agc cgc tat ctg gcg tgg tat cag caa gca      528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa      576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc      624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac      672
Thr Leu Thr Ile Asn Ser Leu Gln Pro Glu Asp Phe Ala Thr Tyr Tyr
    210                 215                 220 tgc caa cac ctg aat agc tat ccg ctg acc ttc ggt ggc ggc acc aaa      720
Cys Gln His Leu Asn Ser Tyr Pro Leu Thr Phe Gly Gly Gly Thr Lys
225                 230                 235                 240 gtg gac atc aaa cgc gcg taa taa                                       744
Val Asp Ile Lys Arg Ala
                245
```

```
<210> SEQ ID NO 18
<211> LENGTH: 246
<212> TYPE: PRT
<213> ORGANISM: Artificial
<220> FEATURE:
<221> NAME/KEY: misc_feature
<222> LOCATION: (29)..(29)
<223> OTHER INFORMATION: The 'Xaa' at location 29 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 18

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Xaa Ile Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
```

```
              100                 105                 110
Gly Gln Gly Thr Leu Val Thr Val Ser Ser Gly Gly Gly Ser Gly
            115                 120                 125

Gly Gly Gly Ser Gly Gly Gly Gly Ser Asp Val Val Met Thr Gln Ser
        130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Asn Ser Leu Gln Pro Glu Asp Phe Ala Thr Tyr Tyr
    210                 215                 220

Cys Gln His Leu Asn Ser Tyr Pro Leu Thr Phe Gly Gly Gly Thr Lys
225                 230                 235                 240

Val Asp Ile Lys Arg Ala
                245

<210> SEQ ID NO 19
<211> LENGTH: 774
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(774)

<400> SEQUENCE: 19 atg gcg gaa gtg cag ctg gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt tgc atc atc tct      96
Gly Glu Ser Leu Arg Ile Ser Cys Lys Gly Ser Gly Cys Ile Ile Ser
                20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
            35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
        50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
65                  70                  75                  80 gct tac ctg caa tgg aac agc ctg aaa gcg agc gac acc gcg atg tac     288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg     336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt     384
Gly Gln Gly Thr Leu Val Thr Val Ser Ser Gly Gly Gly Gly Ser Gly
        115                 120                 125 ggt ggc ggc agc ggc ggc ggc agc gat gtt gtg atg acc cag agc         432
Gly Gly Gly Ser Gly Gly Gly Gly Ser Asp Val Val Met Thr Gln Ser
    130                 135                 140 ccg agc ttc ctg agc gcg ttc gtt ggt gac cgt atc acc att acc tgc     480
```

```
cgc gcc agc agc ggc atc agc cgc tat ctg gcg tgg tat cag caa gca      528
Arg Ala Ser Ser Gly Ile Ser Arg Tyr Leu Ala Trp Tyr Gln Gln Ala
            165                 170                 175 ccg ggt aaa gca ccg aaa ctg ctg atc tat gct gca agc acc ctg caa      576
Pro Gly Lys Ala Pro Lys Leu Leu Ile Tyr Ala Ala Ser Thr Leu Gln
        180                 185                 190 acc ggc gtt ccg agc cgt ttt agc ggt agc ggc agc ggc acc gag ttc      624
Thr Gly Val Pro Ser Arg Phe Ser Gly Ser Gly Ser Gly Thr Glu Phe
    195                 200                 205 acc ctg acc atc aac agc ctg caa ccg gag gat ttt gcc acc tat tac      672
Thr Leu Thr Ile Asn Ser Leu Gln Pro Glu Asp Phe Ala Thr Tyr Tyr
210                 215                 220 tgc caa cac ctg aat agc tat ccg ctg acc ttc ggt ggc ggc acc aaa      720
Cys Gln His Leu Asn Ser Tyr Pro Leu Thr Phe Gly Gly Gly Thr Lys
225                 230                 235                 240 gtg gac atc aaa cgc gcg gcc gca ctc gag cac cac cac cac cac cac      768
Val Asp Ile Lys Arg Ala Ala Ala Leu Glu His His His His His His
                245                 250                 255 taa taa                                                               774

<210> SEQ ID NO 20
<211> LENGTH: 256
<212> TYPE: PRT
<213> ORGANISM: Artificial
<220> FEATURE:
<223> OTHER INFORMATION: Synthetic Construct

<400> SEQUENCE: 20

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Cys Ile Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Asp Val Val Met Thr Gln Ser
    130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Asn Ser Leu Gln Pro Glu Asp Phe Ala Thr Tyr Tyr
```

210                 215                 220
Cys Gln His Leu Asn Ser Tyr Pro Leu Thr Phe Gly Gly Gly Thr Lys
225                 230                 235                 240

Val Asp Ile Lys Arg Ala Ala Ala Leu Glu His His His His His
                245                 250                 255

<210> SEQ ID NO 21
<211> LENGTH: 774
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(774)
<220> FEATURE:
<221> NAME/KEY: misc_feature
<222> LOCATION: (85)..(87)
<223> OTHER INFORMATION: A codon encoding an amino acid other than
      cysteine

<400> SEQUENCE: 21 atg gcg gaa gtg cag ctg gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt nnn atc atc tct      96
Gly Glu Ser Leu Arg Ile Ser Cys Lys Gly Ser Gly Xaa Ile Ile Ser
            20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
    50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
65                  70                  75                  80 gct tac ctg caa tgg aac agc ctg aaa gcg agc gac acc gcg atg tac     288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg     336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt     384
Gly Gln Gly Thr Leu Val Thr Val Ser Ser Gly Gly Gly Gly Ser Gly
        115                 120                 125 ggt ggc ggc agc ggc ggc ggc agc gat gtt gtg atg acc cag agc         432
Gly Gly Gly Ser Gly Gly Gly Gly Ser Asp Val Val Met Thr Gln Ser
    130                 135                 140 ccg agc ttc ctg agc gcg ttc gtt ggt gac cgt atc acc att acc tgc     480
Pro Ser Phe Leu Ser Ala Phe Val Gly Asp Arg Ile Thr Ile Thr Cys
145                 150                 155                 160 cgc gcc agc agc ggc atc agc cgc tat ctg gcg tgg tat cag caa gca     528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa     576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc     624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac     672
Thr Leu Thr Ile Asn Ser Leu Gln Pro Glu Asp Phe Ala Thr Tyr Tyr

```
Thr Leu Thr Ile Asn Ser Leu Gln Pro Glu Asp Phe Ala Thr Tyr Tyr
    210                 215                 220 tgc caa cac ctg aat agc tat ccg ctg acc ttc ggt ggc ggc acc aaa      720
Cys Gln His Leu Asn Ser Tyr Pro Leu Thr Phe Gly Gly Gly Thr Lys
225                 230                 235                 240 gtg gac atc aaa cgc gcg gcc gca ctc gag cac cac cac cac cac cac      768
Val Asp Ile Lys Arg Ala Ala Ala Leu Glu His His His His His His
                245                 250                 255 taa taa                                                               774

<210> SEQ ID NO 22
<211> LENGTH: 256
<212> TYPE: PRT
<213> ORGANISM: Artificial
<220> FEATURE:
<221> NAME/KEY: misc_feature
<222> LOCATION: (29)..(29)
<223> OTHER INFORMATION: The 'Xaa' at location 29 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 22

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Xaa Ile Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Val Val Met Thr Gln Ser
    130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Asn Ser Leu Gln Pro Glu Asp Phe Ala Thr Tyr Tyr
    210                 215                 220

Cys Gln His Leu Asn Ser Tyr Pro Leu Thr Phe Gly Gly Gly Thr Lys
225                 230                 235                 240

Val Asp Ile Lys Arg Ala Ala Ala Leu Glu His His His His His His
                245                 250                 255

<210> SEQ ID NO 23
```

<211> LENGTH: 744
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(744)

<400> SEQUENCE: 23

```
atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt tat agc atc tct      96
Gly Glu Ser Leu Arg Ile Ser Cys Lys Gly Ser Gly Tyr Ser Ile Ser
            20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
    50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
65                  70                  75                  80 gct tac ctg caa tgg aac agc ctg aaa gcg agc gac acc gcg atg tac     288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg     336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt     384
Gly Gln Gly Thr Leu Val Thr Val Ser Ser Gly Gly Gly Gly Ser Gly
        115                 120                 125 ggc ggc ggc agc ggc ggc ggc ggc agc gat gtt gtg atg acc cag agc     432
Gly Gly Gly Ser Gly Gly Gly Gly Ser Asp Val Val Met Thr Gln Ser
    130                 135                 140 ccg agc tcc ctg agc gcg agc gtt ggt gac cgt atc acc att acc tgc     480
Pro Ser Ser Leu Ser Ala Ser Val Gly Asp Arg Ile Thr Ile Thr Cys
145                 150                 155                 160 cgc gcc agc agc ggc atc agc cgc tat ctg gcg tgg tat cag caa gca     528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa     576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc     624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac     672
Thr Leu Thr Ile Asn Ser Leu Gln Pro Glu Asp Phe Ala Thr Tyr Tyr
    210                 215                 220 tgc caa cac ctg aat agc tat ccg ctg acc ttc ggt ggc ggc acc aaa     720
Cys Gln His Leu Asn Ser Tyr Pro Leu Thr Phe Gly Gly Gly Thr Lys
225                 230                 235                 240 gtg gac atc aaa cgc gcg taa taa                                     744
Val Asp Ile Lys Arg Ala
                245
```

<210> SEQ ID NO 24
<211> LENGTH: 246
<212> TYPE: PRT

<213> ORGANISM: Artificial
<220> FEATURE:
<223> OTHER INFORMATION: Synthetic Construct

<400> SEQUENCE: 24

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Tyr Ser Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Ser Gly Gly Gly Ser Asp Val Val Met Thr Gln Ser
    130                 135                 140

Pro Ser Ser Leu Ser Ala Ser Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Asn Ser Leu Gln Pro Glu Asp Phe Ala Thr Tyr Tyr
    210                 215                 220

Cys Gln His Leu Asn Ser Tyr Pro Leu Thr Phe Gly Gly Gly Thr Lys
225                 230                 235                 240

Val Asp Ile Lys Arg Ala
                245

<210> SEQ ID NO 25
<211> LENGTH: 744
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(744)

<400> SEQUENCE: 25 atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt tat agc atc tct      96
Gly Glu Ser Leu Arg Ile Ser Cys Lys Gly Ser Gly Tyr Ser Ile Ser
            20                  25                  30 tct tac tgg atc agc tgg gtt cgt cag atg ccg ggc aag ggc ctg gaa    144
Ser Tyr Trp Ile Ser Trp Val Arg Gln Met Pro Gly Lys Gly Leu Glu
        35                  40                  45

```
tgg atg ggt aaa att gat ccg ggc gac agc tat att aac tac agc ccg      192
Trp Met Gly Lys Ile Asp Pro Gly Asp Ser Tyr Ile Asn Tyr Ser Pro
    50                  55                  60 agc ttt cag ggc cat gtt acc atc agc gcc gat aaa agc att aac acc      240
Ser Phe Gln Gly His Val Thr Ile Ser Ala Asp Lys Ser Ile Asn Thr
65                  70                  75                  80 gct tac ctg caa tgg aac agc ctg aaa gcg agc gac acc gcg atg tac      288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg      336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt      384
Gly Gln Gly Thr Leu Val Thr Val Ser Ser Gly Gly Gly Gly Ser Gly
        115                 120                 125 ggt ggc ggc agc ggc ggc ggc agc gat att cag atg acc cag agc          432
Gly Gly Gly Ser Gly Gly Gly Ser Asp Ile Gln Met Thr Gln Ser
    130                 135                 140 ccg agc tcc ctg agc gcg agc gtt ggt gac cgt atc acc att acc tgc      480
Pro Ser Ser Leu Ser Ala Ser Val Gly Asp Arg Ile Thr Ile Thr Cys
145                 150                 155                 160 cgc gcc agc agc ggc atc agc cgc tat ctg gcg tgg tat cag caa gca      528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa      576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc      624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac      672
Thr Leu Thr Ile Asn Ser Leu Gln Pro Glu Asp Phe Ala Thr Tyr Tyr
    210                 215                 220 tgc caa cac ctg aat agc tat ccg ctg acc ttc ggt ggc ggc acc aaa      720
Cys Gln His Leu Asn Ser Tyr Pro Leu Thr Phe Gly Gly Gly Thr Lys
225                 230                 235                 240 gtg gac atc aaa cgc gcg taa taa                                      744
Val Asp Ile Lys Arg Ala
                245

<210> SEQ ID NO 26
<211> LENGTH: 246
<212> TYPE: PRT
<213> ORGANISM: Artificial
<220> FEATURE:
<223> OTHER INFORMATION: Synthetic Construct

<400> SEQUENCE: 26

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Tyr Ser Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95
```

```
Tyr Cys Ala Arg Gly Gly Arg Asp Phe Gly Asp Ser Phe Asp Tyr Trp
            100                 105                 110
Gly Gln Gly Thr Leu Val Thr Val Ser Ser Gly Gly Gly Gly Ser Gly
        115                 120                 125
Gly Gly Gly Ser Gly Gly Gly Gly Ser Asp Ile Gln Met Thr Gln Ser
    130                 135                 140
Pro Ser Ser Leu Ser Ala Ser Val Gly Asp Arg Ile Thr Ile Thr Cys
145                 150                 155                 160
Arg Ala Ser Ser Gly Ile Ser Arg Tyr Leu Ala Trp Tyr Gln Gln Ala
                165                 170                 175
Pro Gly Lys Ala Pro Lys Leu Leu Ile Tyr Ala Ala Ser Thr Leu Gln
            180                 185                 190
Thr Gly Val Pro Ser Arg Phe Ser Gly Ser Gly Ser Gly Thr Glu Phe
        195                 200                 205
Thr Leu Thr Ile Asn Ser Leu Gln Pro Glu Asp Phe Ala Thr Tyr Tyr
    210                 215                 220
Cys Gln His Leu Asn Ser Tyr Pro Leu Thr Phe Gly Gly Gly Thr Lys
225                 230                 235                 240
Val Asp Ile Lys Arg Ala
                245
```

<210> SEQ ID NO 27
<211> LENGTH: 744
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(744)

<400> SEQUENCE: 27

```
atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt tgc atc atc tct      96
Gly Glu Ser Leu Arg Ile Ser Cys Lys Gly Ser Gly Cys Ile Ile Ser
                20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
            35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
        50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
65                  70                  75                  80 gct tac ctg caa tgg agc agc ctg aaa gcg agc gac acc gcg atg tac     288
Ala Tyr Leu Gln Trp Ser Ser Leu Lys Ala Ser Asp Thr Ala Met Tyr
                85                  90                  95 tac tgt gcc cgt ggc ggt cgt gac ttc ggt gat agc ttc gat tac tgg     336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt     384
Gly Gln Gly Thr Leu Val Thr Val Ser Ser Gly Gly Gly Gly Ser Gly
        115                 120                 125 ggt ggc ggc agc ggc ggc ggc agc gat att cag atg acc cag agc         432
Gly Gly Gly Ser Gly Gly Gly Gly Ser Asp Ile Gln Met Thr Gln Ser
    130                 135                 140
```

| | | | | | | | | | | | | | | | |
|---|---|---|---|---|---|---|---|---|---|---|---|---|---|---|---|
| ccg | agc | ttc | ctg | agc | gcg | ttc | gtt | ggt | gac | cgt | atc | acc | att | acc | tgc | 480 |
| Pro | Ser | Phe | Leu | Ser | Ala | Phe | Val | Gly | Asp | Arg | Ile | Thr | Ile | Thr | Cys |
| 145 | | | | 150 | | | | | 155 | | | | 160 |

```
ccg agc ttc ctg agc gcg ttc gtt ggt gac cgt atc acc att acc tgc      480
Pro Ser Phe Leu Ser Ala Phe Val Gly Asp Arg Ile Thr Ile Thr Cys
145             150                 155                 160 cgc gcc agc agc ggc atc agc cgc tat ctg gcg tgg tat cag caa aaa      528
Arg Ala Ser Ser Gly Ile Ser Arg Tyr Leu Ala Trp Tyr Gln Gln Lys
                165                 170                 175 ccg ggt aaa gca ccg aaa ctg ctg atc tat gct gca agc acc ctg caa      576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc      624
Thr Gly Val Pro Ser Arg Phe Ser Gly Ser Gly Ser Gly Thr Glu Phe
                195                 200                 205 acc ctg acc atc agc agc ctg caa ccg gag gat ttt gcc acc tat tac      672
Thr Leu Thr Ile Ser Ser Leu Gln Pro Glu Asp Phe Ala Thr Tyr Tyr
210                 215                 220 tgc caa cac ctg aat agc tat ccg ctg acc ttc ggt ggc ggc acc aaa      720
Cys Gln His Leu Asn Ser Tyr Pro Leu Thr Phe Gly Gly Gly Thr Lys
225                 230                 235                 240 gtg gac atc aaa cgc gcg taa taa                                      744
Val Asp Ile Lys Arg Ala
                245
```

<210> SEQ ID NO 28
<211> LENGTH: 246
<212> TYPE: PRT
<213> ORGANISM: Artificial
<220> FEATURE:
<223> OTHER INFORMATION: Synthetic Construct

<400> SEQUENCE: 28

```
Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Cys Ile Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Ser Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Asp Ile Gln Met Thr Gln Ser
    130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Lys
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Ser Ser Leu Gln Pro Glu Asp Phe Ala Thr Tyr Tyr
```

```
                210                 215                 220
Cys Gln His Leu Asn Ser Tyr Pro Leu Thr Phe Gly Gly Gly Thr Lys
225                 230                 235                 240

Val Asp Ile Lys Arg Ala
                245

<210> SEQ ID NO 29
<211> LENGTH: 759
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(759)

<400> SEQUENCE: 29 atg gct gaa gtt caa ctt gtt gaa tct ggt gct gaa gtt aaa aaa ccg         48
Met Ala Glu Val Gln Leu Val Glu Ser Gly Ala Glu Val Lys Lys Pro
1               5                   10                  15 ggt gaa tct ctg cgt atc tct tgc aaa ggt tct ggt tgc atc atc tct         96
Gly Glu Ser Leu Arg Ile Ser Cys Lys Gly Ser Gly Cys Ile Ile Ser
            20                  25                  30 tct tac tgg atc agc tgg gtt cgt cag atg ccg ggc aag ggc ctg gaa        144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg        192
Trp Met Gly Lys Ile Asp Pro Gly Asp Ser Tyr Ile Asn Tyr Ser Pro
    50                  55                  60 agc ttt cag ggc cat gtt acc atc agc gcc gat aaa agc att aac acc        240
Ser Phe Gln Gly His Val Thr Ile Ser Ala Asp Lys Ser Ile Asn Thr
65                  70                  75                  80 gct tac ctg caa tgg aac agc ctg aaa gcg agc gac acc gcg atg tac        288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg        336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt        384
Gly Gln Gly Thr Leu Val Thr Val Ser Ser Gly Gly Gly Gly Ser Gly
        115                 120                 125 ggc ggc gga tcc ggt ggt ggc ggc agc ggc ggc ggc agc gat gtt            432
Gly Gly Gly Ser Gly Gly Gly Gly Ser Gly Gly Gly Gly Ser Asp Val
    130                 135                 140 gtg atg acc cag agc ccg agc ttc ctg agc gcg ttc gtt ggt gac cgt        480
Val Met Thr Gln Ser Pro Ser Phe Leu Ser Ala Phe Val Gly Asp Arg
145                 150                 155                 160 atc acc att acc tgc cgc gcc agc agc ggc atc agc cgc tat ctg gcg        528
Ile Thr Ile Thr Cys Arg Ala Ser Ser Gly Ile Ser Arg Tyr Leu Ala
                165                 170                 175 tgg tat cag caa gca ccg ggt aaa gca ccg aaa ctg ctg atc tat gct        576
Trp Tyr Gln Gln Ala Pro Gly Lys Ala Pro Lys Leu Leu Ile Tyr Ala
            180                 185                 190 gca agc acc ctg caa acc ggc gtt ccg agc cgt ttt agc ggt agc ggc        624
Ala Ser Thr Leu Gln Thr Gly Val Pro Ser Arg Phe Ser Gly Ser Gly
        195                 200                 205 agc ggc acc gag ttc acc ctg acc atc aac agc ctg caa ccg gag gat        672
Ser Gly Thr Glu Phe Thr Leu Thr Ile Asn Ser Leu Gln Pro Glu Asp
    210                 215                 220 ttt gcc acc tat tac tgc caa cac ctg aat agc tat ccg ctg acc ttc        720
Phe Ala Thr Tyr Tyr Cys Gln His Leu Asn Ser Tyr Pro Leu Thr Phe
```

```
ggt ggc ggc acc aaa gtg gac atc aaa cgc gcg taa taa                759
Gly Gly Gly Thr Lys Val Asp Ile Lys Arg Ala
                245                 250
```

<210> SEQ ID NO 30
<211> LENGTH: 251
<212> TYPE: PRT
<213> ORGANISM: Artificial
<220> FEATURE:
<223> OTHER INFORMATION: Synthetic Construct

<400> SEQUENCE: 30

```
Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Cys Ile Ile Ser
                20                  25                  30

Ser Tyr Trp Ile Ser Trp Val Arg Gln Met Pro Gly Lys Gly Leu Glu
            35                  40                  45

Trp Met Gly Lys Ile Asp Pro Gly Asp Ser Tyr Ile Asn Tyr Ser Pro
        50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
                100                 105                 110

Gly Gln Gly Thr Leu Val Thr Val Ser Ser Gly Gly Gly Gly Ser Gly
            115                 120                 125

Gly Gly Gly Ser Gly Gly Gly Gly Ser Gly Gly Gly Gly Ser Asp Val
        130                 135                 140

Val Met Thr Gln Ser Pro Ser Phe Leu Ser Ala Phe Val Gly Asp Arg
145                 150                 155                 160

Ile Thr Ile Thr Cys Arg Ala Ser Ser Gly Ile Ser Arg Tyr Leu Ala
                165                 170                 175

Trp Tyr Gln Gln Ala Pro Gly Lys Ala Pro Lys Leu Leu Ile Tyr Ala
                180                 185                 190

Ala Ser Thr Leu Gln Thr Gly Val Pro Ser Arg Phe Ser Gly Ser Gly
            195                 200                 205

Ser Gly Thr Glu Phe Thr Leu Thr Ile Asn Ser Leu Gln Pro Glu Asp
        210                 215                 220

Phe Ala Thr Tyr Tyr Cys Gln His Leu Asn Ser Tyr Pro Leu Thr Phe
225                 230                 235                 240

Gly Gly Gly Thr Lys Val Asp Ile Lys Arg Ala
                245                 250
```

<210> SEQ ID NO 31
<211> LENGTH: 762
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(762)

<400> SEQUENCE: 31

```
atg gat gtt gtg atg acc cag agc ccg agc ttc ctg agc gcg ttc gtt      48
Met Asp Val Val Met Thr Gln Ser Pro Ser Phe Leu Ser Ala Phe Val
```

```
                1               5                      10                      15
ggt gac cgt atc acc att acc tgc cgc gcc agc agc ggc atc agc cgc         96
Gly Asp Arg Ile Thr Ile Thr Cys Arg Ala Ser Ser Gly Ile Ser Arg
                20                      25                      30 tat ctg gcg tgg tat cag caa gca ccg ggt aaa gca ccg aaa ctg ctg         144
Tyr Leu Ala Trp Tyr Gln Gln Ala Pro Gly Lys Ala Pro Lys Leu Leu
            35                      40                      45 atc tat gct gca agc acc ctg caa acc ggc gtt ccg agc cgt ttt agc         192
Ile Tyr Ala Ala Ser Thr Leu Gln Thr Gly Val Pro Ser Arg Phe Ser
        50                      55                      60 ggt agc ggc agc ggc acc gag ttc acc ctg acc atc aac agc ctg caa         240
Gly Ser Gly Ser Gly Thr Glu Phe Thr Leu Thr Ile Asn Ser Leu Gln
65                      70                      75                      80 ccg gag gat ttt gcc acc tat tac tgc caa cac ctg aat agc tat ccg         288
Pro Glu Asp Phe Ala Thr Tyr Tyr Cys Gln His Leu Asn Ser Tyr Pro
                    85                      90                      95 ctg acc ttc ggt ggc ggc acc aaa gtg gac atc aaa cgc gcg agc ggt         336
Leu Thr Phe Gly Gly Gly Thr Lys Val Asp Ile Lys Arg Ala Ser Gly
                100                     105                     110 ggt ggc ggc agc ggt ggt ggc gga tcc ggt ggt ggc ggc agc ggc ggc         384
Gly Gly Gly Ser Gly Gly Gly Gly Ser Gly Gly Gly Gly Ser Gly Gly
            115                     120                     125 ggc ggc agc gct gaa gtt caa ctt gtt gaa tct ggt gct gaa gtt aaa         432
Gly Gly Ser Ala Glu Val Gln Leu Val Glu Ser Gly Ala Glu Val Lys
        130                     135                     140 aaa ccg ggt gaa tct ctg cgt atc tct tgc aaa ggt tct ggt tgc atc         480
Lys Pro Gly Glu Ser Leu Arg Ile Ser Cys Lys Gly Ser Gly Cys Ile
145                     150                     155                     160 atc tct tct tac tgg atc agc tgg gtt cgt cag atg ccg ggc aag ggc         528
Ile Ser Ser Tyr Trp Ile Ser Trp Val Arg Gln Met Pro Gly Lys Gly
                    165                     170                     175 ctg gaa tgg atg ggt aaa att gat ccg ggc gac agc tat att aac tac         576
Leu Glu Trp Met Gly Lys Ile Asp Pro Gly Asp Ser Tyr Ile Asn Tyr
                180                     185                     190 agc ccg agc ttt cag ggc cat gtt acc atc agc gcc gat aaa agc att         624
Ser Pro Ser Phe Gln Gly His Val Thr Ile Ser Ala Asp Lys Ser Ile
            195                     200                     205 aac acc gct tac ctg caa tgg aac agc ctg aaa gcg agc gac acc gcg         672
Asn Thr Ala Tyr Leu Gln Trp Asn Ser Leu Lys Ala Ser Asp Thr Ala
        210                     215                     220 atg tac tac tgt gcc cgt ggc ggt cgt gac ttc ggt gat agc ttc gat         720
Met Tyr Tyr Cys Ala Arg Gly Gly Arg Asp Phe Gly Asp Ser Phe Asp
225                     230                     235                     240 tac tgg ggt cag ggc acc ctg gtg acc gtg agc agc taa taa             762
Tyr Trp Gly Gln Gly Thr Leu Val Thr Val Ser Ser
                    245                     250

<210> SEQ ID NO 32
<211> LENGTH: 252
<212> TYPE: PRT
<213> ORGANISM: Artificial
<220> FEATURE:
<223> OTHER INFORMATION: Synthetic Construct

<400> SEQUENCE: 32

Met Asp Val Val Met Thr Gln Ser Pro Ser Phe Leu Ser Ala Phe Val
1               5                       10                      15

Gly Asp Arg Ile Thr Ile Thr Cys Arg Ala Ser Ser Gly Ile Ser Arg
                20                      25                      30

Tyr Leu Ala Trp Tyr Gln Gln Ala Pro Gly Lys Ala Pro Lys Leu Leu
```

```
                35                   40                  45
Ile Tyr Ala Ala Ser Thr Leu Gln Thr Gly Val Pro Ser Arg Phe Ser
     50                  55                  60

Gly Ser Gly Ser Gly Thr Glu Phe Thr Leu Thr Ile Asn Ser Leu Gln
 65                  70                  75                  80

Pro Glu Asp Phe Ala Thr Tyr Tyr Cys Gln His Leu Asn Ser Tyr Pro
                 85                  90                  95

Leu Thr Phe Gly Gly Gly Thr Lys Val Asp Ile Lys Arg Ala Ser Gly
             100                 105                 110

Gly Gly Gly Ser Gly Gly Gly Ser Gly Gly Gly Gly Ser Gly Gly
         115                 120                 125

Gly Gly Ser Ala Glu Val Gln Leu Val Glu Ser Gly Ala Glu Val Lys
     130                 135                 140

Lys Pro Gly Glu Ser Leu Arg Ile Ser Cys Lys Gly Ser Gly Cys Ile
145                 150                 155                 160

Ile Ser Ser Tyr Trp Ile Ser Trp Val Arg Gln Met Pro Gly Lys Gly
                165                 170                 175

Leu Glu Trp Met Gly Lys Ile Asp Pro Gly Asp Ser Tyr Ile Asn Tyr
            180                 185                 190

Ser Pro Ser Phe Gln Gly His Val Thr Ile Ser Ala Asp Lys Ser Ile
        195                 200                 205

Asn Thr Ala Tyr Leu Gln Trp Asn Ser Leu Lys Ala Ser Asp Thr Ala
    210                 215                 220

Met Tyr Tyr Cys Ala Arg Gly Gly Arg Asp Phe Gly Asp Ser Phe Asp
225                 230                 235                 240

Tyr Trp Gly Gln Gly Thr Leu Val Thr Val Ser Ser
                245                 250

<210> SEQ ID NO 33
<211> LENGTH: 774
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(774)
<220> FEATURE:
<221> NAME/KEY: misc_feature
<222> LOCATION: (292)..(294)
<223> OTHER INFORMATION: n is a, c, g, or t

<400> SEQUENCE: 33 atg gct gaa gtt caa ctt gtt gaa tct ggt gct gaa gtt aaa aaa ccg    48
Met Ala Glu Val Gln Leu Val Glu Ser Gly Ala Glu Val Lys Lys Pro
 1               5                  10                  15 ggt gaa tct ctg cgt atc tct tgc aaa ggt tct ggt tgc atc atc tct    96
Gly Glu Ser Leu Arg Ile Ser Cys Lys Gly Ser Gly Cys Ile Ile Ser
            20                  25                  30 tct tac tgg atc agc tgg gtt cgt cag atg ccg ggc aag ggc ctg gaa   144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg   192
Trp Met Gly Lys Ile Asp Pro Gly Asp Ser Tyr Ile Asn Tyr Ser Pro
     50                  55                  60 agc ttt cag ggc cat gtt acc atc agc gcc gat aaa agc att aac acc   240
Ser Phe Gln Gly His Val Thr Ile Ser Ala Asp Lys Ser Ile Asn Thr
 65                  70                  75                  80 gct tac ctg caa tgg aac agc ctg aaa gcg agc gac acc gcg atg tac   288
```

```
Ala Tyr Leu Gln Trp Asn Ser Leu Lys Ala Ser Asp Thr Ala Met Tyr
             85                  90                  95 tac nnn gcc cgt ggc ggt cgt gac ttc ggt gat agc ttc gat tac tgg      336
Tyr Xaa Ala Arg Gly Gly Arg Asp Phe Gly Asp Ser Phe Asp Tyr Trp
        100                 105                 110 ggt cag ggc acc ctg gtg acc gtg agc agc ggt ggc ggc agc ggt          384
Gly Gln Gly Thr Leu Val Thr Val Ser Ser Gly Gly Gly Ser Gly
        115                 120                 125 ggt ggc ggc agc ggc ggc ggc agc gat gtt gtg atg acc cag agc          432
Gly Gly Gly Ser Gly Gly Gly Ser Asp Val Val Met Thr Gln Ser
130                 135                 140 ccg agc ttc ctg agc gcg ttc gtt ggt gac cgt atc acc att acc tgc      480
Pro Ser Phe Leu Ser Ala Phe Val Gly Asp Arg Ile Thr Ile Thr Cys
145                 150                 155                 160 cgc gcc agc agc ggc atc agc cgc tat ctg gcg tgg tat cag caa gca      528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa      576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc      624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac      672
Thr Leu Thr Ile Asn Ser Leu Gln Pro Glu Asp Phe Ala Thr Tyr Tyr
210                 215                 220 tgc caa cac ctg aat agc tat ccg ctg acc ttc ggt ggc ggc acc aaa      720
Cys Gln His Leu Asn Ser Tyr Pro Leu Thr Phe Gly Gly Gly Thr Lys
225                 230                 235                 240 gtg gac atc aaa cgc gcg gcc gca ctc gag cac cac cac cac cac cac      768
Val Asp Ile Lys Arg Ala Ala Ala Leu Glu His His His His His His
                245                 250                 255 taa taa                                                              774
```

<210> SEQ ID NO 34
<211> LENGTH: 256
<212> TYPE: PRT
<213> ORGANISM: Artificial
<220> FEATURE:
<221> NAME/KEY: misc_feature
<222> LOCATION: (98)..(98)
<223> OTHER INFORMATION: The 'Xaa' at location 98 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 34

```
Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Cys Ile Ile Ser
                20                  25                  30

Ser Tyr Trp Ile Ser Trp Val Arg Gln Met Pro Gly Lys Gly Leu Glu
            35                  40                  45

Trp Met Gly Lys Ile Asp Pro Gly Asp Ser Tyr Ile Asn Tyr Ser Pro
        50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95
```

```
Tyr Xaa Ala Arg Gly Gly Arg Asp Phe Gly Asp Ser Phe Asp Tyr Trp
        100                 105                 110

Gly Gln Gly Thr Leu Val Thr Val Ser Ser Gly Gly Gly Ser Gly
        115                 120                 125

Gly Gly Gly Ser Gly Gly Gly Ser Asp Val Val Met Thr Gln Ser
    130                 135                 140

Pro Ser Phe Leu Ser Ala Phe Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
                180                 185                 190

Thr Gly Val Pro Ser Arg Phe Ser Gly Ser Gly Ser Gly Thr Glu Phe
            195                 200                 205

Thr Leu Thr Ile Asn Ser Leu Gln Pro Glu Asp Phe Ala Thr Tyr Tyr
        210                 215                 220

Cys Gln His Leu Asn Ser Tyr Pro Leu Thr Phe Gly Gly Gly Thr Lys
225                 230                 235                 240

Val Asp Ile Lys Arg Ala Ala Ala Leu Glu His His His His His
                245                 250                 255
```

```
<210> SEQ ID NO 35
<211> LENGTH: 744
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(744)

<400> SEQUENCE: 35
```

```
atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt tat agc atc tct      96
Gly Glu Ser Leu Arg Ile Ser Cys Lys Gly Ser Gly Tyr Ser Ile Ser
            20                  25                  30 tct tac tgg atc agc tgg gtt cgt cag atg ccg ggc aag ggc ctg gaa    144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg    192
Trp Met Gly Lys Ile Asp Pro Gly Asp Ser Tyr Ile Asn Tyr Ser Pro
    50                  55                  60 agc ttt cag ggc cgt gtt acc atc agc gcc gat aaa agc att aac acc    240
Ser Phe Gln Gly Arg Val Thr Ile Ser Ala Asp Lys Ser Ile Asn Thr
65                  70                  75                  80 gct tac ctg caa tgg aac agc ctg aaa gcg agc gac acc gcg atg tac    288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg    336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt    384
Gly Gln Gly Thr Leu Val Thr Val Ser Ser Gly Gly Gly Gly Ser Gly
        115                 120                 125 ggt ggc ggc agc ggc ggc ggc agc gat att cag atg acc cag agc        432
Gly Gly Gly Ser Gly Gly Gly Ser Asp Ile Gln Met Thr Gln Ser
    130                 135                 140
```

```
ccg agc tcc ctg agc gcg agc gtt ggt gac cgt atc acc att acc tgc      480
Pro Ser Ser Leu Ser Ala Ser Val Gly Asp Arg Ile Thr Ile Thr Cys
145                 150                 155                 160 cgc gcc agc agc ggc atc agc cgc tat ctg gcg tgg tat cag caa gca      528
Arg Ala Ser Ser Gly Ile Ser Arg Tyr Leu Ala Trp Tyr Gln Gln Ala
                165                 170                 175 ccg ggt aaa gca ccg aaa ctg ctg atc tat gct gca agc acc ctg caa      576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc      624
Thr Gly Val Pro Ser Arg Phe Ser Gly Ser Gly Ser Gly Thr Glu Phe
        195                 200                 205 acc ctg acc atc aac agc ctg caa ccg gag gat ttt gcc acc tat tac      672
Thr Leu Thr Ile Asn Ser Leu Gln Pro Glu Asp Phe Ala Thr Tyr Tyr
    210                 215                 220 tgc caa cac ctg aat agc tat ccg ctg acc ttc ggt ggc ggc acc aaa      720
Cys Gln His Leu Asn Ser Tyr Pro Leu Thr Phe Gly Gly Gly Thr Lys
225                 230                 235                 240 gtg gac atc aaa cgc gcg taa taa                                      744
Val Asp Ile Lys Arg Ala
                245
```

<210> SEQ ID NO 36
<211> LENGTH: 246
<212> TYPE: PRT
<213> ORGANISM: Artificial
<220> FEATURE:
<223> OTHER INFORMATION: Synthetic Construct

<400> SEQUENCE: 36

```
Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Tyr Ser Ile Ser
                20                  25                  30

Ser Tyr Trp Ile Ser Trp Val Arg Gln Met Pro Gly Lys Gly Leu Glu
            35                  40                  45

Trp Met Gly Lys Ile Asp Pro Gly Asp Ser Tyr Ile Asn Tyr Ser Pro
        50                  55                  60

Ser Phe Gln Gly Arg Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Ile Thr Ile Thr Cys
145                 150                 155                 160

Arg Ala Ser Ser Gly Ile Ser Arg Tyr Leu Ala Trp Tyr Gln Gln Ala
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Asn Ser Leu Gln Pro Glu Asp Phe Ala Thr Tyr Tyr
    210                 215                 220
```

```
Cys Gln His Leu Asn Ser Tyr Pro Leu Thr Phe Gly Gly Gly Thr Lys
225                 230                 235                 240

Val Asp Ile Lys Arg Ala
            245

<210> SEQ ID NO 37
<211> LENGTH: 744
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(744)

<400> SEQUENCE: 37 atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt tat agc atc tct      96
Gly Glu Ser Leu Arg Ile Ser Cys Lys Gly Ser Gly Tyr Ser Ile Ser
            20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
    50                  55                  60 agc ttt cag ggc cgt gtt acc atc agc gcc gat aaa agc att aac acc     240
Ser Phe Gln Gly Arg Val Thr Ile Ser Ala Asp Lys Ser Ile Asn Thr
65                  70                  75                  80 gct tac ctg caa tgg agc agc ctg aaa gcg agc gac acc gcg atg tac     288
Ala Tyr Leu Gln Trp Ser Ser Leu Lys Ala Ser Asp Thr Ala Met Tyr
                85                  90                  95 tac tgt gcc cgt ggc ggt cgt gac ttc ggt gat agc ttc gat tac tgg     336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt     384
Gly Gln Gly Thr Leu Val Thr Val Ser Ser Gly Gly Gly Gly Ser Gly
        115                 120                 125 ggc ggc agc ggc ggc ggc agc gat att cag atg acc cag agc             432
Gly Gly Ser Gly Gly Gly Gly Ser Asp Ile Gln Met Thr Gln Ser
    130                 135                 140 ccg agc tcc ctg agc gcg agc gtt ggt gac cgt atc acc att acc tgc     480
Pro Ser Ser Leu Ser Ala Ser Val Gly Asp Arg Ile Thr Ile Thr Cys
145                 150                 155                 160 cgc gcc agc agc ggc atc agc cgc tat ctg gcg tgg tat cag caa aaa     528
Arg Ala Ser Ser Gly Ile Ser Arg Tyr Leu Ala Trp Tyr Gln Gln Lys
                165                 170                 175 ccg ggt aaa gca ccg aaa ctg ctg atc tat gct gca agc acc ctg caa     576
Pro Gly Lys Ala Pro Lys Leu Leu Ile Tyr Ala Ala Ser Thr Leu Gln
            180                 185                 190 acc ggc gtt ccg agc cgt ttt agc ggt agc ggc agc ggc acc gag ttc     624
Thr Gly Val Pro Ser Arg Phe Ser Gly Ser Gly Ser Gly Thr Glu Phe
        195                 200                 205 acc ctg acc atc agc agc ctg caa ccg gag gat ttt gcc acc tat tac     672
Thr Leu Thr Ile Ser Ser Leu Gln Pro Glu Asp Phe Ala Thr Tyr Tyr
    210                 215                 220 tgc caa cac ctg aat agc tat ccg ctg acc ttc ggt ggc ggc acc aaa     720
Cys Gln His Leu Asn Ser Tyr Pro Leu Thr Phe Gly Gly Gly Thr Lys
225                 230                 235                 240
```

```
gtg gac atc aaa cgc gcg taa taa                                    744
Val Asp Ile Lys Arg Ala
            245

<210> SEQ ID NO 38
<211> LENGTH: 246
<212> TYPE: PRT
<213> ORGANISM: Artificial
<220> FEATURE:
<223> OTHER INFORMATION: Synthetic Construct

<400> SEQUENCE: 38

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Tyr Ser Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly Arg Val Thr Ile Ser Ala Asp Lys Ser Ile Asn Thr
65                  70                  75                  80

Ala Tyr Leu Gln Trp Ser Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Ser Gly
        115                 120                 125

Gly Gly Gly Ser Gly Gly Gly Ser Asp Ile Gln Met Thr Gln Ser
    130                 135                 140

Pro Ser Ser Leu Ser Ala Ser Val Gly Asp Arg Ile Thr Ile Thr Cys
145                 150                 155                 160

Arg Ala Ser Ser Gly Ile Ser Arg Tyr Leu Ala Trp Tyr Gln Gln Lys
                165                 170                 175

Pro Gly Lys Ala Pro Lys Leu Leu Ile Tyr Ala Ala Ser Thr Leu Gln
            180                 185                 190

Thr Gly Val Pro Ser Arg Phe Ser Gly Ser Gly Ser Gly Thr Glu Phe
        195                 200                 205

Thr Leu Thr Ile Ser Ser Leu Gln Pro Glu Asp Phe Ala Thr Tyr Tyr
    210                 215                 220

Cys Gln His Leu Asn Ser Tyr Pro Leu Thr Phe Gly Gly Gly Thr Lys
225                 230                 235                 240

Val Asp Ile Lys Arg Ala
            245

<210> SEQ ID NO 39
<211> LENGTH: 774
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(774)

<400> SEQUENCE: 39 atg gct gaa gtt caa ctt gtt gaa tct ggt gct gaa gtt aaa aaa ccg    48
Met Ala Glu Val Gln Leu Val Glu Ser Gly Ala Glu Val Lys Lys Pro
1               5                   10                  15
```

```
ggt gaa tct ctg cgt atc tct tgc aaa ggt tct ggt tgc atc atc tct      96
Gly Glu Ser Leu Arg Ile Ser Cys Lys Gly Ser Gly Cys Ile Ile Ser
         20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
         35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
 50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
 65                  70                  75                  80 gct tac ctg caa tgg aac agc ctg aaa gcg agc gac acc gcg atg tac     288
Ala Tyr Leu Gln Trp Asn Ser Leu Lys Ala Ser Asp Thr Ala Met Tyr
                 85                  90                  95 tac tgt gcc cgt ggc ggt cgt gac ttc ggt gat agc ttc gat tac tgg     336
Tyr Cys Ala Arg Gly Gly Arg Asp Phe Gly Asp Ser Phe Asp Tyr Trp
                100                 105                 110 ggt cag ggc acc ctg gtg acc gtg agc agc ggt ggt ggc ggc agc ggt     384
Gly Gln Gly Thr Leu Val Thr Val Ser Ser Gly Gly Gly Gly Ser Gly
        115                 120                 125 ggt ggc gga tcc ggt ggt ggc ggc tcc ggt ggt ggc ggc agc ggc ggc     432
Gly Gly Gly Ser Gly Gly Gly Gly Ser Gly Gly Gly Gly Ser Gly Gly
130                 135                 140 ggc agc gat gtt gtg atg acc cag agc ccg agc ttc ctg agc gcg         480
Gly Ser Asp Val Val Met Thr Gln Ser Pro Ser Phe Leu Ser Ala
145                 150                 155                 160 ttc gtt ggt gac cgt atc acc att acc tgc cgc gcc agc agc ggc atc     528
Phe Val Gly Asp Arg Ile Thr Ile Thr Cys Arg Ala Ser Ser Gly Ile
                165                 170                 175 agc cgc tat ctg gcg tgg tat cag caa gca ccg ggt aaa gca ccg aaa     576
Ser Arg Tyr Leu Ala Trp Tyr Gln Gln Ala Pro Gly Lys Ala Pro Lys
                180                 185                 190 ctg ctg atc tat gct gca agc acc ctg caa acc ggc gtt ccg agc cgt     624
Leu Leu Ile Tyr Ala Ala Ser Thr Leu Gln Thr Gly Val Pro Ser Arg
        195                 200                 205 ttt agc ggt agc ggc agc ggc acc gag ttc acc ctg acc atc aac agc     672
Phe Ser Gly Ser Gly Ser Gly Thr Glu Phe Thr Leu Thr Ile Asn Ser
210                 215                 220 ctg caa ccg gag gat ttt gcc acc tat tac tgc caa cac ctg aat agc     720
Leu Gln Pro Glu Asp Phe Ala Thr Tyr Tyr Cys Gln His Leu Asn Ser
225                 230                 235                 240 tat ccg ctg acc ttc ggt ggc ggc acc aaa gtg gac atc aaa cgc gcg     768
Tyr Pro Leu Thr Phe Gly Gly Gly Thr Lys Val Asp Ile Lys Arg Ala
                245                 250                 255 taa taa                                                             774

<210> SEQ ID NO 40
<211> LENGTH: 256
<212> TYPE: PRT
<213> ORGANISM: Artificial
<220> FEATURE:
<223> OTHER INFORMATION: Synthetic Construct

<400> SEQUENCE: 40

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Cys Ile Ile Ser
            20                  25                  30
```

-continued

```
Ser Tyr Trp Ile Ser Trp Val Arg Gln Met Pro Gly Lys Gly Leu Glu
         35                  40                  45

Trp Met Gly Lys Ile Asp Pro Gly Asp Ser Tyr Ile Asn Tyr Ser Pro
 50                  55                  60

Ser Phe Gln Gly His Val Thr Ile Ser Ala Asp Lys Ser Ile Asn Thr
 65                  70                  75                  80

Ala Tyr Leu Gln Trp Asn Ser Leu Lys Ala Ser Asp Thr Ala Met Tyr
             85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Ser Gly
        115                 120                 125

Gly Gly Gly Ser Gly Gly Gly Ser Gly Gly Gly Ser Gly Gly
130                 135                 140

Gly Gly Ser Asp Val Val Met Thr Gln Ser Pro Ser Phe Leu Ser Ala
145                 150                 155                 160

Phe Val Gly Asp Arg Ile Thr Ile Thr Cys Arg Ala Ser Ser Gly Ile
                165                 170                 175

Ser Arg Tyr Leu Ala Trp Tyr Gln Gln Ala Pro Gly Lys Ala Pro Lys
            180                 185                 190

Leu Leu Ile Tyr Ala Ala Ser Thr Leu Gln Thr Gly Val Pro Ser Arg
        195                 200                 205

Phe Ser Gly Ser Gly Ser Gly Thr Glu Phe Thr Leu Thr Ile Asn Ser
    210                 215                 220

Leu Gln Pro Glu Asp Phe Ala Thr Tyr Tyr Cys Gln His Leu Asn Ser
225                 230                 235                 240

Tyr Pro Leu Thr Phe Gly Gly Gly Thr Lys Val Asp Ile Lys Arg Ala
                245                 250                 255
```

<210> SEQ ID NO 41
<211> LENGTH: 789
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(789)

<400> SEQUENCE: 41

```
atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
 1               5                  10                  15 ggt gaa tct ctg cgt atc tct tgc aaa ggt tct ggt tgc atc atc tct      96
Gly Glu Ser Leu Arg Ile Ser Cys Lys Gly Ser Gly Cys Ile Ile Ser
             20                  25                  30 tct tac tgg atc agc tgg gtt cgt cag atg ccg ggc aag ggc ctg gaa    144
Ser Tyr Trp Ile Ser Trp Val Arg Gln Met Pro Gly Lys Gly Leu Glu
         35                  40                  45 tgg atg ggt aaa att gat ccg ggc gac agc tat att aac tac agc ccg    192
Trp Met Gly Lys Ile Asp Pro Gly Asp Ser Tyr Ile Asn Tyr Ser Pro
 50                  55                  60 agc ttt cag ggc cat gtt acc atc agc gcc gat aaa agc att aac acc    240
Ser Phe Gln Gly His Val Thr Ile Ser Ala Asp Lys Ser Ile Asn Thr
 65                  70                  75                  80 gct tac ctg caa tgg aac agc ctg aaa gcg agc gac acc gcg atg tac    288
Ala Tyr Leu Gln Trp Asn Ser Leu Lys Ala Ser Asp Thr Ala Met Tyr
             85                  90                  95
```

| | |
|---|---|
| tac tgt gcc cgt ggc ggt cgt gac ttc ggt gat agc ttc gat tac tgg<br>Tyr Cys Ala Arg Gly Gly Arg Asp Phe Gly Asp Ser Phe Asp Tyr Trp<br>              100                          105                      110 | 336 |
| ggt cag ggc acc ctg gtg acc gtg agc agc ggt ggt ggc ggc agc ggt<br>Gly Gln Gly Thr Leu Val Thr Val Ser Ser Gly Gly Gly Gly Ser Gly<br>            115                          120                      125 | 384 |
| ggt ggc gga tct ggt ggt ggc ggc agc ggt ggt ggc gga tcc ggt ggt<br>Gly Gly Gly Ser Gly Gly Gly Gly Ser Gly Gly Gly Gly Ser Gly Gly<br>130                          135                          140 | 432 |
| ggc ggc agc ggc ggc ggc ggc agc gat gtt gtg atg acc cag agc ccg<br>Gly Gly Ser Gly Gly Gly Gly Ser Asp Val Val Met Thr Gln Ser Pro<br>145                          150                          155                      160 | 480 |
| agc ttc ctg agc gcg ttc gtt ggt gac cgt atc acc att acc tgc cgc<br>Ser Phe Leu Ser Ala Phe Val Gly Asp Arg Ile Thr Ile Thr Cys Arg<br>                      165                          170                        175 | 528 |
| gcc agc agc ggc atc agc cgc tat ctg gcg tgg tat cag caa gca ccg<br>Ala Ser Ser Gly Ile Ser Arg Tyr Leu Ala Trp Tyr Gln Gln Ala Pro<br>                    180                          185                        190 | 576 |
| ggt aaa gca ccg aaa ctg ctg atc tat gct gca agc acc ctg caa acc<br>Gly Lys Ala Pro Lys Leu Leu Ile Tyr Ala Ala Ser Thr Leu Gln Thr<br>            195                          200                      205 | 624 |
| ggc gtt ccg agc cgt ttt agc ggt agc ggc agc ggc acc gag ttc acc<br>Gly Val Pro Ser Arg Phe Ser Gly Ser Gly Ser Gly Thr Glu Phe Thr<br>210                          215                          220 | 672 |
| ctg acc atc aac agc ctg caa ccg gag gat ttt gcc acc tat tac tgc<br>Leu Thr Ile Asn Ser Leu Gln Pro Glu Asp Phe Ala Thr Tyr Tyr Cys<br>225                          230                          235                      240 | 720 |
| caa cac ctg aat agc tat ccg ctg acc ttc ggt ggc ggc acc aaa gtg<br>Gln His Leu Asn Ser Tyr Pro Leu Thr Phe Gly Gly Gly Thr Lys Val<br>                    245                          250                        255 | 768 |
| gac atc aaa cgc gcg taa taa<br>Asp Ile Lys Arg Ala<br>            260 | 789 |

```
<210> SEQ ID NO 42
<211> LENGTH: 261
<212> TYPE: PRT
<213> ORGANISM: Artificial
<220> FEATURE:
<223> OTHER INFORMATION: Synthetic Construct

<400> SEQUENCE: 42
```

Met Ala Glu Val Gln Leu Val Glu Ser Gly Ala Glu Val Lys Lys Pro
1                 5                     10                   15

Gly Glu Ser Leu Arg Ile Ser Cys Lys Gly Ser Gly Cys Ile Ile Ser
               20                     25                     30

Ser Tyr Trp Ile Ser Trp Val Arg Gln Met Pro Gly Lys Gly Leu Glu
               35                     40                     45

Trp Met Gly Lys Ile Asp Pro Gly Asp Ser Tyr Ile Asn Tyr Ser Pro
 50                       55                     60

Ser Phe Gln Gly His Val Thr Ile Ser Ala Asp Lys Ser Ile Asn Thr
65                      70                     75                     80

Ala Tyr Leu Gln Trp Asn Ser Leu Lys Ala Ser Asp Thr Ala Met Tyr
                   85                     90                     95

Tyr Cys Ala Arg Gly Gly Arg Asp Phe Gly Asp Ser Phe Asp Tyr Trp
              100                     105                     110

Gly Gln Gly Thr Leu Val Thr Val Ser Ser Gly Gly Gly Gly Ser Gly
            115                     120                     125

Gly Gly Gly Ser Gly Gly Gly Gly Ser Gly Gly Gly Gly Ser Gly Gly

```
                130               135               140
Gly Gly Ser Gly Gly Gly Ser Asp Val Val Met Thr Gln Ser Pro
145                 150                 155                 160

Ser Phe Leu Ser Ala Phe Val Gly Asp Arg Ile Thr Ile Thr Cys Arg
                165                 170                 175

Ala Ser Ser Gly Ile Ser Arg Tyr Leu Ala Trp Tyr Gln Gln Ala Pro
                180                 185                 190

Gly Lys Ala Pro Lys Leu Leu Ile Tyr Ala Ala Ser Thr Leu Gln Thr
                195                 200                 205

Gly Val Pro Ser Arg Phe Ser Gly Ser Gly Ser Gly Thr Glu Phe Thr
210                 215                 220

Leu Thr Ile Asn Ser Leu Gln Pro Glu Asp Phe Ala Thr Tyr Tyr Cys
225                 230                 235                 240

Gln His Leu Asn Ser Tyr Pro Leu Thr Phe Gly Gly Gly Thr Lys Val
                245                 250                 255

Asp Ile Lys Arg Ala
            260

<210> SEQ ID NO 43
<211> LENGTH: 777
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(777)

<400> SEQUENCE: 43 atg gat gtt gtg atg acc cag agc ccg agc ttc ctg agc gcg ttc gtt      48
Met Asp Val Val Met Thr Gln Ser Pro Ser Phe Leu Ser Ala Phe Val
1               5                   10                  15 ggt gac cgt atc acc att acc tgc cgc gcc agc agc ggc atc agc cgc      96
Gly Asp Arg Ile Thr Ile Thr Cys Arg Ala Ser Ser Gly Ile Ser Arg
            20                  25                  30 tat ctg gcg tgg tat cag caa gca ccg ggt aaa gca ccg aaa ctg ctg     144
Tyr Leu Ala Trp Tyr Gln Gln Ala Pro Gly Lys Ala Pro Lys Leu Leu
        35                  40                  45 atc tat gct gca agc acc ctg caa acc ggc gtt ccg agc cgt ttt agc     192
Ile Tyr Ala Ala Ser Thr Leu Gln Thr Gly Val Pro Ser Arg Phe Ser
    50                  55                  60 ggt agc ggc agc ggc acc gag ttc acc ctg acc atc aac agc ctg caa     240
Gly Ser Gly Ser Gly Thr Glu Phe Thr Leu Thr Ile Asn Ser Leu Gln
65                  70                  75                  80 ccg gag gat ttt gcc acc tat tac tgc caa cac ctg aat agc tat ccg     288
Pro Glu Asp Phe Ala Thr Tyr Tyr Cys Gln His Leu Asn Ser Tyr Pro
                85                  90                  95 ctg acc ttc ggt ggc ggc acc aaa gtg gac atc aaa cgc gcg agc ggt     336
Leu Thr Phe Gly Gly Gly Thr Lys Val Asp Ile Lys Arg Ala Ser Gly
            100                 105                 110 ggt ggc ggc agc ggt ggt ggc gga tcc ggt ggt ggc ggc tcc ggt ggt     384
Gly Gly Gly Ser Gly Gly Gly Gly Ser Gly Gly Gly Gly Ser Gly Gly
        115                 120                 125 ggc ggc agc ggc ggc ggc ggc agc gct gaa gtt caa ctt gtt gaa tct     432
Gly Gly Ser Gly Gly Gly Gly Ser Ala Glu Val Gln Leu Val Glu Ser
    130                 135                 140 ggt gct gaa gtt aaa aaa ccg ggt gaa tct ctg cgt atc tct tgc aaa     480
Gly Ala Glu Val Lys Lys Pro Gly Glu Ser Leu Arg Ile Ser Cys Lys
145                 150                 155                 160
```

```
ggt tct ggt tgc atc atc tct tct tac tgg atc agc tgg gtt cgt cag      528
Gly Ser Gly Cys Ile Ile Ser Ser Tyr Trp Ile Ser Trp Val Arg Gln
            165                 170                 175 atg ccg ggc aag ggc ctg gaa tgg atg ggt aaa att gat ccg ggc gac      576
Met Pro Gly Lys Gly Leu Glu Trp Met Gly Lys Ile Asp Pro Gly Asp
        180                 185                 190 agc tat att aac tac agc ccg agc ttt cag ggc cat gtt acc atc agc      624
Ser Tyr Ile Asn Tyr Ser Pro Ser Phe Gln Gly His Val Thr Ile Ser
    195                 200                 205 gcc gat aaa agc att aac acc gct tac ctg caa tgg aac agc ctg aaa      672
Ala Asp Lys Ser Ile Asn Thr Ala Tyr Leu Gln Trp Asn Ser Leu Lys
210                 215                 220 gcg agc gac acc gcg atg tac tac tgt gcc cgt ggc ggt cgt gac ttc      720
Ala Ser Asp Thr Ala Met Tyr Tyr Cys Ala Arg Gly Gly Arg Asp Phe
225                 230                 235                 240 ggt gat agc ttc gat tac tgg ggt cag ggc acc ctg gtg acc gtg agc      768
Gly Asp Ser Phe Asp Tyr Trp Gly Gln Gly Thr Leu Val Thr Val Ser
                245                 250                 255 agc taa taa                                                          777
Ser

<210> SEQ ID NO 44
<211> LENGTH: 257
<212> TYPE: PRT
<213> ORGANISM: Artificial
<220> FEATURE:
<223> OTHER INFORMATION: Synthetic Construct

<400> SEQUENCE: 44

Met Asp Val Val Met Thr Gln Ser Pro Ser Phe Leu Ser Ala Phe Val
1               5                   10                  15

Gly Asp Arg Ile Thr Ile Thr Cys Arg Ala Ser Ser Gly Ile Ser Arg
            20                  25                  30

Tyr Leu Ala Trp Tyr Gln Gln Ala Pro Gly Lys Ala Pro Lys Leu Leu
        35                  40                  45

Ile Tyr Ala Ala Ser Thr Leu Gln Thr Gly Val Pro Ser Arg Phe Ser
    50                  55                  60

Gly Ser Gly Ser Gly Thr Glu Phe Thr Leu Thr Ile Asn Ser Leu Gln
65                  70                  75                  80

Pro Glu Asp Phe Ala Thr Tyr Tyr Cys Gln His Leu Asn Ser Tyr Pro
                85                  90                  95

Leu Thr Phe Gly Gly Gly Thr Lys Val Asp Ile Lys Arg Ala Ser Gly
            100                 105                 110

Gly Gly Gly Ser Gly Gly Gly Gly Ser Gly Gly Gly Ser Gly Gly
            115                 120                 125

Gly Gly Ser Gly Gly Gly Ser Ala Glu Val Gln Leu Val Glu Ser
        130                 135                 140

Gly Ala Glu Val Lys Lys Pro Gly Glu Ser Leu Arg Ile Ser Cys Lys
145                 150                 155                 160

Gly Ser Gly Cys Ile Ile Ser Ser Tyr Trp Ile Ser Trp Val Arg Gln
                165                 170                 175

Met Pro Gly Lys Gly Leu Glu Trp Met Gly Lys Ile Asp Pro Gly Asp
            180                 185                 190

Ser Tyr Ile Asn Tyr Ser Pro Ser Phe Gln Gly His Val Thr Ile Ser
        195                 200                 205

Ala Asp Lys Ser Ile Asn Thr Ala Tyr Leu Gln Trp Asn Ser Leu Lys
    210                 215                 220
```

Ala Ser Asp Thr Ala Met Tyr Tyr Cys Ala Arg Gly Gly Arg Asp Phe
225                 230                 235                 240

Gly Asp Ser Phe Asp Tyr Trp Gly Gln Gly Thr Leu Val Thr Val Ser
            245                 250                 255

Ser

<210> SEQ ID NO 45
<211> LENGTH: 792
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(792)

<400> SEQUENCE: 45

| atg gat gtt gtg atg acc cag agc ccg agc ttc ctg agc gcg ttc gtt | 48 |
|---|---|
| Met Asp Val Val Met Thr Gln Ser Pro Ser Phe Leu Ser Ala Phe Val | |
| 1               5                   10                  15 | |

| ggt gac cgt atc acc att acc tgc cgc gcc agc agc ggc atc agc cgc | 96 |
|---|---|
| Gly Asp Arg Ile Thr Ile Thr Cys Arg Ala Ser Ser Gly Ile Ser Arg | |
|             20                  25                  30 | |

| tat ctg gcg tgg tat cag caa gca ccg ggt aaa gca ccg aaa ctg ctg | 144 |
|---|---|
| Tyr Leu Ala Trp Tyr Gln Gln Ala Pro Gly Lys Ala Pro Lys Leu Leu | |
|         35                  40                  45 | |

| atc tat gct gca agc acc ctg caa acc ggc gtt ccg agc cgt ttt agc | 192 |
|---|---|
| Ile Tyr Ala Ala Ser Thr Leu Gln Thr Gly Val Pro Ser Arg Phe Ser | |
|     50                  55                  60 | |

| ggt agc ggc agc ggc acc gag ttc acc ctg acc atc aac agc ctg caa | 240 |
|---|---|
| Gly Ser Gly Ser Gly Thr Glu Phe Thr Leu Thr Ile Asn Ser Leu Gln | |
| 65                  70                  75                  80 | |

| ccg gag gat ttt gcc acc tat tac tgc caa cac ctg aat agc tat ccg | 288 |
|---|---|
| Pro Glu Asp Phe Ala Thr Tyr Tyr Cys Gln His Leu Asn Ser Tyr Pro | |
|                 85                  90                  95 | |

| ctg acc ttc ggt ggc ggc acc aaa gtg gac atc aaa cgc gcg agc ggt | 336 |
|---|---|
| Leu Thr Phe Gly Gly Gly Thr Lys Val Asp Ile Lys Arg Ala Ser Gly | |
|             100                 105                 110 | |

| ggt ggc ggc agc ggt ggt ggc gga tct ggt ggt ggc ggc agc ggt ggt | 384 |
|---|---|
| Gly Gly Gly Ser Gly Gly Gly Gly Ser Gly Gly Gly Gly Ser Gly Gly | |
|         115                 120                 125 | |

| ggc gga tcc ggt ggt ggc ggc agc ggc ggc ggc agc gct gaa gtt | 432 |
|---|---|
| Gly Gly Ser Gly Gly Gly Gly Ser Gly Gly Gly Gly Ser Ala Glu Val | |
|     130                 135                 140 | |

| caa ctt gtt gaa tct ggt gct gaa gtt aaa aaa ccg ggt gaa tct ctg | 480 |
|---|---|
| Gln Leu Val Glu Ser Gly Ala Glu Val Lys Lys Pro Gly Glu Ser Leu | |
| 145                 150                 155                 160 | |

| cgt atc tct tgc aaa ggt tct ggt tgc atc atc tct tct tac tgg atc | 528 |
|---|---|
| Arg Ile Ser Cys Lys Gly Ser Gly Cys Ile Ile Ser Ser Tyr Trp Ile | |
|                 165                 170                 175 | |

| agc tgg gtt cgt cag atg ccg ggc aag ggc ctg gaa tgg atg ggt aaa | 576 |
|---|---|
| Ser Trp Val Arg Gln Met Pro Gly Lys Gly Leu Glu Trp Met Gly Lys | |
|             180                 185                 190 | |

| att gat ccg ggc gac agc tat att aac tac agc ccg agc ttt cag ggc | 624 |
|---|---|
| Ile Asp Pro Gly Asp Ser Tyr Ile Asn Tyr Ser Pro Ser Phe Gln Gly | |
|         195                 200                 205 | |

| cat gtt acc atc agc gcc gat aaa agc att aac acc gct tac ctg caa | 672 |
|---|---|
| His Val Thr Ile Ser Ala Asp Lys Ser Ile Asn Thr Ala Tyr Leu Gln | |
|     210                 215                 220 | |

| tgg aac agc ctg aaa gcg agc gac acc gcg atg tac tac tgt gcc cgt | 720 |
|---|---|
| Trp Asn Ser Leu Lys Ala Ser Asp Thr Ala Met Tyr Tyr Cys Ala Arg | |

```
                225                 230                 235                 240
ggc ggt cgt gac ttc ggt gat agc ttc gat tac tgg ggt cag ggc acc       768
Gly Gly Arg Asp Phe Gly Asp Ser Phe Asp Tyr Trp Gly Gln Gly Thr
                245                 250                 255 ctg gtg acc gtg agc agc taa taa                                       792
Leu Val Thr Val Ser Ser
            260

<210> SEQ ID NO 46
<211> LENGTH: 262
<212> TYPE: PRT
<213> ORGANISM: Artificial
<220> FEATURE:
<223> OTHER INFORMATION: Synthetic Construct

<400> SEQUENCE: 46

Met Asp Val Val Met Thr Gln Ser Pro Ser Phe Leu Ser Ala Phe Val
1               5                   10                  15

Gly Asp Arg Ile Thr Ile Thr Cys Arg Ala Ser Ser Gly Ile Ser Arg
            20                  25                  30

Tyr Leu Ala Trp Tyr Gln Gln Ala Pro Gly Lys Ala Pro Lys Leu Leu
        35                  40                  45

Ile Tyr Ala Ala Ser Thr Leu Gln Thr Gly Val Pro Ser Arg Phe Ser
    50                  55                  60

Gly Ser Gly Ser Gly Thr Glu Phe Thr Leu Thr Ile Asn Ser Leu Gln
65                  70                  75                  80

Pro Glu Asp Phe Ala Thr Tyr Tyr Cys Gln His Leu Asn Ser Tyr Pro
                85                  90                  95

Leu Thr Phe Gly Gly Gly Thr Lys Val Asp Ile Lys Arg Ala Ser Gly
            100                 105                 110

Gly Gly Gly Ser Gly Gly Gly Ser Gly Gly Gly Ser Gly Gly
            115                 120                 125

Gly Gly Ser Gly Gly Gly Ser Gly Gly Gly Ser Ala Glu Val
            130                 135                 140

Gln Leu Val Glu Ser Gly Ala Glu Val Lys Lys Pro Gly Glu Ser Leu
145                 150                 155                 160

Arg Ile Ser Cys Lys Gly Ser Gly Cys Ile Ile Ser Ser Tyr Trp Ile
                165                 170                 175

Ser Trp Val Arg Gln Met Pro Gly Lys Gly Leu Glu Trp Met Gly Lys
            180                 185                 190

Ile Asp Pro Gly Asp Ser Tyr Ile Asn Tyr Ser Pro Ser Phe Gln Gly
        195                 200                 205

His Val Thr Ile Ser Ala Asp Lys Ser Ile Asn Thr Ala Tyr Leu Gln
    210                 215                 220

Trp Asn Ser Leu Lys Ala Ser Asp Thr Ala Met Tyr Tyr Cys Ala Arg
225                 230                 235                 240

Gly Gly Arg Asp Phe Gly Asp Ser Phe Asp Tyr Trp Gly Gln Gly Thr
                245                 250                 255

Leu Val Thr Val Ser Ser
            260

<210> SEQ ID NO 47
<211> LENGTH: 759
<212> TYPE: DNA
<213> ORGANISM: Artificial
<220> FEATURE:
<223> OTHER INFORMATION: Polynucleotide encoding scFv polypeptide
<220> FEATURE:
```

<221> NAME/KEY: CDS
<222> LOCATION: (1)..(759)

<400> SEQUENCE: 47

| | | | | | | | | | | | | | | | | |
|---|---|---|---|---|---|---|---|---|---|---|---|---|---|---|---|---|
| atg | gct | gaa | gtt | caa | ctt | gtt | gaa | tct | ggt | gct | gaa | gtt | aaa | aaa | ccg | 48 |
| Met | Ala | Glu | Val | Gln | Leu | Val | Glu | Ser | Gly | Ala | Glu | Val | Lys | Lys | Pro | |
| 1 | | | | 5 | | | | | 10 | | | | | 15 | | |
| ggt | gaa | tct | ctg | cgt | atc | tct | tgc | aaa | ggt | tct | ggt | tat | agc | atc | tct | 96 |
| Gly | Glu | Ser | Leu | Arg | Ile | Ser | Cys | Lys | Gly | Ser | Gly | Tyr | Ser | Ile | Ser | |
| | | | 20 | | | | | 25 | | | | | 30 | | | |
| tct | tac | tgg | atc | agc | tgg | gtt | cgt | cag | atg | ccg | ggc | aag | ggc | ctg | gaa | 144 |
| Ser | Tyr | Trp | Ile | Ser | Trp | Val | Arg | Gln | Met | Pro | Gly | Lys | Gly | Leu | Glu | |
| | | | 35 | | | | | 40 | | | | | 45 | | | |
| tgg | atg | ggt | aaa | att | gat | ccg | ggc | gac | agc | tat | att | aac | tac | agc | ccg | 192 |
| Trp | Met | Gly | Lys | Ile | Asp | Pro | Gly | Asp | Ser | Tyr | Ile | Asn | Tyr | Ser | Pro | |
| 50 | | | | | 55 | | | | | 60 | | | | | | |
| agc | ttt | cag | ggc | cat | gtt | acc | atc | agc | gcc | gat | aaa | agc | att | aac | acc | 240 |
| Ser | Phe | Gln | Gly | His | Val | Thr | Ile | Ser | Ala | Asp | Lys | Ser | Ile | Asn | Thr | |
| 65 | | | | 70 | | | | | 75 | | | | | 80 | | |
| gct | tac | ctg | caa | tgg | aac | agc | ctg | aaa | gcg | agc | gac | acc | gcg | atg | tac | 288 |
| Ala | Tyr | Leu | Gln | Trp | Asn | Ser | Leu | Lys | Ala | Ser | Asp | Thr | Ala | Met | Tyr | |
| | | | | 85 | | | | | 90 | | | | | 95 | | |
| tac | tgt | gcc | cgt | ggc | ggt | cgt | gac | ttc | ggt | gat | agc | ttc | gat | tac | tgg | 336 |
| Tyr | Cys | Ala | Arg | Gly | Gly | Arg | Asp | Phe | Gly | Asp | Ser | Phe | Asp | Tyr | Trp | |
| | | | 100 | | | | | 105 | | | | | 110 | | | |
| ggt | cag | ggc | acc | ctg | gtg | acc | gtg | agc | agc | ggt | ggt | ggc | ggc | agc | ggt | 384 |
| Gly | Gln | Gly | Thr | Leu | Val | Thr | Val | Ser | Ser | Gly | Gly | Gly | Gly | Ser | Gly | |
| | | | 115 | | | | | 120 | | | | | 125 | | | |
| ggt | ggc | gga | tcc | ggt | ggt | ggc | ggc | agc | ggc | ggc | ggc | agc | gat | gtt | | 432 |
| Gly | Gly | Gly | Ser | Gly | Gly | Gly | Gly | Ser | Gly | Gly | Gly | Ser | Asp | Val | | |
| | 130 | | | | | 135 | | | | | 140 | | | | | |
| gtg | atg | acc | cag | agc | ccg | agc | ttc | ctg | agc | gcg | ttc | gtt | ggt | gac | cgt | 480 |
| Val | Met | Thr | Gln | Ser | Pro | Ser | Phe | Leu | Ser | Ala | Phe | Val | Gly | Asp | Arg | |
| 145 | | | | | 150 | | | | | 155 | | | | | 160 | |
| atc | acc | att | acc | tgc | cgc | gcc | agc | agc | ggc | atc | agc | cgc | tat | ctg | gcg | 528 |
| Ile | Thr | Ile | Thr | Cys | Arg | Ala | Ser | Ser | Gly | Ile | Ser | Arg | Tyr | Leu | Ala | |
| | | | | 165 | | | | | 170 | | | | | 175 | | |
| tgg | tat | cag | caa | gca | ccg | ggt | aaa | gca | ccg | aaa | ctg | ctg | atc | tat | gct | 576 |
| Trp | Tyr | Gln | Gln | Ala | Pro | Gly | Lys | Ala | Pro | Lys | Leu | Leu | Ile | Tyr | Ala | |
| | | | 180 | | | | | 185 | | | | | 190 | | | |
| gca | agc | acc | ctg | caa | acc | ggc | gtt | ccg | agc | cgt | ttt | agc | ggt | agc | ggc | 624 |
| Ala | Ser | Thr | Leu | Gln | Thr | Gly | Val | Pro | Ser | Arg | Phe | Ser | Gly | Ser | Gly | |
| | | | 195 | | | | | 200 | | | | | 205 | | | |
| agc | ggc | acc | gag | ttc | acc | ctg | acc | atc | aac | agc | ctg | caa | ccg | gag | gat | 672 |
| Ser | Gly | Thr | Glu | Phe | Thr | Leu | Thr | Ile | Asn | Ser | Leu | Gln | Pro | Glu | Asp | |
| | 210 | | | | | 215 | | | | | 220 | | | | | |
| ttt | gcc | acc | tat | tac | tgc | caa | cac | ctg | aat | agc | tat | ccg | ctg | acc | ttc | 720 |
| Phe | Ala | Thr | Tyr | Tyr | Cys | Gln | His | Leu | Asn | Ser | Tyr | Pro | Leu | Thr | Phe | |
| 225 | | | | | 230 | | | | | 235 | | | | | 240 | |
| ggt | ggc | ggc | acc | aaa | gtg | gac | atc | aaa | cgc | gcg | taa | taa | | | | 759 |
| Gly | Gly | Gly | Thr | Lys | Val | Asp | Ile | Lys | Arg | Ala | | | | | | |
| | | | | 245 | | | | | 250 | | | | | | | |

<210> SEQ ID NO 48
<211> LENGTH: 251
<212> TYPE: PRT
<213> ORGANISM: Artificial
<220> FEATURE:
<223> OTHER INFORMATION: Synthetic Construct

<400> SEQUENCE: 48

```
Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Tyr Ser Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Gly Gly Gly Gly Ser Asp Val
    130                 135                 140

Val Met Thr Gln Ser Pro Ser Phe Leu Ser Ala Phe Val Gly Asp Arg
145                 150                 155                 160

Ile Thr Ile Thr Cys Arg Ala Ser Ser Gly Ile Ser Arg Tyr Leu Ala
                165                 170                 175

Trp Tyr Gln Gln Ala Pro Gly Lys Ala Pro Lys Leu Leu Ile Tyr Ala
            180                 185                 190

Ala Ser Thr Leu Gln Thr Gly Val Pro Ser Arg Phe Ser Gly Ser Gly
        195                 200                 205

Ser Gly Thr Glu Phe Thr Leu Thr Ile Asn Ser Leu Gln Pro Glu Asp
    210                 215                 220

Phe Ala Thr Tyr Tyr Cys Gln His Leu Asn Ser Tyr Pro Leu Thr Phe
225                 230                 235                 240

Gly Gly Gly Thr Lys Val Asp Ile Lys Arg Ala
                245                 250
```

<210> SEQ ID NO 49
<211> LENGTH: 774
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(774)

<400> SEQUENCE: 49

```
atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt tat agc atc tct      96
Gly Glu Ser Leu Arg Ile Ser Cys Lys Gly Ser Gly Tyr Ser Ile Ser
            20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
    50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
```

```
                                65                      70                      75                      80
gct tac ctg caa tgg aac agc ctg aaa gcg agc gac acc gcg atg tac          288
Ala Tyr Leu Gln Trp Asn Ser Leu Lys Ala Ser Asp Thr Ala Met Tyr
                        85                      90                      95 tac tgt gcc cgt ggc ggt cgt gac ttc ggt gat agc ttc gat tac tgg          336
Tyr Cys Ala Arg Gly Gly Arg Asp Phe Gly Asp Ser Phe Asp Tyr Trp
                100                     105                     110 ggt cag ggc acc ctg gtg acc gtg agc agc ggt ggt ggc ggc agc ggt          384
Gly Gln Gly Thr Leu Val Thr Val Ser Ser Gly Gly Gly Gly Ser Gly
        115                     120                     125 ggt gga tcc ggt ggt ggc ggc tcc ggt ggt ggc ggc agc ggc ggc              432
Gly Gly Ser Gly Gly Gly Gly Ser Gly Gly Gly Gly Ser Gly Gly
130                     135                     140 ggc agc gat gtt gtg atg acc cag agc ccg agc ttc ctg agc gcg              480
Gly Ser Asp Val Val Met Thr Gln Ser Pro Ser Phe Leu Ser Ala
145                     150                     155                     160 ttc gtt ggt gac cgt atc acc att acc tgc cgc gcc agc agc ggc atc          528
Phe Val Gly Asp Arg Ile Thr Ile Thr Cys Arg Ala Ser Ser Gly Ile
                165                     170                     175 agc cgc tat ctg gcg tgg tat cag caa gca ccg ggt aaa gca ccg aaa          576
Ser Arg Tyr Leu Ala Trp Tyr Gln Gln Ala Pro Gly Lys Ala Pro Lys
                180                     185                     190 ctg ctg atc tat gct gca agc acc ctg caa acc ggc gtt ccg agc cgt          624
Leu Leu Ile Tyr Ala Ala Ser Thr Leu Gln Thr Gly Val Pro Ser Arg
                195                     200                     205 ttt agc ggt agc ggc agc ggc acc gag ttc acc ctg acc atc aac agc          672
Phe Ser Gly Ser Gly Ser Gly Thr Glu Phe Thr Leu Thr Ile Asn Ser
        210                     215                     220 ctg caa ccg gag gat ttt gcc acc tat tac tgc caa cac ctg aat agc          720
Leu Gln Pro Glu Asp Phe Ala Thr Tyr Tyr Cys Gln His Leu Asn Ser
225                     230                     235                     240 tat ccg ctg acc ttc ggt ggc ggc acc aaa gtg gac atc aaa cgc gcg          768
Tyr Pro Leu Thr Phe Gly Gly Gly Thr Lys Val Asp Ile Lys Arg Ala
                245                     250                     255 taa taa                                                                  774
```

<210> SEQ ID NO 50
<211> LENGTH: 256
<212> TYPE: PRT
<213> ORGANISM: Artificial
<220> FEATURE:
<223> OTHER INFORMATION: Synthetic Construct

<400> SEQUENCE: 50

```
Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Tyr Ser Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110
```

```
Gly Gln Gly Thr Leu Val Thr Val Ser Ser Gly Gly Gly Ser Gly
        115                 120                 125

Gly Gly Gly Ser Gly Gly Gly Ser Gly Gly Gly Ser Gly Gly
130                 135                 140

Gly Gly Ser Asp Val Val Met Thr Gln Ser Pro Ser Phe Leu Ser Ala
145                 150                 155                 160

Phe Val Gly Asp Arg Ile Thr Ile Thr Cys Arg Ala Ser Ser Gly Ile
                165                 170                 175

Ser Arg Tyr Leu Ala Trp Tyr Gln Gln Ala Pro Gly Lys Ala Pro Lys
            180                 185                 190

Leu Leu Ile Tyr Ala Ala Ser Thr Leu Gln Thr Gly Val Pro Ser Arg
        195                 200                 205

Phe Ser Gly Ser Gly Ser Gly Thr Glu Phe Thr Leu Thr Ile Asn Ser
    210                 215                 220

Leu Gln Pro Glu Asp Phe Ala Thr Tyr Tyr Cys Gln His Leu Asn Ser
225                 230                 235                 240

Tyr Pro Leu Thr Phe Gly Gly Thr Lys Val Asp Ile Lys Arg Ala
                245                 250                 255

<210> SEQ ID NO 51
<211> LENGTH: 789
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(789)

<400> SEQUENCE: 51 atg gct gaa gtt caa ctt gtt gaa tct ggt gct gaa gtt aaa aaa ccg      48
Met Ala Glu Val Gln Leu Val Glu Ser Gly Ala Glu Val Lys Lys Pro
1               5                   10                  15 ggt gaa tct ctg cgt atc tct tgc aaa ggt tct ggt tat agc atc tct      96
Gly Glu Ser Leu Arg Ile Ser Cys Lys Gly Ser Gly Tyr Ser Ile Ser
            20                  25                  30 tct tac tgg atc agc tgg gtt cgt cag atg ccg ggc aag ggc ctg gaa     144
Ser Tyr Trp Ile Ser Trp Val Arg Gln Met Pro Gly Lys Gly Leu Glu
        35                  40                  45 tgg atg ggt aaa att gat ccg ggc gac agc tat att aac tac agc ccg     192
Trp Met Gly Lys Ile Asp Pro Gly Asp Ser Tyr Ile Asn Tyr Ser Pro
    50                  55                  60 agc ttt cag ggc cat gtt acc atc agc gcc gat aaa agc att aac acc     240
Ser Phe Gln Gly His Val Thr Ile Ser Ala Asp Lys Ser Ile Asn Thr
65                  70                  75                  80 gct tac ctg caa tgg aac agc ctg aaa gcg agc gac acc gcg atg tac     288
Ala Tyr Leu Gln Trp Asn Ser Leu Lys Ala Ser Asp Thr Ala Met Tyr
                85                  90                  95 tac tgt gcc cgt ggc ggt cgt gac ttc ggt gat agc ttc gat tac tgg     336
Tyr Cys Ala Arg Gly Gly Arg Asp Phe Gly Asp Ser Phe Asp Tyr Trp
            100                 105                 110 ggt cag ggc acc ctg gtg acc gtg agc agc ggt ggt ggc ggc agc ggt     384
Gly Gln Gly Thr Leu Val Thr Val Ser Ser Gly Gly Gly Gly Ser Gly
        115                 120                 125 ggt ggc gga tct ggt ggt ggc ggc agc ggt ggt ggc gga tcc ggt ggt     432
Gly Gly Gly Ser Gly Gly Gly Gly Ser Gly Gly Gly Gly Ser Gly Gly
    130                 135                 140 ggc ggc agc ggc ggc ggc ggc agc gat gtt gtg atg acc cag agc ccg     480
Gly Gly Ser Gly Gly Gly Gly Ser Asp Val Val Met Thr Gln Ser Pro
145                 150                 155                 160
```

-continued

```
agc ttc ctg agc gcg ttc gtt ggt gac cgt atc acc att acc tgc cgc      528
Ser Phe Leu Ser Ala Phe Val Gly Asp Arg Ile Thr Ile Thr Cys Arg
            165                 170                 175 gcc agc agc ggc atc agc cgc tat ctg gcg tgg tat cag caa gca ccg      576
Ala Ser Ser Gly Ile Ser Arg Tyr Leu Ala Trp Tyr Gln Gln Ala Pro
        180                 185                 190 ggt aaa gca ccg aaa ctg ctg atc tat gct gca agc acc ctg caa acc      624
Gly Lys Ala Pro Lys Leu Leu Ile Tyr Ala Ala Ser Thr Leu Gln Thr
    195                 200                 205 ggc gtt ccg agc cgt ttt agc ggt agc ggc agc ggc acc gag ttc acc      672
Gly Val Pro Ser Arg Phe Ser Gly Ser Gly Ser Gly Thr Glu Phe Thr
210                 215                 220 ctg acc atc aac agc ctg caa ccg gag gat ttt gcc acc tat tac tgc      720
Leu Thr Ile Asn Ser Leu Gln Pro Glu Asp Phe Ala Thr Tyr Tyr Cys
225                 230                 235                 240 caa cac ctg aat agc tat ccg ctg acc ttc ggt ggc ggc acc aaa gtg      768
Gln His Leu Asn Ser Tyr Pro Leu Thr Phe Gly Gly Gly Thr Lys Val
                245                 250                 255 gac atc aaa cgc gcg taa taa                                          789
Asp Ile Lys Arg Ala
            260

<210> SEQ ID NO 52
<211> LENGTH: 261
<212> TYPE: PRT
<213> ORGANISM: Artificial
<220> FEATURE:
<223> OTHER INFORMATION: Synthetic Construct

<400> SEQUENCE: 52

Met Ala Glu Val Gln Leu Val Glu Ser Gly Ala Glu Val Lys Lys Pro
1               5                   10                  15

Gly Glu Ser Leu Arg Ile Ser Cys Lys Gly Ser Gly Tyr Ser Ile Ser
            20                  25                  30

Ser Tyr Trp Ile Ser Trp Val Arg Gln Met Pro Gly Lys Gly Leu Glu
        35                  40                  45

Trp Met Gly Lys Ile Asp Pro Gly Asp Ser Tyr Ile Asn Tyr Ser Pro
    50                  55                  60

Ser Phe Gln Gly His Val Thr Ile Ser Ala Asp Lys Ser Ile Asn Thr
65                  70                  75                  80

Ala Tyr Leu Gln Trp Asn Ser Leu Lys Ala Ser Asp Thr Ala Met Tyr
                85                  90                  95

Tyr Cys Ala Arg Gly Gly Arg Asp Phe Gly Asp Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Gly Gly Gly Gly Ser Gly Gly
    130                 135                 140

Gly Gly Ser Gly Gly Gly Ser Asp Val Val Met Thr Gln Ser Pro
145                 150                 155                 160

Ser Phe Leu Ser Ala Phe Val Gly Asp Arg Ile Thr Ile Thr Cys Arg
                165                 170                 175

Ala Ser Ser Gly Ile Ser Arg Tyr Leu Ala Trp Tyr Gln Gln Ala Pro
            180                 185                 190

Gly Lys Ala Pro Lys Leu Leu Ile Tyr Ala Ala Ser Thr Leu Gln Thr
        195                 200                 205

Gly Val Pro Ser Arg Phe Ser Gly Ser Gly Ser Gly Thr Glu Phe Thr
```

```
                210                 215                 220
Leu Thr Ile Asn Ser Leu Gln Pro Glu Asp Phe Ala Thr Tyr Tyr Cys
225                 230                 235                 240

Gln His Leu Asn Ser Tyr Pro Leu Thr Phe Gly Gly Gly Thr Lys Val
                245                 250                 255

Asp Ile Lys Arg Ala
            260

<210> SEQ ID NO 53
<211> LENGTH: 762
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(762)

<400> SEQUENCE: 53 atg gat gtt gtg atg acc cag agc ccg agc ttc ctg agc gcg ttc gtt       48
Met Asp Val Val Met Thr Gln Ser Pro Ser Phe Leu Ser Ala Phe Val
1               5                   10                  15 ggt gac cgt atc acc att acc tgc cgc gcc agc agc ggc atc agc cgc       96
Gly Asp Arg Ile Thr Ile Thr Cys Arg Ala Ser Ser Gly Ile Ser Arg
            20                  25                  30 tat ctg gcg tgg tat cag caa gca ccg ggt aaa gca ccg aaa ctg ctg      144
Tyr Leu Ala Trp Tyr Gln Gln Ala Pro Gly Lys Ala Pro Lys Leu Leu
        35                  40                  45 atc tat gct gca agc acc ctg caa acc ggc gtt ccg agc cgt ttt agc      192
Ile Tyr Ala Ala Ser Thr Leu Gln Thr Gly Val Pro Ser Arg Phe Ser
    50                  55                  60 ggt agc ggc agc ggc acc gag ttc acc ctg acc atc aac agc ctg caa      240
Gly Ser Gly Ser Gly Thr Glu Phe Thr Leu Thr Ile Asn Ser Leu Gln
65                  70                  75                  80 ccg gag gat ttt gcc acc tat tac tgc caa cac ctg aat agc tat ccg      288
Pro Glu Asp Phe Ala Thr Tyr Tyr Cys Gln His Leu Asn Ser Tyr Pro
                85                  90                  95 ctg acc ttc ggt ggc ggc acc aaa gtg gac atc aaa cgc gcg agc ggt      336
Leu Thr Phe Gly Gly Gly Thr Lys Val Asp Ile Lys Arg Ala Ser Gly
            100                 105                 110 ggt ggc ggc agc ggt ggc ggc gga tcc ggt ggc ggc ggc agc ggc ggc      384
Gly Gly Gly Ser Gly Gly Gly Gly Ser Gly Gly Gly Gly Ser Gly Gly
        115                 120                 125 ggc ggc agc gct gaa gtt caa ctt gtt gaa tct ggt gct gaa gtt aaa      432
Gly Gly Ser Ala Glu Val Gln Leu Val Glu Ser Gly Ala Glu Val Lys
    130                 135                 140 aaa ccg ggt gaa tct ctg cgt atc tct tgc aaa ggt tct ggt tat agc      480
Lys Pro Gly Glu Ser Leu Arg Ile Ser Cys Lys Gly Ser Gly Tyr Ser
145                 150                 155                 160 atc tct tct tac tgg atc agc tgg gtt cgt cag atg ccg ggc aag ggc      528
Ile Ser Ser Tyr Trp Ile Ser Trp Val Arg Gln Met Pro Gly Lys Gly
                165                 170                 175 ctg gaa tgg atg ggt aaa att gat ccg ggc gac agc tat att aac tac      576
Leu Glu Trp Met Gly Lys Ile Asp Pro Gly Asp Ser Tyr Ile Asn Tyr
            180                 185                 190 agc ccg agc ttt cag ggc cat gtt acc atc agc gcc gat aaa agc att      624
Ser Pro Ser Phe Gln Gly His Val Thr Ile Ser Ala Asp Lys Ser Ile
        195                 200                 205 aac acc gct tac ctg caa tgg aac agc ctg aaa gcg agc gac acc gcg      672
Asn Thr Ala Tyr Leu Gln Trp Asn Ser Leu Lys Ala Ser Asp Thr Ala
    210                 215                 220
```

```
atg tac tac tgt gcc cgt ggc ggt cgt gac ttc ggt gat agc ttc gat    720
Met Tyr Tyr Cys Ala Arg Gly Gly Arg Asp Phe Gly Asp Ser Phe Asp
225                 230                 235                 240 tac tgg ggt cag ggc acc ctg gtg acc gtg agc agc taa taa            762
Tyr Trp Gly Gln Gly Thr Leu Val Thr Val Ser Ser
                245                 250

<210> SEQ ID NO 54
<211> LENGTH: 252
<212> TYPE: PRT
<213> ORGANISM: Artificial
<220> FEATURE:
<223> OTHER INFORMATION: Synthetic Construct

<400> SEQUENCE: 54

Met Asp Val Val Met Thr Gln Ser Pro Ser Phe Leu Ser Ala Phe Val
1               5                   10                  15

Gly Asp Arg Ile Thr Ile Thr Cys Arg Ala Ser Ser Gly Ile Ser Arg
            20                  25                  30

Tyr Leu Ala Trp Tyr Gln Gln Ala Pro Gly Lys Ala Pro Lys Leu Leu
        35                  40                  45

Ile Tyr Ala Ala Ser Thr Leu Gln Thr Gly Val Pro Ser Arg Phe Ser
    50                  55                  60

Gly Ser Gly Ser Gly Thr Glu Phe Thr Leu Thr Ile Asn Ser Leu Gln
65                  70                  75                  80

Pro Glu Asp Phe Ala Thr Tyr Tyr Cys Gln His Leu Asn Ser Tyr Pro
                85                  90                  95

Leu Thr Phe Gly Gly Gly Thr Lys Val Asp Ile Lys Arg Ala Ser Gly
            100                 105                 110

Gly Gly Gly Ser Gly Gly Gly Ser Gly Gly Gly Ser Gly Gly
        115                 120                 125

Gly Gly Ser Ala Glu Val Gln Leu Val Glu Ser Gly Ala Glu Val Lys
    130                 135                 140

Lys Pro Gly Glu Ser Leu Arg Ile Ser Cys Lys Gly Ser Gly Tyr Ser
145                 150                 155                 160

Ile Ser Ser Tyr Trp Ile Ser Trp Val Arg Gln Met Pro Gly Lys Gly
                165                 170                 175

Leu Glu Trp Met Gly Lys Ile Asp Pro Gly Asp Ser Tyr Ile Asn Tyr
            180                 185                 190

Ser Pro Ser Phe Gln Gly His Val Thr Ile Ser Ala Asp Lys Ser Ile
        195                 200                 205

Asn Thr Ala Tyr Leu Gln Trp Asn Ser Leu Lys Ala Ser Asp Thr Ala
    210                 215                 220

Met Tyr Tyr Cys Ala Arg Gly Gly Arg Asp Phe Gly Asp Ser Phe Asp
225                 230                 235                 240

Tyr Trp Gly Gln Gly Thr Leu Val Thr Val Ser Ser
                245                 250

<210> SEQ ID NO 55
<211> LENGTH: 777
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(777)

<400> SEQUENCE: 55
```

```
atg gat gtt gtg atg acc cag agc ccg agc ttc ctg agc gcg ttc gtt    48
Met Asp Val Val Met Thr Gln Ser Pro Ser Phe Leu Ser Ala Phe Val
1               5                   10                  15 ggt gac cgt atc acc att acc tgc cgc gcc agc agc ggc atc agc cgc    96
Gly Asp Arg Ile Thr Ile Thr Cys Arg Ala Ser Ser Gly Ile Ser Arg
            20                  25                  30 tat ctg gcg tgg tat cag caa gca ccg ggt aaa gca ccg aaa ctg ctg   144
Tyr Leu Ala Trp Tyr Gln Gln Ala Pro Gly Lys Ala Pro Lys Leu Leu
        35                  40                  45 atc tat gct gca agc acc ctg caa acc ggc gtt ccg agc cgt ttt agc   192
Ile Tyr Ala Ala Ser Thr Leu Gln Thr Gly Val Pro Ser Arg Phe Ser
    50                  55                  60 ggt agc ggc agc ggc acc gag ttc acc ctg acc atc aac agc ctg caa   240
Gly Ser Gly Ser Gly Thr Glu Phe Thr Leu Thr Ile Asn Ser Leu Gln
65                  70                  75                  80 ccg gag gat ttt gcc acc tat tac tgc caa cac ctg aat agc tat ccg   288
Pro Glu Asp Phe Ala Thr Tyr Tyr Cys Gln His Leu Asn Ser Tyr Pro
                85                  90                  95 ctg acc ttc ggt ggc ggc acc aaa gtg gac atc aaa cgc gcg agc ggt   336
Leu Thr Phe Gly Gly Gly Thr Lys Val Asp Ile Lys Arg Ala Ser Gly
            100                 105                 110 ggt ggc ggc agc ggt ggt ggc gga tcc ggt ggt ggc ggc tcc ggt ggt   384
Gly Gly Gly Ser Gly Gly Gly Gly Ser Gly Gly Gly Gly Ser Gly Gly
        115                 120                 125 ggc ggc agc ggc ggc ggc ggc agc gct gaa gtt caa ctt gtt gaa tct   432
Gly Gly Ser Gly Gly Gly Gly Ser Ala Glu Val Gln Leu Val Glu Ser
    130                 135                 140 ggt gct gaa gtt aaa aaa ccg ggt gaa tct ctg cgt atc tct tgc aaa   480
Gly Ala Glu Val Lys Lys Pro Gly Glu Ser Leu Arg Ile Ser Cys Lys
145                 150                 155                 160 ggt tct ggt tat agc atc tct tct tac tgg atc agc tgg gtt cgt cag   528
Gly Ser Gly Tyr Ser Ile Ser Ser Tyr Trp Ile Ser Trp Val Arg Gln
                165                 170                 175 atg ccg ggc aag ggc ctg gaa tgg atg ggt aaa att gat ccg ggc gac   576
Met Pro Gly Lys Gly Leu Glu Trp Met Gly Lys Ile Asp Pro Gly Asp
            180                 185                 190 agc tat att aac tac agc ccg agc ttt cag ggc cat gtt acc atc agc   624
Ser Tyr Ile Asn Tyr Ser Pro Ser Phe Gln Gly His Val Thr Ile Ser
        195                 200                 205 gcc gat aaa agc att aac acc gct tac ctg caa tgg aac agc ctg aaa   672
Ala Asp Lys Ser Ile Asn Thr Ala Tyr Leu Gln Trp Asn Ser Leu Lys
    210                 215                 220 gcg agc gac acc gcg atg tac tac tgt gcc cgt ggc ggt cgt gac ttc   720
Ala Ser Asp Thr Ala Met Tyr Tyr Cys Ala Arg Gly Gly Arg Asp Phe
225                 230                 235                 240 ggt gat agc ttc gat tac tgg ggt cag ggc acc ctg gtg acc gtg agc   768
Gly Asp Ser Phe Asp Tyr Trp Gly Gln Gly Thr Leu Val Thr Val Ser
                245                 250                 255 agc taa taa                                                       777
Ser
```

<210> SEQ ID NO 56
<211> LENGTH: 257
<212> TYPE: PRT
<213> ORGANISM: Artificial
<220> FEATURE:
<223> OTHER INFORMATION: Synthetic Construct

<400> SEQUENCE: 56

Met Asp Val Val Met Thr Gln Ser Pro Ser Phe Leu Ser Ala Phe Val

```
                1               5                  10                 15
Gly Asp Arg Ile Thr Ile Thr Cys Arg Ala Ser Ser Gly Ile Ser Arg
                20                      25                 30

Tyr Leu Ala Trp Tyr Gln Gln Ala Pro Gly Lys Ala Pro Lys Leu Leu
            35                      40                 45

Ile Tyr Ala Ala Ser Thr Leu Gln Thr Gly Val Pro Ser Arg Phe Ser
        50                      55                 60

Gly Ser Gly Ser Gly Thr Glu Phe Thr Leu Thr Ile Asn Ser Leu Gln
65                      70                  75                  80

Pro Glu Asp Phe Ala Thr Tyr Tyr Cys Gln His Leu Asn Ser Tyr Pro
                    85                      90                  95

Leu Thr Phe Gly Gly Gly Thr Lys Val Asp Ile Lys Arg Ala Ser Gly
                100                     105                110

Gly Gly Gly Ser Gly Gly Gly Ser Gly Gly Gly Ser Gly Gly
            115                     120                125

Gly Gly Ser Gly Gly Gly Ser Ala Glu Val Gln Leu Val Glu Ser
            130                     135                140

Gly Ala Glu Val Lys Lys Pro Gly Glu Ser Leu Arg Ile Ser Cys Lys
145                     150                     155                 160

Gly Ser Gly Tyr Ser Ile Ser Ser Tyr Trp Ile Ser Trp Val Arg Gln
                165                     170                 175

Met Pro Gly Lys Gly Leu Glu Trp Met Gly Lys Ile Asp Pro Gly Asp
                180                     185                 190

Ser Tyr Ile Asn Tyr Ser Pro Ser Phe Gln Gly His Val Thr Ile Ser
                195                     200                 205

Ala Asp Lys Ser Ile Asn Thr Ala Tyr Leu Gln Trp Asn Ser Leu Lys
210                     215                     220

Ala Ser Asp Thr Ala Met Tyr Tyr Cys Ala Arg Gly Gly Arg Asp Phe
225                     230                     235                 240

Gly Asp Ser Phe Asp Tyr Trp Gly Gln Gly Thr Leu Val Thr Val Ser
                245                     250                 255

Ser

<210> SEQ ID NO 57
<211> LENGTH: 792
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(792)

<400> SEQUENCE: 57 atg gat gtt gtg atg acc cag agc ccg agc ttc ctg agc gcg ttc gtt        48
Met Asp Val Val Met Thr Gln Ser Pro Ser Phe Leu Ser Ala Phe Val
1               5                   10                  15 ggt gac cgt atc acc att acc tgc cgc gcc agc agc ggc atc agc cgc        96
Gly Asp Arg Ile Thr Ile Thr Cys Arg Ala Ser Ser Gly Ile Ser Arg
                20                      25                  30 tat ctg gcg tgg tat cag caa gca ccg ggt aaa gca ccg aaa ctg ctg       144
Tyr Leu Ala Trp Tyr Gln Gln Ala Pro Gly Lys Ala Pro Lys Leu Leu
            35                      40                  45 atc tat gct gca agc acc ctg caa acc ggc gtt ccg agc cgt ttt agc       192
Ile Tyr Ala Ala Ser Thr Leu Gln Thr Gly Val Pro Ser Arg Phe Ser
        50                      55                  60 ggt agc ggc agc ggc acc gag ttc acc ctg acc atc aac agc ctg caa       240
```

```
Gly Ser Gly Ser Gly Thr Glu Phe Thr Leu Thr Ile Asn Ser Leu Gln
 65                  70                  75                  80 ccg gag gat ttt gcc acc tat tac tgc caa cac ctg aat agc tat ccg      288
Pro Glu Asp Phe Ala Thr Tyr Tyr Cys Gln His Leu Asn Ser Tyr Pro
                 85                  90                  95 ctg acc ttc ggt ggc ggc acc aaa gtg gac atc aaa cgc gcg agc ggt      336
Leu Thr Phe Gly Gly Gly Thr Lys Val Asp Ile Lys Arg Ala Ser Gly
            100                 105                 110 ggt ggc ggc agc ggt ggt ggc gga tct ggt ggt ggc agc ggt ggt          384
Gly Gly Gly Ser Gly Gly Gly Gly Ser Gly Gly Gly Ser Gly Gly
        115                 120                 125 ggc gga tcc ggt ggt ggc ggc agc ggc ggc ggc agc gct gaa gtt          432
Gly Gly Ser Gly Gly Gly Ser Gly Gly Gly Ser Ala Glu Val
    130                 135                 140 caa ctt gtt gaa tct ggt gct gaa gtt aaa aaa ccg ggt gaa tct ctg      480
Gln Leu Val Glu Ser Gly Ala Glu Val Lys Lys Pro Gly Glu Ser Leu
145                 150                 155                 160 cgt atc tct tgc aaa ggt tct ggt tat agc atc tct tct tac tgg atc      528
Arg Ile Ser Cys Lys Gly Ser Gly Tyr Ser Ile Ser Ser Tyr Trp Ile
                165                 170                 175 agc tgg gtt cgt cag atg ccg ggc aag ggc ctg gaa tgg atg ggt aaa      576
Ser Trp Val Arg Gln Met Pro Gly Lys Gly Leu Glu Trp Met Gly Lys
            180                 185                 190 att gat ccg ggc gac agc tat att aac tac agc ccg agc ttt cag ggc      624
Ile Asp Pro Gly Asp Ser Tyr Ile Asn Tyr Ser Pro Ser Phe Gln Gly
        195                 200                 205 cat gtt acc atc agc gcc gat aaa agc att aac acc gct tac ctg caa      672
His Val Thr Ile Ser Ala Asp Lys Ser Ile Asn Thr Ala Tyr Leu Gln
    210                 215                 220 tgg aac agc ctg aaa gcg agc gac acc gcg atg tac tac tgt gcc cgt      720
Trp Asn Ser Leu Lys Ala Ser Asp Thr Ala Met Tyr Tyr Cys Ala Arg
225                 230                 235                 240 ggc ggt cgt gac ttc ggt gat agc ttc gat tac tgg ggt cag ggc acc      768
Gly Gly Arg Asp Phe Gly Asp Ser Phe Asp Tyr Trp Gly Gln Gly Thr
                245                 250                 255 ctg gtg acc gtg agc agc taa taa                                      792
Leu Val Thr Val Ser Ser
            260

<210> SEQ ID NO 58
<211> LENGTH: 262
<212> TYPE: PRT
<213> ORGANISM: Artificial
<220> FEATURE:
<223> OTHER INFORMATION: Synthetic Construct

<400> SEQUENCE: 58

Met Asp Val Val Met Thr Gln Ser Pro Ser Phe Leu Ser Ala Phe Val
 1               5                  10                  15

Gly Asp Arg Ile Thr Ile Thr Cys Arg Ala Ser Ser Gly Ile Ser Arg
                20                  25                  30

Tyr Leu Ala Trp Tyr Gln Gln Ala Pro Gly Lys Ala Pro Lys Leu Leu
            35                  40                  45

Ile Tyr Ala Ala Ser Thr Leu Gln Thr Gly Val Pro Ser Arg Phe Ser
    50                  55                  60

Gly Ser Gly Ser Gly Thr Glu Phe Thr Leu Thr Ile Asn Ser Leu Gln
 65                  70                  75                  80

Pro Glu Asp Phe Ala Thr Tyr Tyr Cys Gln His Leu Asn Ser Tyr Pro
                 85                  90                  95
```

```
Leu Thr Phe Gly Gly Gly Thr Lys Val Asp Ile Lys Arg Ala Ser Gly
            100                 105                 110

Gly Gly Gly Ser Gly Gly Gly Ser Gly Gly Gly Ser Gly Gly
        115                 120                 125

Gly Gly Ser Gly Gly Gly Ser Gly Gly Gly Ser Ala Glu Val
    130                 135                 140

Gln Leu Val Glu Ser Gly Ala Glu Val Lys Lys Pro Gly Glu Ser Leu
145                 150                 155                 160

Arg Ile Ser Cys Lys Gly Ser Gly Tyr Ser Ile Ser Ser Tyr Trp Ile
                165                 170                 175

Ser Trp Val Arg Gln Met Pro Gly Lys Gly Leu Glu Trp Met Gly Lys
            180                 185                 190

Ile Asp Pro Gly Asp Ser Tyr Ile Asn Tyr Ser Pro Ser Phe Gln Gly
        195                 200                 205

His Val Thr Ile Ser Ala Asp Lys Ser Ile Asn Thr Ala Tyr Leu Gln
    210                 215                 220

Trp Asn Ser Leu Lys Ala Ser Asp Thr Ala Met Tyr Tyr Cys Ala Arg
225                 230                 235                 240

Gly Gly Arg Asp Phe Gly Asp Ser Phe Asp Tyr Trp Gly Gln Gly Thr
                245                 250                 255

Leu Val Thr Val Ser Ser
            260

<210> SEQ ID NO 59
<211> LENGTH: 837
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(837)

<400> SEQUENCE: 59 atg aaa tac ctg ctg ccg acc gct gct gct ggt ctg ctg ctc ctc gct      48
Met Lys Tyr Leu Leu Pro Thr Ala Ala Ala Gly Leu Leu Leu Leu Ala
1               5                   10                  15 gcc cag ccg gcg atg gcc gct gaa gtt caa ctt gtt gaa tct ggt gct      96
Ala Gln Pro Ala Met Ala Ala Glu Val Gln Leu Val Glu Ser Gly Ala
                20                  25                  30 gaa gtt aaa aaa ccg ggt gaa tct ctg cgt atc tct tgc aaa ggt tct     144
Glu Val Lys Lys Pro Gly Glu Ser Leu Arg Ile Ser Cys Lys Gly Ser
            35                  40                  45 ggt tgc atc atc tct tct tac tgg atc agc tgg gtt cgt cag atg ccg     192
Gly Cys Ile Ile Ser Ser Tyr Trp Ile Ser Trp Val Arg Gln Met Pro
        50                  55                  60 ggc aag ggc ctg gaa tgg atg ggt aaa att gat ccg ggc gac agc tat     240
Gly Lys Gly Leu Glu Trp Met Gly Lys Ile Asp Pro Gly Asp Ser Tyr
65                  70                  75                  80 att aac tac agc ccg agc ttt cag ggc cat gtt acc atc agc gcc gat     288
Ile Asn Tyr Ser Pro Ser Phe Gln Gly His Val Thr Ile Ser Ala Asp
                85                  90                  95 aaa agc att aac acc gct tac ctg caa tgg aac agc ctg aaa gcg agc     336
Lys Ser Ile Asn Thr Ala Tyr Leu Gln Trp Asn Ser Leu Lys Ala Ser
            100                 105                 110 gac acc gcg atg tac tac tgt gcc cgt ggc ggt cgt gac ttc ggt gat     384
Asp Thr Ala Met Tyr Tyr Cys Ala Arg Gly Gly Arg Asp Phe Gly Asp
        115                 120                 125 agc ttc gat tac tgg ggt cag ggc acc ctg gtg acc gtg agc agc ggt     432
```

```
Ser Phe Asp Tyr Trp Gly Gln Gly Thr Leu Val Thr Val Ser Ser Gly
    130                 135                 140 ggt ggc ggc agc ggt ggt ggc ggc agc ggc ggc ggc agc gat gtt           480
Gly Gly Gly Ser Gly Gly Gly Gly Ser Gly Gly Gly Ser Asp Val
145                 150                 155                 160 gtg atg acc cag agc ccg agc ttc ctg agc gcg ttc gtt ggt gac cgt       528
Val Met Thr Gln Ser Pro Ser Phe Leu Ser Ala Phe Val Gly Asp Arg
                165                 170                 175 atc acc att acc tgc cgc gcc agc agc ggc atc agc cgc tat ctg gcg       576
Ile Thr Ile Thr Cys Arg Ala Ser Ser Gly Ile Ser Arg Tyr Leu Ala
            180                 185                 190 tgg tat cag caa gca ccg ggt aaa gca ccg aaa ctg ctg atc tat gct       624
Trp Tyr Gln Gln Ala Pro Gly Lys Ala Pro Lys Leu Leu Ile Tyr Ala
        195                 200                 205 gca agc acc ctg caa acc ggc gtt ccg agc cgt ttt agc ggt agc ggc       672
Ala Ser Thr Leu Gln Thr Gly Val Pro Ser Arg Phe Ser Gly Ser Gly
    210                 215                 220 agc ggc acc gag ttc acc ctg acc atc aac agc ctg caa ccg gag gat       720
Ser Gly Thr Glu Phe Thr Leu Thr Ile Asn Ser Leu Gln Pro Glu Asp
225                 230                 235                 240 ttt gcc acc tat tac tgc caa cac ctg aat agc tat ccg ctg acc ttc       768
Phe Ala Thr Tyr Tyr Cys Gln His Leu Asn Ser Tyr Pro Leu Thr Phe
                245                 250                 255 ggt ggc ggc acc aaa gtg gac atc aaa cgc gcg gcc gca ctc gag cac       816
Gly Gly Gly Thr Lys Val Asp Ile Lys Arg Ala Ala Ala Leu Glu His
                260                 265                 270 cac cac cac cac cac taa taa                                           837
His His His His His
        275

<210> SEQ ID NO 60
<211> LENGTH: 277
<212> TYPE: PRT
<213> ORGANISM: Artificial
<220> FEATURE:
<223> OTHER INFORMATION: Synthetic Construct

<400> SEQUENCE: 60

Met Lys Tyr Leu Leu Pro Thr Ala Ala Ala Gly Leu Leu Leu Leu Ala
1               5                   10                  15

Ala Gln Pro Ala Met Ala Ala Glu Val Gln Leu Val Glu Ser Gly Ala
            20                  25                  30

Glu Val Lys Lys Pro Gly Glu Ser Leu Arg Ile Ser Cys Lys Gly Ser
        35                  40                  45

Gly Cys Ile Ile Ser Ser Tyr Trp Ile Ser Trp Val Arg Gln Met Pro
    50                  55                  60

Gly Lys Gly Leu Glu Trp Met Gly Lys Ile Asp Pro Gly Asp Ser Tyr
65                  70                  75                  80

Ile Asn Tyr Ser Pro Ser Phe Gln Gly His Val Thr Ile Ser Ala Asp
                85                  90                  95

Lys Ser Ile Asn Thr Ala Tyr Leu Gln Trp Asn Ser Leu Lys Ala Ser
            100                 105                 110

Asp Thr Ala Met Tyr Tyr Cys Ala Arg Gly Gly Arg Asp Phe Gly Asp
        115                 120                 125

Ser Phe Asp Tyr Trp Gly Gln Gly Thr Leu Val Thr Val Ser Ser Gly
    130                 135                 140

Gly Gly Gly Ser Gly Gly Gly Gly Ser Gly Gly Gly Ser Asp Val
145                 150                 155                 160
```

```
Val Met Thr Gln Ser Pro Ser Phe Leu Ser Ala Phe Val Gly Asp Arg
            165                 170                 175

Ile Thr Ile Thr Cys Arg Ala Ser Ser Gly Ile Ser Arg Tyr Leu Ala
            180                 185                 190

Trp Tyr Gln Gln Ala Pro Gly Lys Ala Pro Lys Leu Leu Ile Tyr Ala
            195                 200                 205

Ala Ser Thr Leu Gln Thr Gly Val Pro Ser Arg Phe Ser Gly Ser Gly
            210                 215                 220

Ser Gly Thr Glu Phe Thr Leu Thr Ile Asn Ser Leu Gln Pro Glu Asp
225                 230                 235                 240

Phe Ala Thr Tyr Tyr Cys Gln His Leu Asn Ser Tyr Pro Leu Thr Phe
                245                 250                 255

Gly Gly Gly Thr Lys Val Asp Ile Lys Arg Ala Ala Ala Leu Glu His
                260                 265                 270

His His His His His
            275

<210> SEQ ID NO 61
<211> LENGTH: 837
<212> TYPE: DNA
<213> ORGANISM: Artificial
<220> FEATURE:
<223> OTHER INFORMATION: Polynucleotide encoding scFv polypeptide
<220> FEATURE:
<221> NAME/KEY: CDS
<222> LOCATION: (1)..(837)

<400> SEQUENCE: 61 atg aaa tac ctg ctg ccg acc gct gct gct ggt ctg ctc ctc gct        48
Met Lys Tyr Leu Leu Pro Thr Ala Ala Ala Gly Leu Leu Leu Leu Ala
1               5                   10                  15 gcc cag ccg gcg atg gcc gct gaa gtt caa ctt gtt gaa tct ggt gct    96
Ala Gln Pro Ala Met Ala Ala Glu Val Gln Leu Val Glu Ser Gly Ala
                20                  25                  30 gaa gtt aaa aaa ccg ggt gaa tct ctg cgt atc tct tgc aaa ggt tct   144
Glu Val Lys Lys Pro Gly Glu Ser Leu Arg Ile Ser Cys Lys Gly Ser
            35                  40                  45 ggt tat atc atc tct tct tac tgg atc agc tgg gtt cgt cag atg ccg   192
Gly Tyr Ile Ile Ser Ser Tyr Trp Ile Ser Trp Val Arg Gln Met Pro
        50                  55                  60 ggc aag ggc ctg gaa tgg atg ggt aaa att gat ccg ggc gac agc tat   240
Gly Lys Gly Leu Glu Trp Met Gly Lys Ile Asp Pro Gly Asp Ser Tyr
65                  70                  75                  80 att aac tac agc ccg agc ttt cag ggc cat gtt acc atc agc gcc gat   288
Ile Asn Tyr Ser Pro Ser Phe Gln Gly His Val Thr Ile Ser Ala Asp
                85                  90                  95 aaa agc att aac acc gct tac ctg caa tgg aac agc ctg aaa gcg agc   336
Lys Ser Ile Asn Thr Ala Tyr Leu Gln Trp Asn Ser Leu Lys Ala Ser
            100                 105                 110 gac acc gcg atg tac tac tgt gcc cgt ggc ggt cgt gac ttc ggt gat   384
Asp Thr Ala Met Tyr Tyr Cys Ala Arg Gly Gly Arg Asp Phe Gly Asp
        115                 120                 125 agc ttc gat tac tgg ggt cag ggc acc ctg gtg acc gtg agc agc ggt   432
Ser Phe Asp Tyr Trp Gly Gln Gly Thr Leu Val Thr Val Ser Ser Gly
    130                 135                 140 ggt ggc agc ggt ggc ggc agc ggc ggc ggc agc gat gtt               480
Gly Gly Ser Gly Gly Gly Ser Gly Gly Gly Ser Asp Val
145                 150                 155                 160 gtg atg acc cag agc ccg agc ttc ctg agc gcg ttc gtt ggt gac cgt   528
Val Met Thr Gln Ser Pro Ser Phe Leu Ser Ala Phe Val Gly Asp Arg
```

```
                165                 170                 175
atc acc att acc tgc cgc gcc agc agc ggc atc agc cgc tat ctg gcg      576
Ile Thr Ile Thr Cys Arg Ala Ser Ser Gly Ile Ser Arg Tyr Leu Ala
            180                 185                 190 tgg tat cag caa gca ccg ggt aaa gca ccg aaa ctg ctg atc tat gct      624
Trp Tyr Gln Gln Ala Pro Gly Lys Ala Pro Lys Leu Leu Ile Tyr Ala
        195                 200                 205 gca agc acc ctg caa acc ggc gtt ccg agc cgt ttt agc ggt agc ggc      672
Ala Ser Thr Leu Gln Thr Gly Val Pro Ser Arg Phe Ser Gly Ser Gly
    210                 215                 220 agc ggc acc gag ttc acc ctg acc atc aac agc ctg caa ccg gag gat      720
Ser Gly Thr Glu Phe Thr Leu Thr Ile Asn Ser Leu Gln Pro Glu Asp
225                 230                 235                 240 ttt gcc acc tat tac tgc caa cac ctg aat agc tat ccg ctg acc ttc      768
Phe Ala Thr Tyr Tyr Cys Gln His Leu Asn Ser Tyr Pro Leu Thr Phe
                245                 250                 255 ggt ggc ggc acc aaa gtg gac atc aaa cgc gcg gcc gca ctc gag cac      816
Gly Gly Gly Thr Lys Val Asp Ile Lys Arg Ala Ala Ala Leu Glu His
            260                 265                 270 cac cac cac cac cac taa taa                                          837
His His His His His
        275

<210> SEQ ID NO 62
<211> LENGTH: 277
<212> TYPE: PRT
<213> ORGANISM: Artificial
<220> FEATURE:
<223> OTHER INFORMATION: Synthetic Construct

<400> SEQUENCE: 62

Met Lys Tyr Leu Leu Pro Thr Ala Ala Ala Gly Leu Leu Leu Leu Ala
1               5                   10                  15

Ala Gln Pro Ala Met Ala Ala Glu Val Gln Leu Val Glu Ser Gly Ala
            20                  25                  30

Glu Val Lys Lys Pro Gly Glu Ser Leu Arg Ile Ser Cys Lys Gly Ser
        35                  40                  45

Gly Tyr Ile Ile Ser Ser Tyr Trp Ile Ser Trp Val Arg Gln Met Pro
    50                  55                  60

Gly Lys Gly Leu Glu Trp Met Gly Lys Ile Asp Pro Gly Asp Ser Tyr
65                  70                  75                  80

Ile Asn Tyr Ser Pro Ser Phe Gln Gly His Val Thr Ile Ser Ala Asp
                85                  90                  95

Lys Ser Ile Asn Thr Ala Tyr Leu Gln Trp Asn Ser Leu Lys Ala Ser
            100                 105                 110

Asp Thr Ala Met Tyr Tyr Cys Ala Arg Gly Gly Arg Asp Phe Gly Asp
        115                 120                 125

Ser Phe Asp Tyr Trp Gly Gln Gly Thr Leu Val Thr Val Ser Ser Gly
    130                 135                 140

Gly Gly Gly Ser Gly Gly Gly Ser Gly Gly Gly Gly Ser Asp Val
145                 150                 155                 160

Val Met Thr Gln Ser Pro Ser Phe Leu Ser Ala Phe Val Gly Asp Arg
                165                 170                 175

Ile Thr Ile Thr Cys Arg Ala Ser Ser Gly Ile Ser Arg Tyr Leu Ala
            180                 185                 190

Trp Tyr Gln Gln Ala Pro Gly Lys Ala Pro Lys Leu Leu Ile Tyr Ala
        195                 200                 205
```

```
Ala Ser Thr Leu Gln Thr Gly Val Pro Ser Arg Phe Ser Gly Ser Gly
    210                 215                 220

Ser Gly Thr Glu Phe Thr Leu Thr Ile Asn Ser Leu Gln Pro Glu Asp
225                 230                 235                 240

Phe Ala Thr Tyr Tyr Cys Gln His Leu Asn Ser Tyr Pro Leu Thr Phe
                245                 250                 255

Gly Gly Gly Thr Lys Val Asp Ile Lys Arg Ala Ala Ala Leu Glu His
            260                 265                 270

His His His His His
            275

<210> SEQ ID NO 63
<211> LENGTH: 363
<212> TYPE: DNA
<213> ORGANISM: Artificial
<220> FEATURE:
<223> OTHER INFORMATION: polynucleotide encoding Heavy chain of scFv
      peptide
<220> FEATURE:
<221> NAME/KEY: CDS
<222> LOCATION: (1)..(363)

<400> SEQUENCE: 63 gct gaa gtt caa ctt gtt gaa tct ggt gct gaa gtt aaa aaa ccg ggt      48
Ala Glu Val Gln Leu Val Glu Ser Gly Ala Glu Val Lys Lys Pro Gly
1               5                   10                  15 gaa tct ctg cgt atc tct tgc aaa ggt tct ggt tgc atc atc tct tct      96
Glu Ser Leu Arg Ile Ser Cys Lys Gly Ser Gly Cys Ile Ile Ser Ser
            20                  25                  30 tac tgg atc agc tgg gtt cgt cag atg ccg ggc aag ggc ctg gaa tgg     144
Tyr Trp Ile Ser Trp Val Arg Gln Met Pro Gly Lys Gly Leu Glu Trp
        35                  40                  45 atg ggt aaa att gat ccg ggc gac agc tat att aac tac agc ccg agc     192
Met Gly Lys Ile Asp Pro Gly Asp Ser Tyr Ile Asn Tyr Ser Pro Ser
    50                  55                  60 ttt cag ggc cat gtt acc atc agc gcc gat aaa agc att aac acc gct     240
Phe Gln Gly His Val Thr Ile Ser Ala Asp Lys Ser Ile Asn Thr Ala
65                  70                  75                  80 tac ctg caa tgg aac agc ctg aaa gcg agc gac acc gcg atg tac tac     288
Tyr Leu Gln Trp Asn Ser Leu Lys Ala Ser Asp Thr Ala Met Tyr Tyr
                85                  90                  95 tgt gcc cgt ggc ggt cgt gac ttc ggt gat agc ttc gat tac tgg ggt     336
Cys Ala Arg Gly Gly Arg Asp Phe Gly Asp Ser Phe Asp Tyr Trp Gly
            100                 105                 110 cag ggc acc ctg gtg acc gtg agc agc                                 363
Gln Gly Thr Leu Val Thr Val Ser Ser
        115                 120

<210> SEQ ID NO 64
<211> LENGTH: 121
<212> TYPE: PRT
<213> ORGANISM: Artificial
<220> FEATURE:
<223> OTHER INFORMATION: Synthetic Construct

<400> SEQUENCE: 64

Ala Glu Val Gln Leu Val Glu Ser Gly Ala Glu Val Lys Lys Pro Gly
1               5                   10                  15

Glu Ser Leu Arg Ile Ser Cys Lys Gly Ser Gly Cys Ile Ile Ser Ser
            20                  25                  30

Tyr Trp Ile Ser Trp Val Arg Gln Met Pro Gly Lys Gly Leu Glu Trp
        35                  40                  45
```

```
Met Gly Lys Ile Asp Pro Gly Asp Ser Tyr Ile Asn Tyr Ser Pro Ser
    50                  55                  60

Phe Gln Gly His Val Thr Ile Ser Ala Asp Lys Ser Ile Asn Thr Ala
65                  70                  75                  80

Tyr Leu Gln Trp Asn Ser Leu Lys Ala Ser Asp Thr Ala Met Tyr Tyr
                85                  90                  95

Cys Ala Arg Gly Gly Arg Asp Phe Gly Asp Ser Phe Asp Tyr Trp Gly
            100                 105                 110

Gln Gly Thr Leu Val Thr Val Ser Ser
        115                 120

<210> SEQ ID NO 65
<211> LENGTH: 327
<212> TYPE: DNA
<213> ORGANISM: Artificial
<220> FEATURE:
<223> OTHER INFORMATION: polynucleotide encoding light chain from scFv
      peptide
<220> FEATURE:
<221> NAME/KEY: CDS
<222> LOCATION: (1)..(327)

<400> SEQUENCE: 65 gat gtt gtg atg acc cag agc ccg agc ttc ctg agc gcg ttc gtt ggt      48
Asp Val Val Met Thr Gln Ser Pro Ser Phe Leu Ser Ala Phe Val Gly
1               5                   10                  15 gac cgt atc acc att acc tgc cgc gcc agc agc ggc atc agc cgc tat      96
Asp Arg Ile Thr Ile Thr Cys Arg Ala Ser Ser Gly Ile Ser Arg Tyr
                20                  25                  30 ctg gcg tgg tat cag caa gca ccg ggt aaa gca ccg aaa ctg ctg atc     144
Leu Ala Trp Tyr Gln Gln Ala Pro Gly Lys Ala Pro Lys Leu Leu Ile
            35                  40                  45 tat gct gca agc acc ctg caa acc ggc gtt ccg agc cgt ttt agc ggt     192
Tyr Ala Ala Ser Thr Leu Gln Thr Gly Val Pro Ser Arg Phe Ser Gly
        50                  55                  60 agc ggc agc ggc acc gag ttc acc ctg acc atc aac agc ctg caa ccg     240
Ser Gly Ser Gly Thr Glu Phe Thr Leu Thr Ile Asn Ser Leu Gln Pro
65                  70                  75                  80 gag gat ttt gcc acc tat tac tgc caa cac ctg aat agc tat ccg ctg     288
Glu Asp Phe Ala Thr Tyr Tyr Cys Gln His Leu Asn Ser Tyr Pro Leu
                85                  90                  95 acc ttc ggt ggc ggc acc aaa gtg gac atc aaa cgc gcg                 327
Thr Phe Gly Gly Gly Thr Lys Val Asp Ile Lys Arg Ala
            100                 105

<210> SEQ ID NO 66
<211> LENGTH: 109
<212> TYPE: PRT
<213> ORGANISM: Artificial
<220> FEATURE:
<223> OTHER INFORMATION: Synthetic Construct

<400> SEQUENCE: 66

Asp Val Val Met Thr Gln Ser Pro Ser Phe Leu Ser Ala Phe Val Gly
1               5                   10                  15

Asp Arg Ile Thr Ile Thr Cys Arg Ala Ser Ser Gly Ile Ser Arg Tyr
                20                  25                  30

Leu Ala Trp Tyr Gln Gln Ala Pro Gly Lys Ala Pro Lys Leu Leu Ile
            35                  40                  45

Tyr Ala Ala Ser Thr Leu Gln Thr Gly Val Pro Ser Arg Phe Ser Gly
        50                  55                  60
```

```
Ser Gly Ser Gly Thr Glu Phe Thr Leu Thr Ile Asn Ser Leu Gln Pro
 65                  70                  75                  80

Glu Asp Phe Ala Thr Tyr Tyr Cys Gln His Leu Asn Ser Tyr Pro Leu
                 85                  90                  95

Thr Phe Gly Gly Gly Thr Lys Val Asp Ile Lys Arg Ala
            100                 105

<210> SEQ ID NO 67
<211> LENGTH: 66
<212> TYPE: DNA
<213> ORGANISM: Artificial
<220> FEATURE:
<223> OTHER INFORMATION: pelB signal sequence
<220> FEATURE:
<221> NAME/KEY: CDS
<222> LOCATION: (1)..(66)

<400> SEQUENCE: 67 atg aaa tac ctg ctg ccg acc gct gct gct ggt ctg ctg ctc ctc gct      48
Met Lys Tyr Leu Leu Pro Thr Ala Ala Ala Gly Leu Leu Leu Leu Ala
 1               5                  10                  15 gcc cag ccg gcg atg gcc                                              66
Ala Gln Pro Ala Met Ala
            20

<210> SEQ ID NO 68
<211> LENGTH: 22
<212> TYPE: PRT
<213> ORGANISM: Artificial
<220> FEATURE:
<223> OTHER INFORMATION: Synthetic Construct

<400> SEQUENCE: 68

Met Lys Tyr Leu Leu Pro Thr Ala Ala Ala Gly Leu Leu Leu Leu Ala
 1               5                  10                  15

Ala Gln Pro Ala Met Ala
            20

<210> SEQ ID NO 69
<211> LENGTH: 14
<212> TYPE: PRT
<213> ORGANISM: Candida albicans

<400> SEQUENCE: 69

Asn Lys Ile Leu Lys Val Ile Arg Lys Asn Ile Val Lys Lys
 1               5                  10

<210> SEQ ID NO 70
<211> LENGTH: 15
<212> TYPE: PRT
<213> ORGANISM: Artificial
<220> FEATURE:
<223> OTHER INFORMATION: Scrambled peptide

<400> SEQUENCE: 70

Ser Phe Lys Trp Gly Val Thr Thr Ser Leu Ser Tyr Phe Pro Lys
 1               5                  10                  15

<210> SEQ ID NO 71
<211> LENGTH: 5
<212> TYPE: PRT
<213> ORGANISM: artificial
<220> FEATURE:
<223> OTHER INFORMATION: scFv linker sequence
```

```
-continued
<400> SEQUENCE: 71

Gly Gly Gly Gly Ser
1               5
```